US008519145B2

(12) United States Patent
Kang et al.

(10) Patent No.: US 8,519,145 B2
(45) Date of Patent: Aug. 27, 2013

(54) ARYL COMPOUNDS AS PPAR LIGANDS AND THEIR USE

(75) Inventors: Heonjoong Kang, Gyeonggi-do (KR); Jungwook Chin, Seoul (KR); Jaehwan Lee, Seoul (KR)

(73) Assignee: Seoul National University Industry Foundation (KR)

( * ) Notice: Subject to any disclaimer, the term of this patent is extended or adjusted under 35 U.S.C. 154(b) by 921 days.

(21) Appl. No.: 12/517,156

(22) PCT Filed: Dec. 1, 2007

(86) PCT No.: PCT/KR2007/006170
§ 371 (c)(1),
(2), (4) Date: Dec. 18, 2009

(87) PCT Pub. No.: WO2008/066356
PCT Pub. Date: Jun. 5, 2008

(65) Prior Publication Data
US 2012/0271055 A1  Oct. 25, 2012

(30) Foreign Application Priority Data

Dec. 2, 2006 (KR) ........................ 10-2006-0121074

(51) Int. Cl.
*A61K 31/44* (2006.01)
*C07D 213/55* (2006.01)
(52) U.S. Cl.
USPC ......................................... 546/342; 514/354
(58) Field of Classification Search
None
See application file for complete search history.

(56) References Cited

U.S. PATENT DOCUMENTS

| 6,875,780 B2 | 4/2005 | Auerbach et al. |
| 6,939,875 B2 | 9/2005 | Auerbach et al. |
| 7,115,611 B2 | 10/2006 | Ackermann et al. |
| 7,338,960 B2 * | 3/2008 | Bell et al. ...................... 514/277 |

FOREIGN PATENT DOCUMENTS

| JP | 2005179281 | 7/2005 |
| JP | 2005534672 | 11/2005 |
| WO | 2001-00603 | 1/2001 |
| WO | 0100603 | 1/2001 |
| WO | 2002-62774 | 8/2002 |
| WO | 02062774 | 8/2002 |
| WO | 2003-072100 | 9/2003 |
| WO | 03072100 | 9/2003 |
| WO | 2004/000315 | 12/2003 |
| WO | 2005049573 | 6/2005 |
| WO | 2006071103 | 7/2006 |
| WO | 2006091047 | 8/2006 |

OTHER PUBLICATIONS

Hardy, J. Neuron 2006 vol. 52 pp. 3-13.*

Japanese Office Action—Japanese Application No. 2009-539189 issued on Apr. 17, 2012, citing JP2005-179281, WO2005/049573, JP2005-534672, WO2006/091047, and WO2006/071103.
Canadian Office Action—Canadian Application No. 2,669,639 issued on Mar. 12, 2012, citing WO 2004/000315.
Issemann et al.; "Activation of a member of the steroid hormone receptor superfamily by peroxisome proliferators" Nature, 1990, vol. 347, pp. 645-650.
Auborn et al.; "Replicative intermediates of human papillomavirus type 11 in laryngeal papillomas: Site of replication initiation and direction of replication" Proc. Natl. Acad. Sci., 1994, vol. 91, pp. 7340-7344.
Lambert et al.; "The ORD1 gene encodes a transcription factor involved in oxygen regulation and is indentical to IXR1, a gene that confers cisplatin sensitivity to *Saccharomyces cerevisiae*" Proc. Natl. Acad. Sci., 1994, vol. 91, pp. 7345-4349.
Brooks et al.; "Modulators of Leukotriene Biosythesis and Receptor Activation" Journal of Medicinal Chemistry, 1996, vol. 39, No. 14, pp. 2629-2654.
Johnson et al.; "Structural Requirements and Cell-type Specificity for Ligand Activation of Peroxisome Proliferator-activated Receptors" J. Steroid Biochem. Molec. Biol., 1997, vol. 63, No. 1-3, pp. 1-8.
Lee et al.; "Transcriptional Repression of Atherogenic Inflammation: Modulation by PPAR" Science, 2003, vol. 302, pp. 453-457.
Lee et al.; "PPAR regulates glucose metabolism and insulin sensitivity" PNAS, 2006, vol. 103, No. 9, pp. 3444-3449.
Tanaka et al.; "Activation of peroxisome proliferator-activated receptor induces fatty acid oxidation in skeletal muscle and attenuates metabolic syndrome" PNAS, 2003, vol. 100, No. 26, pp. 15924-15929.
Oliver Jr. et al.; "A selective peroxisome proliferator-activated receptor agonist promotes reverse cholesterol transport" PNAS, 2001, vol. 98, No. 9, pp. 5306-5311.
Dreyer et al.; "Control of the Peroxisomal Oxidation Pathway by a Novel Family of Nuclear Hormone Receptors" Cell, 1992, vol. 68, pp. 879-887.
Rosen et al.; "PPAR is Required for the Differentiation of Adipose Tissue in Vivo and in Vitro" Molecular Cell, 1999, vol. 4, pp. 511-517.
Kubota et al.; "PPAR Mediates High-Fat Diet-Induced Adipocyte Hypertrophy and Insulin Resistance" Molecular Cell, 1999, vol. 4, pp. 597-609.
Barak et al.; "PPAR Is Required for Placental, Cardiac, and Adipose Tissue Development" Molecular Cell, 1999, vol. 4, pp. 585-595.
Palmer et al.; "Peroxisome Proliferator Activated Receptor Expression in Human Liver" Molecular Pharmacology, 1998, vol. 53, pp. 14-22.

(Continued)

*Primary Examiner* — Janet Andres
*Assistant Examiner* — Heidi Reese
(74) *Attorney, Agent, or Firm* — Cantor Colburn LLP

(57) ABSTRACT

The present invention relates to a compound as a peroxisome proliferator activated receptor (PPAR) activator and a hydrate, a solvate, a stereoisomer and a pharmaceutically acceptable salt thereof, and a pharmaceutical composition, a cosmetic composition, a muscle strengthening agent, a memory improving agent, a therapeutic agent for dementia and Parkinson's disease, a functional food and a feed composition containing the same.

17 Claims, No Drawings

(56) References Cited

OTHER PUBLICATIONS

Wang et al.; "Peroxisome-Proliferator-Activated Receptor Activates Fat Metabolism to Prevent Obesity" Cell, 2003, vol. 113, pp. 159-170.

Peters et al.; "Alterations in Lipoprotein Metabolism in Peroxisome Proliferator-activated Receptor deficient Mice" The Journal of Biological Chemistry, 1997, vol. 272, No. 43, pp. 27307-27312.

Dreyer et al.; "Positive regulation of the peroxisomal oxidation pathway by fatty acids through activation of peroxisome proliferator-activated receptors (PPAR)" Biol Cell, 1993, vol. 77, pp. 67-76.

Motojima et al.; "Expression of Putative Fatty Acid Transporter Genes Are Regulated by Peroxisome Proliferator-activated Receptor and Activators in a Tissue- and Inducer-specific Manner" The Journal of Biological Chemistry, 1998, vol. 273, No. 27, pp. 16710-16714.

Clapham et al.; "Mice overexpressing human uncoupling protein-3 in skeletal muscle are hyperphagic and lean" Letters to Nature. May 2000.

Gottshalk et al.; "Identification of immunosuppressant-induced apoptosis in a murine B-cell line and its prevention by bcl-x but not bcl-2" Proc. Natl. Acad. Sci., 1994, vol. 91, pp. 7350-7354.

Peters et al.; "Growth, Adipose, Brain, and Skin Alterations Resulting from Targeted Disruption of the Mouse Peroxisome Proliferator-Activated Receptor" Molecular and Cellular Biology, 2000, vol. 20, No. 14, pp. 5119-5128.

Bennett et al.; "Protein-tyrosine-phosphatase SHPTP2 couples platelet-derived growth factor receptor B to Ras" Proc. Natl. Acad. Sci., 1994, vol. 91, pp. 7335-7339.

Kliewer et al.; "Differential expression and activation of a family of murine peroxisome proliferator-activated receptors" Proc. Natl. Acad. Sci., 1994, vol. 91, pp. 7355-7359.

Lambe et al.; "Species differences in sequence and activity of the peroxisome proliferator response element (PPRE) within the acyl CoA oxidase gene promoter" Toxicology Letters 110, 1999, pp. 119-127.

Wang et al.; "Regulation of Muscle Fiber Type and Running Endurance by PPAR" PLoS Biology, 2004, vol. 2, Issue 10, pp. 1532-1539.

Schmidt et al.; "Identification of a New Member of the Steroid Hormone Receptor Superfamily That Is Activated by a Peroxisome Proliferator and Fatty Acids" Molecular Endocrinology, 1992, vol. 6, No. 4, pp. 1634-1641.

Chen et al.; "Identification of two mPPAR related receptors and evidence for the existence of five subfamily members" Biochemical and Biophysical Research Communications, 1993, vol. 196, No. 2, pp. 671-677.

Amri et al.; "Cloning of a Protein that Mediates Transcriptional Effects of Fatty Acids in Preadipocytes" The Journal of Biological Chemistry, 1995, vol. 270, No. 5, pp. 2367-2371.

Braissant.; "Differential Expression of Peroxisome Proliferator-Activated Receptors (PPARs): Tissue Distribution of PPAR-a, -B, and -y in the Adult Rat" Endocrinology, 1996, vol. 137, No. 1, pp. 354-366.

Lim et al.; "Cyclo-oxygenase-2-derived prostacyclin mediates embryo implantation in the mouse via PPAR" Genes & Development, 1999, pp. 1561-1574.

Kremarik-Bouillaud et al.; "Regional distribution of PPAR in the cerebellum of the rat" Journal of Chemical Neuroanatomy, 2000, vol. 19, pp. 225-232.

Tan et al.; "Critical roles of PPAR in keratinocyte response to inflammation" Genes & Development, 2001, pp. 3263-3277.

Henson; "Suppression of macrophage inflammatory responses by PPARs" PNAS, 2003, vol. 100, No. 11, pp. 6295-6296.

Barak et al.; "Effects of peroxisome proliferator-activated receptor on placentation, adiposity, and colorectal cancer" PNAS, 2002, vol. 99, No. 1, pp. 303-308.

International Search Report for PCT/KR2007/006170 dated Mar. 13, 2008.

* cited by examiner

ARYL COMPOUNDS AS PPAR LIGANDS AND THEIR USE

TECHNICAL FIELD

The present invention relates to the compound represented by formula (I) as a PPAR (Peroxisome Proliferator Activated Receptor) ligand and a hydrate, a solvate, a stereoisomer and a pharmaceutically acceptable salt thereof, which can be used for the treatment of obesity, hyperlipidemia, arteriosclerosis and diabetes, and a pharmaceutical composition, a cosmetic composition, an strengthening agent, a memory improving agent, a therapeutic agent for dementia and Parkinson's disease, a functional food and a feed composition containing the same.

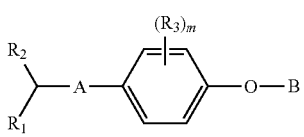

[Formula I]

BACKGROUND ART

Among nuclear receptors, PPAR (Peroxisome Proliferator Activated Receptor) is known to have three subtypes, which are PPARα, PPARγ and PPARδ (*Nature*, 1990, 347, p 645-650, *Proc. Natl. Acad. Sci. USA* 1994, 91, p 7335-7359). PPARα, PPARγ and PPARδ have tissue specific functions in vivo and different regions for expression. PPARα is mainly expressed in the heart, kidney, skeletal muscle and large intestine in human (*Mol. Pharmacol.* 1998, 53, p 14-22, *Toxicol. Lett.* 1999, 110, p 119-127, *J. Biol. Chem.* 1998, 273, p 16710-16714), and is involved in β-oxidation of peroxisome and mitochondria (*Biol. Cell.* 1993, 77, p 67-76, *J. Biol. Chem.* 1997, 272, p 27307-27312). PPARγ is expressed in the skeletal muscle at a low level but mainly expressed in the adipose tissue to induce the adipocyte differentiation and to store energy as the form of fat, and is involved in homeostatic regulation of insulin and glucose (*Moll. Cell.* 1999, 4, p 585-594, p 597-609, p 611-617). PPARδ, is preserved evolutionarily in mammals including human and vertebrates including rodents and sea squirts. The first PPARδ found in *Xenopus laevis* was known as PPARβ (Cell 1992, 68, p 879-887) and PPARδ found in human was named differently as NUC1 (*Mol. Endocrinol.* 1992, 6, p 1634-1641), PPARδ (*Proc. Natl. Acad. Sci. USA* 1994, 91, p 7355-7359), NUC1 (*Biochem. Biophys. Res. Commun.* 1993, 196, p 671-677), FAAR (*J. Bio. Chem.* 1995, 270, p 2367-2371), ect, but they have been renamed as PPARδ recently. In human, PPARδ is known to exist in chromosome 6p21.1-p21.2. In rats, PPARδ mRNA is found in various cells but the level is lower than those of PPARα or PPARγ (*Endocrinology* 1996, 137, p 354-366, *J. Bio. Chem.* 1995, 270, p 2367-2371, *Endocrinology* 1996, 137, p 354-366). The previous studies confirmed that PPARδ plays an important role in the reproductive cell expression (*Genes Dev.* 1999, 13, p 1561-1574) and has physiological functions of differentiating neuronal cells (*J. Chem. Neuroanat* 2000, 19, p 225-232) in central nervous system (CNS) and wound healing with anti-inflammatory effect (*Genes Dev.* 2001, 15, p 3263-3277, *Proc. Natl. Acad. Sci. USA* 2003, 100, p 6295-6296). Recent studies also confirmed that PPARδ is involved in the adipocyte differentiation and lipid metabolism (*Proc. Natl. Acad. Sci. USA* 2002, 99, p 303-308, *Mol. Cell. Biol.* 2000, 20, p 5119-5128). For example, PPARδ activates the expression of key gene involved in β-oxidation in fatty acid catabolism and uncoupling proteins (UCPs), the gene involved in energy metabolism, which brings the effect of improving obesity (*Nature* 2000, 406, p 415-418, *Cell* 2003, 113, p 159-170, *PLoS Biology* 2004, 2, p 1532-1539). The activation of PPARδ increases the HDL level, improves type 2 diabetes without weight changes (*Proc. Natl. Acad. Sci. USA* 2001, 98, p 5306-5311, 2003, 100, p 15924-15929, 2006, 103, p 3444-3449), and favors the treatment of arteriosclerosis by inhibiting the gene associated with arteriosclerosis (*Science*, 2003, 302, p 453-457). Therefore, studies on the regulation of lipid metabolism using PPARδ provide a clue to develop a treatment method for obesity, diabetes, hyperlipidemia and arteriosclerosis.

PPARδ is involved in the mitochondria generation and the muscle fiber conversion in muscles to enhance endurance. Muscles have fatty acid catabolism muscle fiber (Type I) that enhances endurance and glycoclastic muscle fiber (Type that enhances power. Fatty acid catabolism muscle fiber (Type I) which is responsible for enhancing endurance is red because it has plenty of mitochondria and myoglobin. In the meantime, glycoclastic muscle fiber (Type II) which is responsible for enhancing power is white. When PPARδ was artificially over-expressed in the rat muscles, Type I muscle fiber was increased significantly, in addition to the increase of myoglobin, electron transport system enzymes (cytochrome c, cytochrome c oxidases II and IV) and fatty acid β oxidase. Therefore, constant running time and distance were respectively 67% and 92% increased, compared with wild type rats (PLoS Biology, 2004, 2:e294).

Synthetic PPARδ ligands developed so far have less selectivity, compared with other PPARα and PPARγ ligands. The early selective ligand was L-631033, developed by Merk (*J. Steroid Biochem. Mol. Biol.* 1997, 63, p 1-8), which was produced by introducing a functional group being able to fix side chain based on its natural fatty acid morphology. The same research team reported later more effective ligand L-165041 (*J. Med. Chem.* 1996, 39, p 2629-2654), in which the compound known as a leukotriene agonist is functioning to activate human PPARδ. This compound exhibited great selectivity to hPPARδ, which is 10 times the selectivity to PPARα or PPARγ. And EC$_{50}$ of the compound was 530 nM. Other ligands L-796449 and L-783483 have improved affinity (EC$_{50}$=7.9 nM) but barely have selectivity to other hPPAR subtypes.

The PPARδ selective ligand GW501516 ([2-methyl-4-[[[4-methyl-2-[4-(trifluoromethyl)phenyl]-1,3-thiazol-5-yl]methyl]sulfanyl]phenoxy]acetic acid), developed by GlaxoSmithKline, exhibits much better physiological effect than any other ligands previously developed (*Proc. Natl. Acad. Sci. USA* 2001, 98, p 5306-5311).

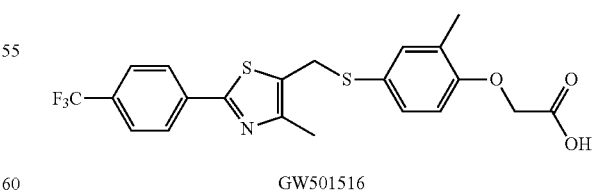

GW501516

The GW501516 has excellent affinity (1-10 nM) to PPARδ, and excellent selectivity to PPARα or PPARγ as well, which is at least 1000 times the selectivity of earlier ligands.

The thiazole compound represented by formula A as a PPARδ selective activator has been described in WO 2001-

00603 and WO 2002-62774 applied by Glaxo group and WO 2003-072100 applied by Eli Lilly.

formula A

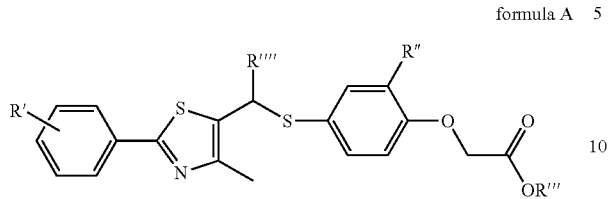

[Wherein, R' is $CF_3$ or F, R'' is H, $CH_3$ or Cl, R''' is H, $CH_3$ or $CH_2CH_3$, and R'''' is H, alkyl or aryl alkyl.]

However, the PPARδ activity induced by all the ligands developed so far is only resulted from 30-40% of total ligand-binding pockets.

DISCLOSURE

Technical Problem

It is an object of the present invention to provide a novel compound having high PPAR selectivity and a pharmaceutical composition, a cosmetic composition, an strengthening agent, a memory improving agent, a therapeutic agent for dementia and Parkinson's disease, a functional food and a feed composition containing the same.

Technical Solution

The present invention relates to the compound represented by formula (I) having activity to peroxisome proliferator activated receptor PPAR (referred as 'PPAR' hereinafter), and a hydrate, a solvate, a stereoisomer and a pharmaceutically acceptable salt thereof, a preparing method of the same, and a pharmaceutical composition, a cosmetic composition, an strengthening agent, a memory improving agent, a therapeutic agent for dementia and Parkinson's disease, a functional food and a feed composition containing the same.

[Formula I]

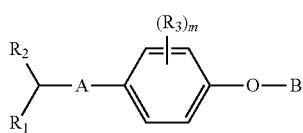

[Wherein, A is S or Se; B is H or

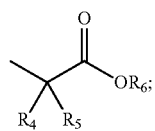

$R_1$ is aryl selected from the following structures;

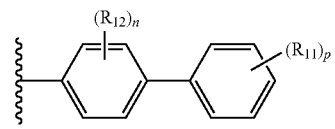

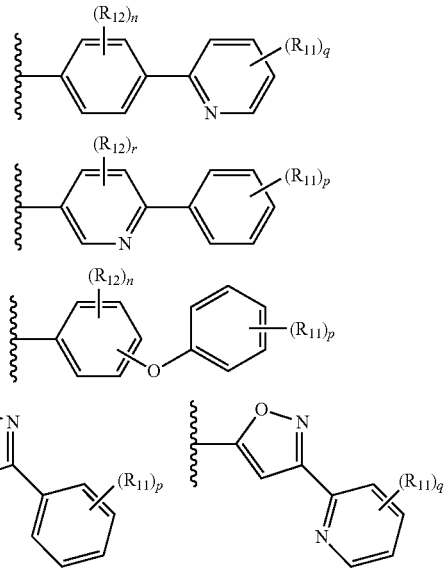

$R_2$ is H, C1-C8 alkyl or

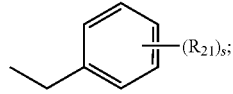

$R_3$ is H, C1-C8 alkyl or halogen; $R_4$ and $R_5$ are independently H, C1-C8 alkyl; $R_6$ is H, C1-C8 alkyl, C2-C7 alkenyl, alkali metal or alkali earth metal; $R_{11}$ and $R_{12}$ are independently H, C1-C8 alkyl or halogen; $R_{21}$ is H, halogen, C1-C7 alkyl, heterocyclic group or C1-C7 alkoxy; m and n are independently integers of 1-4; p is an integer of 1-5; q is an integer of 1-4; r is an integer of 1-3; s is an integer of 1-5; and alkyl and alkoxy of $R_2$, $R_3$, $R_4$, $R_5$, $R_6$, $R_{11}$, $R_{12}$ and $R_{21}$ can be substituted with one or more halogens or C1-C5 alkylamine. However, the case that $R_2$ is H and A is S is excluded.]

Particularly, $R_1$ of the aryl compound represented by formula (I) having activity to peroxisome proliferator activated receptor (PPAR) is preferably aryl selected from the following structures;

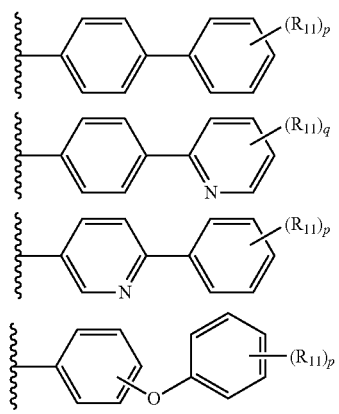

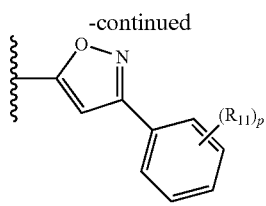

$R_2$ is C1-C8 alkyl substituted or non-substituted with halogen or

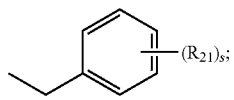

$R_3$ is C1-C5 alkyl substituted or non-substituted with halogen or halogen; $R_4$ and $R_5$ are independently H or C1-C5 alkyl substituted or non-substituted with halogen; $R_6$ is H, C1-C7 alkyl, alkali metal or alkali earth metal; $R_{11}$ and $R_{12}$ are independently H, C1-C5 alkyl substituted with one or more fluorines or fluorine; $R_{21}$ is H, halogen, C1-C5 alkyl substituted or non-substituted with halogen or C1-C5 alkoxy substituted or non-substituted with halogen; p is an integer of 1-5; q is an integer of 1-4; and s is an integer of 1-5.

$R_2$ of the compound represented by formula (I) can be further substituted with methyl, ethyl, n-propyl, i-propyl, n-butyl, i-butyl or t-butyl and benzyl of $R_2$ can be further substituted with fluorine, chlorine, methyl, ethyl, n-propyl, i-propyl, t-butyl, fluoromethyl, difluoromethyl, trifluoromethyl, 2-fluoroethyl, pentafluoroethyl, methoxy, ethoxy, propoxy, n-butoxy, t-butoxy, fluoromethoxy, difluoromethoxy, trifluoromethoxy, 2-fluoroethoxy and pentafluoroethoxy;

$R_3$ is H, methyl, ethyl, n-propyl, i-propyl, n-butyl, t-butyl, n-pentyl, 2-ethylhexyl, fluoromethyl, difluoromethyl, trifluoromethyl, 2-fluoroethyl, pentafluoroethyl, fluorine or chlorine;

$R_4$ and $R_5$ are independently H, methyl, ethyl, n-propyl, i-propyl, n-butyl, t-butyl, n-pentyl, 2-ethylhexyl, fluoromethyl, difluoromethyl, trifluoromethyl, 2-fluoroethyl or pentafluoroethyl;

$R_6$ is H, methyl, ethyl, n-propyl, i-propyl, n-butyl, t-butyl, n-pentyl, 2-ethylhexyl, fluoromethyl, difluoromethyl, trifluoromethyl, 2-fluoroethyl, pentafluoroethyl, ethenyl, 2-propenyl, 2-butenyl, 3-butenyl, $Li^+$, $Na^+$, $K^+$, $Ca^{2+}$, or $Mg^{2+}$;

$R_{11}$ and $R_{12}$ are independently H, methyl, ethyl, n-propyl, i-propyl, n-butyl, t-butyl, n-pentyl, 2-ethylhexyl, fluoromethyl, difluoromethyl, trifluoromethyl, 2-fluoroethyl, pentafluoroethyl, fluorine or chlorine.

The novel compound of the present invention can be prepared by the following reaction formula.

[Reaction Formula 1]

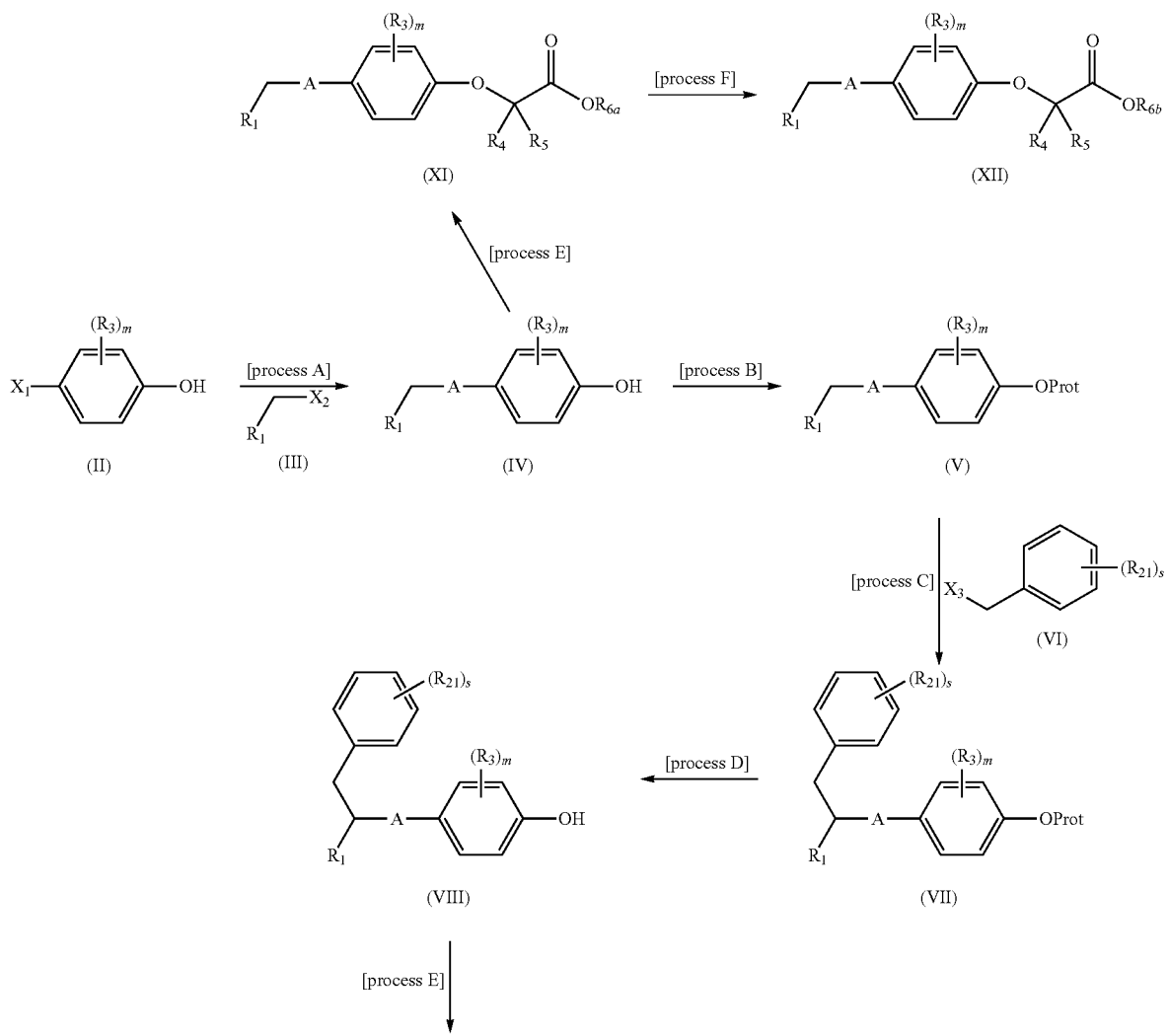

-continued

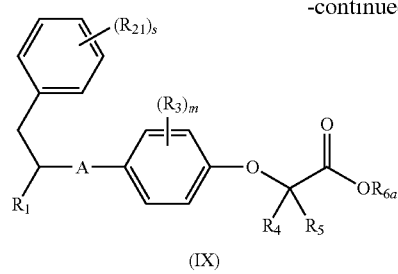

(IX)

[process F]

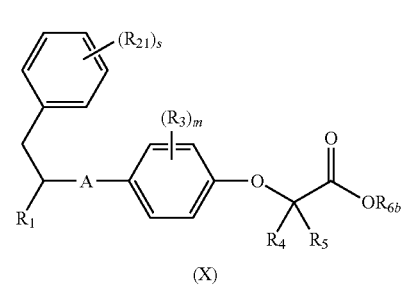

(X)

[Wherein, A is S or Se; B is H or

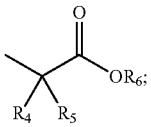

$R_1$ is aryl selected from the following structures;

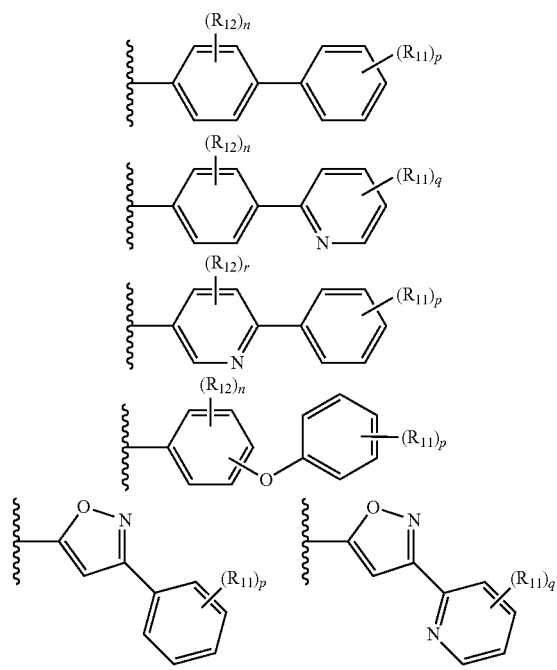

$R_2$ is H, C1-C8 alkyl or

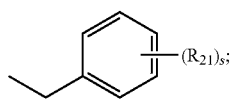

$R_3$ is H, C1-C8 alkyl or halogen; $R_4$ and $R_5$ are independently H or C1-C8 alkyl; $R_6$ is H, C1-C8 alkyl, C2-C7 alkenyl, alkali metal ($Li^+$, $Na^+$, $K^+$) or alkali earth metal ($Ca^{2+}$, $Mg^{2+}$); $R_{11}$ and $R_{12}$ are independently H, C1-C8 alkyl or halogen; $R_{21}$ is H, halogen, C1-C7 alkyl, heterocyclic group or C1-C7 alkoxy.

Prot herein is phenol protecting group, which can be C1-C4 lower alkyl, allyl, alkylsilyl, alkylarylsilyl or tetrahydropyranyl; alkyl and alkoxy of $R_2$, $R_3$, $R_4$, $R_5$, $R_6$, $R_{11}$, $R_{12}$ and $R_{21}$ can be substituted with one or more halogens or C1-C5 alkylamine; m and n are independently integers of 1-4; p is an integer of 1-5; q is an integer of 1-4; r is an integer of 1-3; s is an integer of 1-5; $X_1$ is bromine atom or iodine atom; $X_2$ and $X_3$ are independently chlorine atom, bromine atom, iodine atom or leaving group having reactivity with nucleophilic substitution. However, the case that $R_2$ is H and A is S is excluded.]

Hereinafter, the preparing method of the invention is described in detail.

[Process A] Preparation of the Compound Represented by Formula (IV)

To prepare the compound represented by formula (IV), the compound represented by formula (II) was treated with Grignard reagent to protect phenol group, without independent separation process, and reacted with organic metal reagent and S or Se stepwise, and finally reacted with the compound represented by formula (III). This process has 4 sub-reaction stages performed in a row.

The sub-reaction stages are described in detail hereinafter.

[Protection of Phenol Group with Grignard Reagent]

The anhydride solvent used in this process is selected from the group consisting of such single solvents as diethylether, tetrahydrofuran, hexane and heptane and mixed solvents comprising at least two of these solvents. It is more preferred to select diethylether, tetrahydrofuran or the mixed solvent comprising diethylether and tetrahydrofuran as the anhydride solvent. And it is most preferred to select a polar solvent, which can be tetrahydrofuran.

Grignard reagent used herein can be selected from the group consisting of methyl, ethyl, n-propyl, iso-propyl, n-butyl, sec-butylmagnesiumchloride ($R_2MgCl$) and alkylmagnesiumbromide ($R_2MgBr$). Among these, iso-propylmagnesiumchloride (($CH_3$)$_2CHMgCl$) is most preferred.

The reaction temperature depends on a solvent, but it is generally set at −20~40° C. and preferably at 0° C.~room temperature (25° C.). The reaction time depends on the reaction temperature and a solvent, but it is generally 10-60 minutes and preferably 10-30 minutes.

[Halogen-Lithium Substitution and S or Se Introduction]

The organic metal reagent used for halogen-lithium substitution can be selected from the group consisting of n-butyl lithium, sec-butyl lithium and tert-butyl lithium. Among these compounds, tert-butyl lithium is most preferred.

S or Se with fine particles is preferred, which is added as dissolved in anhydride tetrahydrofuran or added directly.

The reaction temperature depends on a solvent, but is generally set at −78~25° C. The reaction temperature for halogen-metal substitution is preferably −75° C. and the temperature for S or Se introduction is −75~room temperature (25°

C.). The halogen-metal substitution reaction takes 10-30 minutes and the S or Se introduction reaction takes 30-120 minutes.

[Addition of the Compound Represented by Formula (III)]

To prepare the compound represented by formula (III) used in this process, Suzuki coupling reaction is induced using the conventional palladium catalyst, and halogenation follows. Halogen of the compound represented by formula (III) is selected from the group consisting of chlorine, bromine and iodine. And among these, chlorine is most preferred.

The reaction temperature depends on a solvent, but it is generally set at −78~25° C., more preferably at 0~10° C. The reaction time is generally 10-120 minutes and preferably 10-60 minutes.

[Process B] Preparation of the Compound Represented by Formula (V)

To prepare the compound represented by formula (V), the compound represented by formula (IV) is preferably reacted with the compound generally used as phenol protecting group in the presence of base.

The phenol protecting group is exemplified by C1-C4 lower alkyl, allyl, alkylsilyl such as trimethylsilyl, tert-butyldiphenylsilyl, triisopropylsilyl and tert-butyldimethylsilyl, alkylarylsilyl and tetrahydropyranyl. Among these compounds, tert-butyl group, tetrahydropyranyl group and silyl group are preferred.

The aprotic polar solvent used in this process is selected from the group consisting of N,N-dimethylformamide, N,N-dimethylacetamide, dimethylsilfoxide, acetonitrile, acetone, ethylacetate, carbon tetrachloride, chloroform and dichloromethane. The ether herein can be selected from the group consisting of tetrahydrofuran, dioxane, dimethoxyethane, diethyleneglycoldimethylether and triethyleneglycoldimethylether. The aromatic hydrocarbon is exemplified by benzene, toluene and xylene. As a solvent herein, the aprotic polar solvent is preferred and particularly N,N-dimethylformamide, chloroform or dichloromethane is more preferred.

The base herein is amine including pyridine, triethylamine, imidazole, N,N-dimethylaminopyridine. For the reaction of alkyl or allyl etherified protecting group, such bases as sodium hydroxide, potassium hydroxide, sodium carbonate and potassium carbonate are used. In particular, imidazole and potassium carbonate are more preferred.

The tetrahydropyranyl protecting group is obtained by catalytic reaction of 3,4-dihydro-2H-pyran with alkyl or allyltriphenylphosphonium bromide.

The reaction temperature depends on a solvent, but it is generally set at −10~80° C., more preferably at 0~room temperature (25° C.). The reaction time depends on the reaction temperature and a solvent, but generally it takes from one hour to one day. It is more preferred to finish the reaction within 4 hours.

[Process C] Preparation of the Compound Represented by Formula (VII)

To prepare the compound represented by formula (VII), α-proton of thio or selenoether of the compound represented by formula (V) is treated with a strong alkali to give a nucleophile, which is reacted with various electrophiles.

The anhydride solvent used in this process is selected from the group consisting of such single solvents as diethylether, tetrahydrofuran, hexane and heptane and mixed solvents comprising at least two of these solvents. It is more preferred to select diethylether, tetrahydrofuran or the mixed solvent comprising diethylether and tetrahydrofuran as the anhydride solvent.

The strong alkali used for the α-proton extraction is selected from the group consisting of potassium tert-butoxide (t-BuOK), lithium diisopropyl amide (LDA), n-butyl lithium, sec-butyl lithium and tert-butyl lithium, and among these compounds, lithium diisopropyl amide (LDA) is most preferred.

The electrophile reacted with the nucleophile of thio or selenoether is any compound that can be easily obtained by the conventional method known to those in the art or easily produced according to the methods described in references, which is exemplified by those compounds harboring highly reactive halogen, aldehyde or ketone group and is either dissolved in an anhydride solvent for the addition or added directly for the reaction.

The reaction temperature depends on a solvent but is generally −78~25° C. It is more preferred to perform the α-proton extraction reaction in the presence of a strong alkali at −75° C. at which electrophile is added. Then, the temperature is raised slowly to room temperature (25° C.). The reaction time differs from each reaction stage. For example, the α-proton extraction by a strong alkali takes 10-30 minutes and the reaction with electrophile takes 30-90 minutes.

[Process D] Preparation of the Compound Represented by Formula (VIII)

The compound represented by formula (VIII) is obtained by eliminating the phenol protecting group from the compound represented by formula (VII).

The polar solvent used in this process is selected from the group consisting of N,N-dimethylformamide, N,N-dimethylacetamide, dimethylsilfoxide, acetonitrile, acetone, ethylacetate, carbon tetrachloride, chloroform and dichloromethane. The ether herein can be selected from the group consisting of tetrahydrofuran, dioxane, dimethoxyethane and diethyleneglycoldimethylether. The alcohol can be methanol or ethanol. The aromatic hydrocarbon is exemplified by benzene, toluene and xylene. As a solvent herein, the polar solvent is preferred and particularly tetrahydrofuran is more preferred.

To eliminate the phenol protecting group, particularly to eliminate methyl, ethyl, tert-butyl, benzyl or allylether protecting group, trimethylsilyliodide, ethanethioalcoholsodium salt, lithiumiodide, aluminum halide, boron halide or Lewis acid such as trifluoroacetate is used, and to eliminate the silyl protecting group such as trimethylsilyl, tert-butyldiphenylsilyl, triisopropylsilyl and tert-butyldimethylsilyl, fluoride such as tetrabutylammoniumfluorine ($Bu_4N^+F^-$), halogen acid (hydrofluoric acid, hydrochloric acid, hydrobromic acid or hydroiodic acid) or potassium fluoride is used.

It is preferred to use fluoride to eliminate the silyl protecting group and is more preferred to use tetrabutylammoniumfluorine.

The reaction temperature depends on a method and a solvent but is generally 0~120° C. and preferably 10~25° C. The reaction time depends on the reaction temperature, but generally it takes from 30 minutes to one day. It is more preferred to finish the reaction within 2 hours.

[Process E] Preparation of the Compound Represented by Formula (IX)

To prepare the compound represented by formula (IX), the compound represented by formula (VIII) is preferably reacted with halogenacetate alkylester or alkylhalogenacetate alkylester in the presence of base.

The halogenacetate alkylester or alkylhalogenacetate alkylester is the general compound that can be easily obtained. Among the alkylhalogenacetate alkylesters, the compound that can not be easily obtained is prepared by bromination of alkylacetate alkylester. The halogen herein is exemplified by chlorine atom, bromine atom and iodine atom.

The solvent used in this process can be a soluble single solvent selected from the group consisting of N,N-dimethylformamide, N,N-dimethylacetamide, dimethylsulfoxide, acetonitrile, acetone, ethanol and methanol or a mixed solvent prepared by mixing these compounds with 1-10% water. The most preferred solvent is a mixed solvent prepared by mixing acetone or dimethylsulfoxide with 1-5% water.

The base used in this process is not limited as long as it does not have a bad influence on the reaction, regardless of strong or weak, which is exemplified by alkali metal hydride such as sodium hydride and lithium hydride, alkali earth metal hydride such as potassium hydride, alkali metal hydroxide such as sodium hydroxide and potassium hydroxide, and alkali metal carbonate such as lithium carbonate, potassium carbonate, potassium bicarbonate and cesium carbonate. Among these compounds, alkali metal carbonate is preferred, and potassium carbonate is more preferred.

The reaction temperature is not limited but up to the boiling point of a solvent. However, high temperature is not preferred to inhibit side reactions. The preferable reaction temperature is 0~90° C. The reaction time differs from the reaction temperature but is generally 30 minutes-1 day and preferably 30-120 minutes.

[Process F-1] Preparation of the Compound Represented by Formula (X)

To prepare the compound represented by formula (X), carboxylic acid ester of the compound represented by formula (IX) is hydrolyzed in the mixed solution of soluble inorganic salt and alcohol. Or hydrolysis of ester is performed in the mixed solution comprising the compound represented by formula (IX), 2.0 M of lithium hydroxide, THF and water.

The solvent used in this process is a soluble solvent that can be mixed with water, for example alcohols such as methanol and ethanol.

The base used in this process is an aqueous solution prepared by mixing alkali metal hydroxide such as lithium hydroxide, sodium hydroxide and potassium hydroxide with water at the concentration of 0.1-3 N, considering the type of carboxylic acid alkali salt. The acid used to obtain the compound represented by formula (X) as a carboxylic acid form is preferably acetic acid aqueous solution, sodium hydrogen sulfate ($NaHSO_4$) aqueous solution or 0.1-3 N hydrochloric acid aqueous solution, and 0.5 M $NaHSO_4$ is more preferred.

The reaction is preferably performed at a low temperature in order to inhibit side reactions, which is generally 0° C.—room temperature. The reaction time depends on the reaction temperature but is generally 10 minutes-3 hours and more preferably 30 minutes-1 hour. When 2.0 M of lithium hydroxide is reacted in the mixed solution of THF and water, the preferable reaction temperature is 0□ and the preferable reaction time is 1-2 hours.

[Process F-2] Preparation of the Compound Represented by Formula (X)

The compound represented by formula (X) is prepared by allyl ester salt substitution from the compound represented by formula (IX) using alkali metal salt or alkali earth metal salt of 2-ethylhexanoate and a metal catalyst in an organic solvent.

The solvent used in this process is an anhydride organic solvent selected from the group consisting of chloroform, dichloromethane and ethylacetate.

The metal catalyst used in this process is paladiumtetrakistriphenylphosphine and the preferable content thereof is 0.01-0.1 equivalent.

The reaction is preferably performed at a low temperature in order to inhibit side reactions, which is generally 0□-room temperature. The reaction time depends on the reaction temperature but is generally 10 minutes-3 hours and more preferably 30 minutes-1 hour.

Such salt compound can be easily separated by centrifugation or ion exchange resin. The obtained metal salt compound of formula (X) is much easier to separate than the salt compound prepared by process F-1 (hydrolysis).

The resultant Y type compound of formula (I) is a very important material as a PPAR protein ligand. This compound contains chiral carbon, suggesting that it also includes stereoisomer thereof. The present invention includes the aryl compound represented by formula (I) and a hydrate, a solvate, a stereoisomer and a pharmaceutically acceptable salt thereof.

The aryl compound represented by formula (I) and a hydrate, a solvate, a stereoisomer and a pharmaceutically acceptable salt thereof of the present invention can be effectively used as a composition for PPAR activator. The aryl compound represented by formula (I) and a hydrate, a solvate, a stereoisomer and a pharmaceutically acceptable salt thereof of the present invention can activate PPAR, so that they can be effectively used as a pharmaceutical composition for the prevention and treatment of arteriosclerosis, hyperlipidemia, obesity, diabetes, dementia or Parkinson's disease and for lowering cholesterol, for strengthening muscles, for improving endurance and memory, and as a composition for functional food and beverages, food additives, functional cosmetic and animal feeds.

The aryl compound represented by formula (I) and a hydrate, a solvate, a stereoisomer and a pharmaceutically acceptable salt thereof of the present invention can be used for the functional cosmetic composition for prevention and improvement of obesity and for the functional cosmetic composition for strengthening muscle and enhancing endurance. The functional cosmetic composition for strengthening muscle and enhancing endurance can be formulated as ointment, lotion or cream to be applied on the body part before/after exercise and can be used for a long term to bring the wanted effect. The aryl compound represented by formula (I) and a hydrate, a solvate, a stereoisomer and a pharmaceutically acceptable salt thereof of the present invention can be formulated as ointment and be applied on the body part to prevent or treat diabetes or diabetic foot ulcer, so-called diabetic ulcer.

The present invention provides a pharmaceutical composition, a functional food adjuvant, a functional drink, a food additive and a feed composition for the prevention and treatment of arteriosclerosis, dementia and Parkinson's disease, for strengthening muscle, for enhancing endurance or for improving memory containing the PPAR activator as an active ingredient.

The present invention also provides a screening method of an activator for the prevention and treatment of arteriosclerosis, dementia and Parkinson's disease, strengthening muscle, enhancing endurance and improving memory, which comprises the steps of adding a PPAR activator candidate to PPAR; and measuring the activity of PPAR.

The pharmaceutically acceptable salt herein includes all the pharmaceutically acceptable organic salts that are able to form salt with carboxylic acid of the compound of formula (I) and inorganic salts such as alkali metal ions and alkali earth metal ions, which are exemplified by $Li^+$, $Na^+$, $K^+$, $Ca^{2+}$ and $Mg^{2+}$.

The therapeutic effective dose of the compound represented by formula (I) and a hydrate, a solvate, a stereoisomer and a pharmaceutically acceptable salt thereof of the present invention can be determined according to the type of compound, administration method, target subject and target disease but is determined based on the conventional medicinal standard. The preferable dose of the compound represented by formula (I) is 1-100 mg/kg (body weight)/day. The administration frequency can be once or several times a day within the allowed one day dosage. The composition of the present invention can be administered orally or parenterally and be used in general forms of pharmaceutical formulation. For example, the composition of the present invention can be formulated as tablets, powders, dried syrups, chewable tablets, granules, capsules, soft capsules, pills, drinks, sublinguals, etc. The tablets of the present invention can be administered to a subject by a method or pathway that delivers the effective dose of the tablet with bioavailability, which is oral pathway. And the administration method or pathway can be determined according to the characteristics, stages of the target disease and other conditions. When the composition of the present invention is formed as tablets, it can additionally include pharmaceutically acceptable excipients. The content and characteristics of the excipient can be determined by the solubility and chemical properties of the selected tablet, administration pathway and standard pharmaceutical practice.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Compound S1

[Process A]

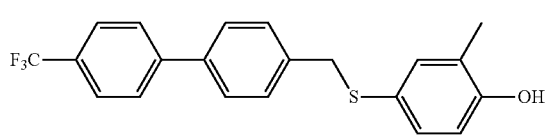

468 mg (2 mmol) of 4-iodo-2-methylphenol was dissolved in 20 ml of anhydride tetrahydrofuran in the presence of nitrogen and at that time temperature was maintained at 0° C. 1.5 ml of isopropylmagnesiumchloride (2M) was slowly added thereto, followed by reaction for 10 minutes. The reaction solution was cooled down to −78° C., to which 2.00 ml of tert-butyl lithium (1.7 M-hexane solution, 1.0 equivalent) was slowly added. After stirring for 10 minutes, 64 mg (2 mmol, 1.0 equivalent) of solid S was added thereto at the same temperature at a time. The reaction continued for 40 minutes with raising the temperature up to 15° C. 541 mg (2 mmol, 1.0 equivalent) of 4-chloromethyl-4'-trifluoromethyl-biphenyl of formula (III) was dissolved in 10 ml of anhydride THF, which was slowly added thereto at the same temperature. After one more hour of reaction, the reaction was terminated by ammonium chloride solution, and the organic solvent was extracted by using ethylacetate and sodium chloride solution, which was dried over magnesium sulfate to eliminate moisture of the organic layer. After filtering, the solvent was distilled under reduced pressure, and the residue was purified by silica gel column chromatography to give 630 mg (yield: 84%) of the target compound.

$^1$H NMR (300 MHz, CDCl$_3$) δ7.67 (s, 4H), 67.50 (d, 2H), 67.28 (t, 2H), 67.13 (s, 1H), 67.07 (q, 1H), 66.68 (d, 1H) 65.20 (s, 1H), 64.02 (s, 2H), 62.17 (s, 3H)

Example 2

Preparation of Compound S2

[Process B]

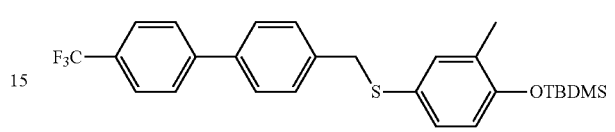

748 mg (2 mmol) of the compound S1 and 290 mg (2.0 equivalent) of imidazole were completely dissolved in 20 ml of dimethylformamide. 165 mg (1.1 equivalent) of tert-butyldimethylsilylchloride was slowly added thereto, followed by stirring at room temperature for 4 hours. Upon completion of the reaction, the organic solvent was extracted by using ammonium chloride solution and ethylacetate. Moisture of the organic layer was dried over magnesium sulfate. Silica gel column was used to purify and the solvent was distilled under reduced pressure to give 928 mg (yield: 95%) of the target compound.

$^1$H NMR (300 MHz, CDCl$_3$) δ7.67 (s, 4H), 67.50 (d, 2H), 67.27 (t, 2H), 67.13 (s, 1H), 67.05 (q, 1H), 66.66 (d, 1H), 64.04 (s, 2H), 62.15 (s, 3H), 61.01 (s, 9H), 60.20 (s, 6H).

Example 3

Preparation of Compound S3

[Process C]

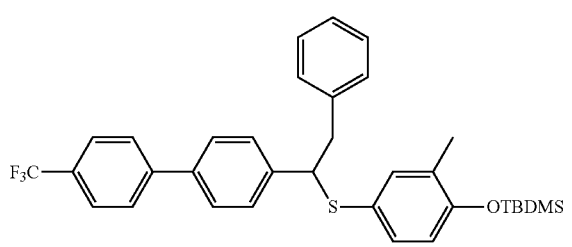

977 mg (2 mmol) of the compound S2 was dissolved in 20 ml of anhydride tetrahydrofuran and the temperature was lowered to −78° C. 3.6 ml (1.8 M, 2.0 equivalent) of lithium diisopropyl amide (LDA) was slowly added thereto. Then, 274 μl (2.0 mmol) of benzylbromide was added to the reaction solution, and the temperature was slowly raised to room temperature. After 30 more minutes of reaction, the reaction was terminated by ammonium chloride solution, and the organic solvent was extracted by using ethylacetate and sodium chloride solution, which was dried over magnesium sulfate to eliminate moisture of the organic layer. After filtering, the solvent was distilled under reduced pressure, and the residue proceeded to silica gel column chromatography to give 961 mg (yield: 83%) of the target compound.

$^1$H NMR (300 MHz, CDCl$_3$) δ7.67 (s, 4H), 67.47-7.05 (m, 11H), 66.63 (d, 1H), 64.30 (m, 1H), 63.54 (m, 1H), 63.24 (m, 1H), 62.12 (s, 3H), 61.01 (s, 9H), 60.21 (s, 6H).

Example 4

Preparation of Compound S4

[Process C]

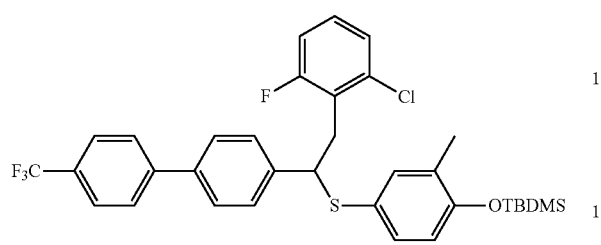

S4

489 mg (1 mmol) of the compound S2 was dissolved in 20 ml of anhydride tetrahydrofuran and the temperature was lowered to −78° C. 1.8 ml (1.8 M, 2.0 equivalent) of lithium diisopropyl amide (LDA) was slowly added thereto. Then, 270 μl (2.0 mmol) of 2-chloro-5-fluorobenzylbromide was added to the reaction solution, and the temperature was slowly raised to room temperature. After 30 more minutes of reaction, the reaction was terminated by ammonium chloride solution, and the organic solvent was extracted by using ethylacetate and sodium chloride solution, which was dried over magnesium sulfate to eliminate moisture of the organic layer. After filtering, the solvent was distilled under reduced pressure, and the residue proceeded to silica gel column chromatography to give 523 mg (yield: 83%) of the target compound.

$^1$H NMR (300 MHz, CDCl$_3$) δ7.66 (s, 4H), δ7.45 (d, 2H), δ7.31 (d, 2H), δ7.08 (m, 4H), δ6.85 (m, 1H), δ6.60 (d, 1H), δ4.50 (t, 1H), δ3.41 (d, 2H), δ2.11 (s, 3H), δ1.01 (s, 9H), δ0.20 (s, 6H).

Example 5

Preparation of Compound S5

[Process C]

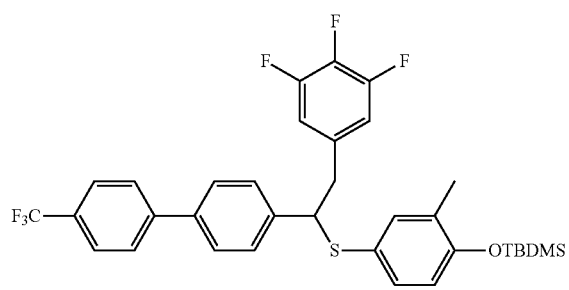

S5

489 mg (1 mmol) of the compound S2 was dissolved in 20 ml of anhydride tetrahydrofuran and the temperature was lowered to −78° C. 1.8 ml (1.8 M, 2.0 equivalent) of lithium diisopropyl amide (LDA) was slowly added thereto. Then, 282 μl (2.0 mmol) of 3,4,5-trifluorobenzylbromide was added to the reaction solution, and the temperature was slowly raised to room temperature. After 30 more minutes of reaction, the reaction was terminated by ammonium chloride solution, and the organic solvent was extracted by using ethylacetate and sodium chloride solution, which was dried over magnesium sulfate to eliminate moisture of the organic layer. After filtering, the solvent was distilled under reduced pressure, and the residue proceeded to silica gel column chromatography to give 518 mg (yield: 82%) of the target compound.

$^1$H NMR (300 MHz, CDCl$_3$) δ7.74 (q, 2H), δ7.14 (m, 4H), δ7.03 (d, 1H), δ6.79 (t, 4H), δ6.61 (q, 1H), δ6.41 (d, 1H), δ4.39 (t, 1H), δ3.26 (d, 2H), δ2.14 (s, 3H), δ1.01 (s, 9H), δ0.20 (s, 6H).

Example 6

Preparation of Compound S6

[Process C]

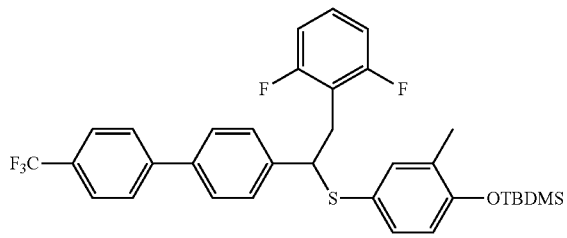

S6

489 mg (1 mmol) of the compound S2 was dissolved in 20 ml of anhydride tetrahydrofuran and the temperature was lowered to −78° C. 1.8 ml (1.8 M, 2.0 equivalent) of lithium diisopropyl amide (LDA) was slowly added thereto. Then, 259 μl (2.0 mmol) of 2,5-difluorobenzylbromide was added to the reaction solution, and the temperature was slowly raised to room temperature. After 30 more minutes of reaction, the reaction was terminated by ammonium chloride solution, and the organic solvent was extracted by using ethylacetate and sodium chloride solution, which was dried over magnesium sulfate to eliminate moisture of the organic layer. After filtering, the solvent was distilled under reduced pressure, and the residue proceeded to silica gel column chromatography to give 503 mg (yield: 82%) of the target compound.

$^1$H NMR (300 MHz, CDCl$_3$) δ7.67 (s, 4H), δ7.45 (d, 2H), δ7.30 (d, 2H), δ7.09 (m, 4H), δ6.75 (m, 1H), δ6.54 (m, 1H), δ4.44 (t, 1H), δ3.35 (m, 2H), δ2.19 (s, 3H), 1.01 (s, 9H), δ0.20 (s, 6H).

Example 7

Preparation of Compound S7

[Process C]

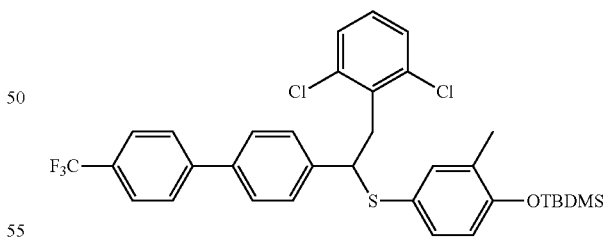

S7

489 mg (1 mmol) of the compound S2 was dissolved in 20 ml of anhydride tetrahydrofuran and the temperature was lowered to −78° C. 1.8 ml (1.8 M, 2.0 equivalent) of lithium diisopropyl amide (LDA) was slowly added thereto. Then, 300 μl (2.0 mmol) of 2,5-dichlorobenzylbromide was added to the reaction solution, and the temperature was slowly raised to room temperature. After 30 more minutes of reaction, the reaction was terminated by ammonium chloride solution, and the organic solvent was extracted by using ethylacetate and sodium chloride solution, which was dried over magnesium sulfate to eliminate moisture of the organic layer. After filtering, the solvent was distilled under reduced pressure, and the residue was purified by silica gel column chromatography to give 531 mg (yield: 82%) of the target compound.

$^1$H NMR (300 MHz, CDCl$_3$) δ7.66 (s, 4H), 67.45 (d, 2H), 67.33 (d, 2H), 67.08 (m, 2H), 67.05 (m, 3H), 66.52 (d, 1H), 64.61 (q, 1H), 63.58 (m, 2H), 62.19 (s, 3H), 1.01 (s, 9H), 60.20 (s, 6H).

Example 8

Preparation of Compound S8

[Process C]

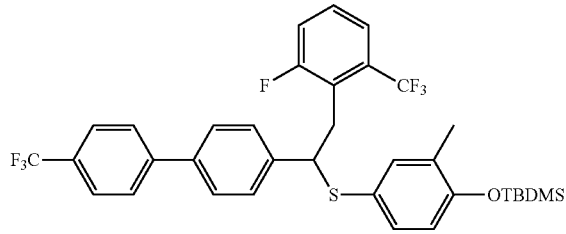

S8

489 mg (1 mmol) of the compound S2 was dissolved in 20 ml of anhydride tetrahydrofuran and the temperature was lowered to −78° C. 1.8 ml (1.8 M, 2.0 equivalent) of lithium diisopropyl amide (LDA) was slowly added thereto. Then, 514 mg (2.0 mmol) of 2-chloro-5-trifluoromethylbenzylbromide was added to the reaction solution, and the temperature was slowly raised to room temperature. After 30 more minutes of reaction, the reaction was terminated by ammonium chloride solution, and the organic solvent was extracted by using ethylacetate and sodium chloride solution, which was dried over magnesium sulfate to eliminate moisture of the organic layer. After filtering, the solvent was distillated under reduced pressure, and the residue was purified by silica gel column chromatography to give 538 mg (yield: 81%) of the target compound (EIMS: 665.2[M+H]$^+$).

Example 9

Preparation of Compound S9

[Process D]

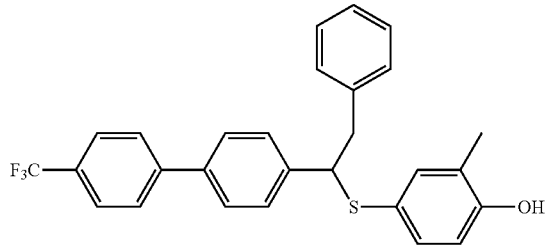

S9

1131 mg (2 mmol) of the compound S3 prepared in example 3 was completely dissolved in 20 ml of tetrahydrofuran. 5 ml (1M-tetrahydrofuran solution, 2.5 equivalent) of tetrabutylammoniumfluoride (TBAF) was slowly added thereto at room temperature. After 30 minutes of reaction, the organic solvent was extracted by using ammonium chloride solution and ethylacetate, which was dried over magnesium sulfate to eliminate moisture of the organic layer. After filtering, the solvent was distillated under reduced pressure, and the residue was purified by silica gel column chromatography to give 873 mg (yield: 94%) of the target compound.

$^1$H NMR (300 MHz, CDCl$_3$) δ7.67 (s, 4H), 67.47-7.05 (m, 11H), 66.63 (d, 1H), 64.30 (m, 1H), 63.54 (m, 1H), 63.24 (m, 1H), 62.14 (s, 3H).

Example 10

Preparation of Compound S10

[Process E]

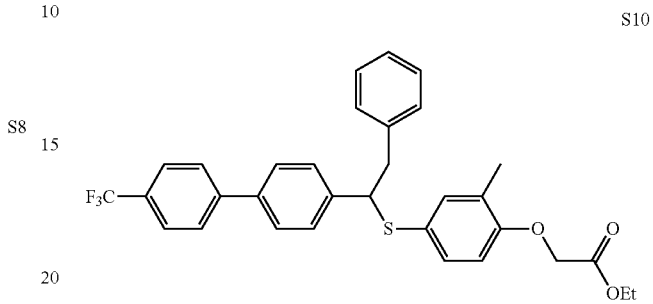

S10

465 mg (1 mmol) of the compound S9 prepared in example 9 was well mixed with 10 ml of acetone containing 5% water and 346 mg (2.5 mmol, 2.5 equivalent) of potassium carbonate at room temperature. 134 μl (1.2 mmol, 1.2 equivalent) of bromoacetateethylester was added thereto, followed by vigorous stirring for 4 hours. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 512 mg (yield: 93%) of the target compound.

$^1$H NMR (300 MHz, CDCl$_3$) δ7.67 (s, 4H), 67.45 (d, 2H), 67.22 (m, 5H), 67.05 (m, 4H), 66.54 (d, 1H), 64.59 (s, 2H), 64.26 (m, 3H), 63.24 (m, 2H), 62.18 (s, 3H), 61.27 (t, 3H).

Example 11

Preparation of Compound S11

[Process E]

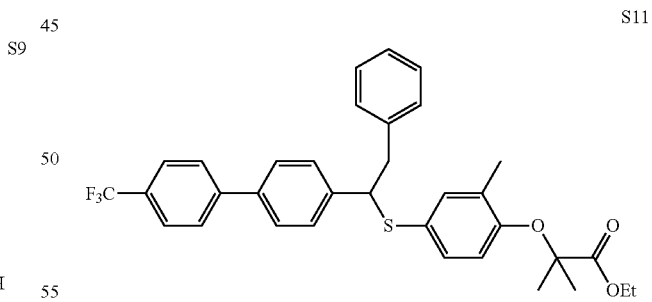

S11

465 mg (1 mmol) of the compound S9 prepared in example 9 was well mixed with 10 ml of acetone containing 5% water and 346 mg (2.5 mmol, 2.5 equivalent) of potassium carbonate at room temperature. 210 μl (1.2 mmol, 1.2 equivalent) of ethyl-2-bromo-2-methylpropanate was added thereto. The mixture was heated at 60~90° C. with supplementing acetone for 4 hours with stirring vigorously. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 463 mg (yield: 80%) of the target compound.

$^1$H NMR (300 MHz, CDCl$_3$) δ7.66 (s, 4H), δ7.43 (d, 2H), δ7.22 (m, 5H), δ7.03 (m, 4H), δ6.50 (d, 1H), δ4.28 (q, 1H), δ4.19 (m, 2H), δ2.12 (s, 3H), δ1.54 (s, 6H), δ1.19 (t, 3H).

Example 12

Preparation of Compound S12

[Process E]

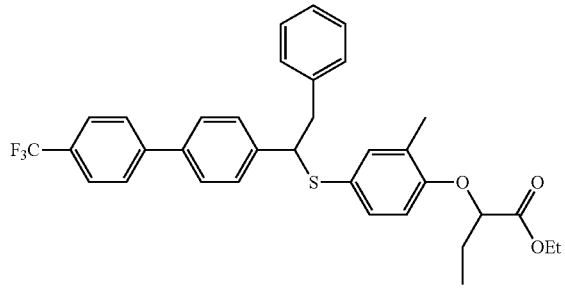

S12

465 mg (1 mmol) of the compound S9 prepared in example 9 was well mixed with 10 ml of acetone containing 5% water and 346 mg (2.5 mmol, 2.5 equivalent) of potassium carbonate at room temperature. 146 μl (1.2 mmol, 1.2 equivalent) of ethyl-2-bromobutylate was added thereto. The mixture was heated at 60~90° C. with supplementing acetone for 4 hours with stirring vigorously. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 470 mg (yield: 83%) of the target compound.

$^1$H NMR (300 MHz, CDCl$_3$) δ7.67 (s, 4H), δ7.46 (d, 2H), δ7.23 (m, 5H), δ7.03 (m, 4H), δ6.51 (d, 1H), δ4.53 (t, 1H), δ4.21 (m, 3H), δ3.27 (m, 2H), δ2.19 (s, 3H), δ1.99 (m, 2H), δ1.28 (t, 3H), δ1.09 (t, 3H).

Example 13

Preparation of Compound S13

[Process E]

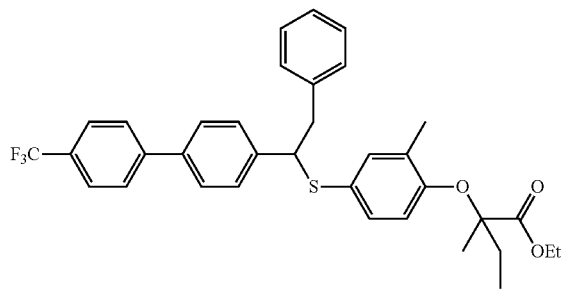

S13

465 mg (1 mmol) of the compound S9 prepared in example 9 was well mixed with 10 ml of acetone containing 5% water and 346 mg (2.5 mmol, 2.5 equivalent) of potassium carbonate at room temperature. 193 μl (1.2 mmol, 1.2 equivalent) of ethyl-2-bromo-2-methylbutylate was added thereto. The mixture was heated at 60~90° C. with supplementing acetone for 4 hours with stirring vigorously. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 474 mg (yield: 80%) of the target compound (EIMS: 593.2[M+H]$^+$).

Example 14

Preparation of Compound S14

[Process F]

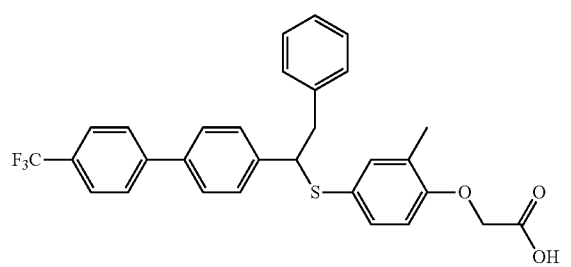

S14

550 mg (1 mmol) of the compound S10 prepared in example 10 was mixed well with 15 ml of THF and 10 ml of water, to which 0.6 ml of 2.0 M lithium hydroxide solution was slowly added at 0° C. After stirring at 0° C. for 60 minutes, 2.5 ml of 0.5 M NaHSO$_4$ was added thereto. The organic solvent was extracted by using sodium chloride solution and ethylacetate. After filtering, the solvent was distillated under reduced pressure, and the residue was purified by LH-20 column chromatography to give 512 mg (yield: 98%) of the target compound.

$^1$H NMR (300 MHz, CDCl$_3$) δ7.67 (s, 4H), δ7.45 (d, 2H), δ7.22 (m, 5H), δ7.05 (m, 4H), δ6.54 (d, 1H), δ4.59 (s, 2H), δ4.24 (m, 1H), δ3.24 (m, 2H), δ2.18 (s, 3H).

Example 15

Preparation of Compound S15

[Process E]

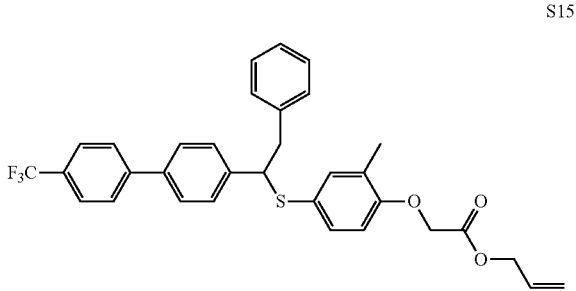

S15

465 mg (1 mmol) of the compound S9 prepared in example 9 was well mixed with 10 ml of acetone containing 5% water and 346 mg (2.5 mmol, 2.5 equivalent) of potassium carbonate at room temperature. 219 mg (1.2 mmol, 1.1 equivalent) of bromoacetateallylester was added thereto, followed by vigorous stirring for 4 hours. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 529 mg (yield: 94%) of the target compound (EIMS: 563.1[M+H]$^+$).

Example 16

Preparation of Compound S16

[Process F]

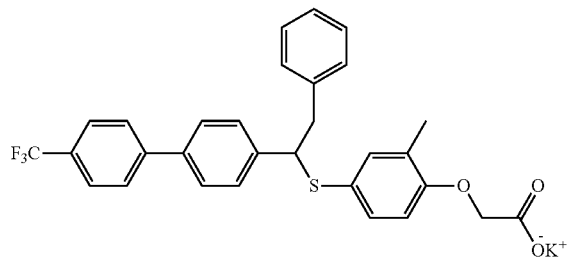

504 mg (1 mmol) of the compound S15 prepared in example and 56 mg (0.05 mmol, 0.05 equivalent) of palladiumtetrakistriphenylphosphine were dissolved in 20 ml of anhydride dichloromethane, followed by stirring at room temperature. 174 mg (1 mmol, 1.0 equivalent) of potassium 2-ethylhexanoate was dissolved in 2 ml of anhydride dichloromethane, which was slowly added to the reaction solution. After stirring at room temperature for one hour, centrifugation was performed to eliminate the solvent. The solid produced thereby was washed with 20 ml of dichloromethane and 20 ml of normal hexane, followed by drying to give 509 mg (yield: 91%) of the target compound.

$^1$H NMR (300 MHz, CDCl$_3$) δ7.67 (s, 4H), 67.45 (d, 2H), 67.22 (m, 5H), 67.05 (m, 4H), 66.54 (d, 1H), 64.59 (s, 2H), 64.24 (m, 1H), 63.24 (m, 2H), 62.18 (s, 3H).

Examples 17~150

The compounds shown in Table 1 were prepared by the methods of examples 1-16 and NMR of each compound is shown in Table 2.

TABLE 1

| Ex. | R$_1$ | R$_2$ | (R$_3$)$_m$ ring | m | R$_4$ | R$_5$ | R$_6$ | A |
|---|---|---|---|---|---|---|---|---|
| 17 | F$_3$C-biphenyl | 3-F, 3-Cl, 2-ethyl phenyl | 2-CH$_3$, 4-substituted phenyl | 1 | H | H | H | S |
| 18 | F$_3$C-biphenyl | 2,3-F, 5-ethyl phenyl | 2-CH$_3$, 4-substituted phenyl | 1 | H | H | H | S |
| 19 | F$_3$C-biphenyl | 2,6-F, 4-ethyl phenyl | 2-CH$_3$, 4-substituted phenyl | 1 | H | H | H | S |
| 20 | F$_3$C-biphenyl | 2,6-Cl, 4-ethyl phenyl | 2-CH$_3$, 4-substituted phenyl | 1 | H | H | H | S |

TABLE 1-continued

| Ex. | R₁ | R₂ | (R₃)ₘ ring | m | R₄ | R₅ | R₆ | A |
|---|---|---|---|---|---|---|---|---|
| 21 | 4'-(F₃C)-biphenyl-4-yl | 3-F, 2-ethyl, 1-CF₃ phenyl | 3,4-dimethylphenyl | 1 | H | H | H | S |
| 22 | 4'-(F₃C)-biphenyl-4-yl | 2-ethylphenyl | 3,4-dimethylphenyl | 1 | CH₃ | CH₃ | H | S |
| 23 | 4'-(F₃C)-biphenyl-4-yl | 2-ethylphenyl | 3,4-dimethylphenyl | 1 | H | CH₃CH₂ | H | S |
| 24 | 4'-(F₃C)-biphenyl-4-yl | 2-ethylphenyl | 3,4-dimethylphenyl | 1 | CH₃ | CH₃CH₂ | H | S |
| 25 | 4'-(F₃C)-biphenyl-4-yl | 2-ethylphenyl | 3,4-dimethylphenyl | 1 | H | H | K | S |
| 26 | 4'-(F₃C)-biphenyl-4-yl | 3-F, 2-ethyl, 1-Cl phenyl | 3,4-dimethylphenyl | 1 | H | H | K | S |
| 27 | 4'-(F₃C)-biphenyl-4-yl | 2,3,4-trifluoro-5-ethylphenyl | 3,4-dimethylphenyl | 1 | H | H | K | S |

TABLE 1-continued
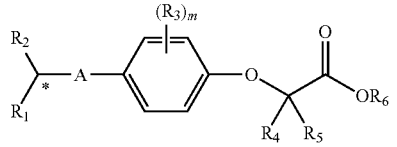
| Ex. | R₁ | R₂ | (R₃)ₘ | m | R₄ | R₅ | R₆ | A |
|---|---|---|---|---|---|---|---|---|
| 28 | 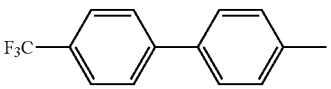 | 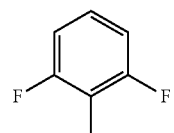 | 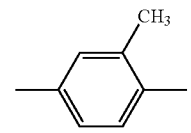 | 1 | H | H | K | S |
| 29 | 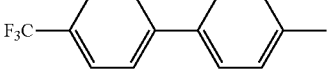 | 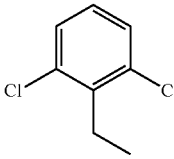 | 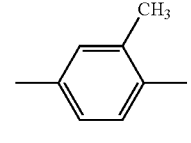 | 1 | H | H | K | S |
| 30 | 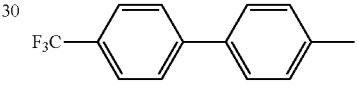 | 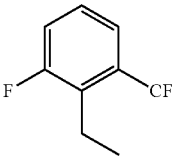 | 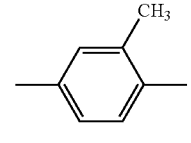 | 1 | H | H | K | S |
| 31 | 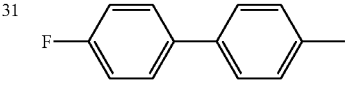 | 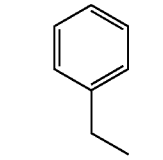 | 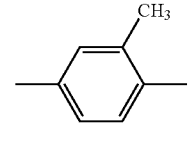 | 1 | H | H | H | S |
| 32 | 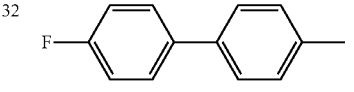 | 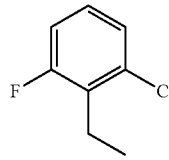 | 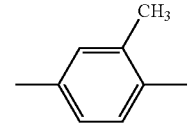 | 1 | H | H | H | S |
| 33 | 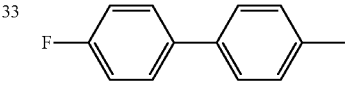 | 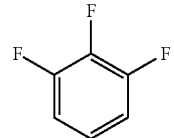 | 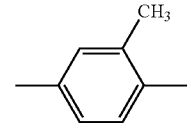 | 1 | H | H | H | S |
| 34 | 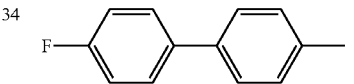 | 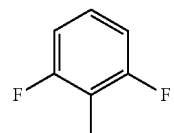 | 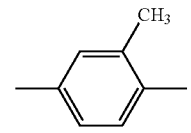 | 1 | H | H | H | S |

TABLE 1-continued

| Ex. | R₁ | R₂ | (R₃)ₘ ring | m | R₄ | R₅ | R₆ | A |
|---|---|---|---|---|---|---|---|---|
| 35 | 4'-F-biphenyl-4-yl | 2,6-dichlorophenyl (with ethyl) | 3,4-dimethylphenyl | 1 | H | H | H | S |
| 36 | 4'-F-biphenyl-4-yl | 2-F-6-CF₃-phenyl (with ethyl) | 3,4-dimethylphenyl | 1 | H | H | H | S |
| 37 | 4'-F-biphenyl-4-yl | phenyl (with ethyl) | 3,4-dimethylphenyl | 1 | CH₃ | CH₃ | H | S |
| 38 | 4'-F-biphenyl-4-yl | phenyl (with ethyl) | 3,4-dimethylphenyl | 1 | H | CH₃CH₂ | H | S |
| 39 | 4'-F-biphenyl-4-yl | phenyl (with ethyl) | 3,4-dimethylphenyl | 1 | CH₃ | CH₃CH₂ | H | S |
| 40 | 4'-F-biphenyl-4-yl | phenyl (with ethyl) | 3,4-dimethylphenyl | 1 | H | H | K | S |
| 41 | 4'-F-biphenyl-4-yl | 2-F-6-Cl-phenyl (with ethyl) | 3,4-dimethylphenyl | 1 | H | H | K | S |

TABLE 1-continued

| Ex. | R₁ | R₂ | (R₃)ₘ ring | m | R₄ | R₅ | R₆ | A |
|---|---|---|---|---|---|---|---|---|
| 42 | 4'-F-biphenyl | 3,5-difluoro-4-ethylphenyl | 3,4-dimethylphenyl | 1 | H | H | K | S |
| 43 | 4'-F-biphenyl | 2,6-difluoro-3-ethylphenyl | 3,4-dimethylphenyl | 1 | H | H | K | S |
| 44 | 4'-F-biphenyl | 2,6-dichloro-3-ethylphenyl | 3,4-dimethylphenyl | 1 | H | H | K | S |
| 45 | 4'-F-biphenyl | 2-F-6-CF₃-3-ethylphenyl | 3,4-dimethylphenyl | 1 | H | H | K | S |
| 46 | 3',4',5'-trifluorobiphenyl | 2-ethylphenyl | 3,4-dimethylphenyl | 1 | H | H | H | S |
| 47 | 3',4',5'-trifluorobiphenyl | 2-F-6-Cl-3-ethylphenyl | 3,4-dimethylphenyl | 1 | H | H | H | S |
| 48 | 3',4',5'-trifluorobiphenyl | 3,5-difluoro-4-ethylphenyl | 3,4-dimethylphenyl | 1 | H | H | H | S |

TABLE 1-continued

| Ex. | R₁ | R₂ | (R₃)ₘ ring | m | R₄ | R₅ | R₆ | A |
|---|---|---|---|---|---|---|---|---|
| 49 | 3,4,5-trifluorobiphenyl | 2,6-difluoro-ethylphenyl | CH₃-substituted | 1 | H | H | H | S |
| 50 | 3,4,5-trifluorobiphenyl | 2,6-dichloro-ethylphenyl | CH₃-substituted | 1 | H | H | H | S |
| 51 | 3,4,5-trifluorobiphenyl | 2-fluoro-6-trifluoromethyl-ethylphenyl | CH₃-substituted | 1 | H | H | H | S |
| 52 | 3,4,5-trifluorobiphenyl | ethylphenyl | CH₃-substituted | 1 | CH₃ | CH₃ | H | S |
| 53 | 3,4,5-trifluorobiphenyl | ethylphenyl | CH₃-substituted | 1 | H | CH₃CH₂ | H | S |
| 54 | 3,4,5-trifluorobiphenyl | ethylphenyl | CH₃-substituted | 1 | CH₃ | CH₃CH₂ | H | S |
| 55 | 3,4,5-trifluorobiphenyl | ethylphenyl | CH₃-substituted | 1 | H | H | K | S |

TABLE 1-continued

| Ex. | R₁ | R₂ | (R₃)ₘ ring | m | R₄ | R₅ | R₆ | A |
|---|---|---|---|---|---|---|---|---|
| 56 | 3,4,5-trifluorobiphenyl-4'-yl | 3-chloro-2-ethyl-6-fluorophenyl | 3,4-dimethylphenyl (CH₃) | 1 | H | H | K | S |
| 57 | 3,4,5-trifluorobiphenyl-4'-yl | 5-ethyl-2,3-difluorophenyl | 3,4-dimethylphenyl (CH₃) | 1 | H | H | K | S |
| 58 | 3,4,5-trifluorobiphenyl-4'-yl | 2-ethyl-3,6-difluorophenyl | 3,4-dimethylphenyl (CH₃) | 1 | H | H | K | S |
| 59 | 3,4,5-trifluorobiphenyl-4'-yl | 3,6-dichloro-2-ethylphenyl | 3,4-dimethylphenyl (CH₃) | 1 | H | H | K | S |
| 60 | 3,4,5-trifluorobiphenyl-4'-yl | 2-ethyl-3-fluoro-6-(trifluoromethyl)phenyl | 3,4-dimethylphenyl (CH₃) | 1 | H | H | K | S |
| 61 | biphenyl-4-yl | 2-ethylphenyl | 3,4-dimethylphenyl (CH₃) | 1 | H | H | H | S |
| 62 | biphenyl-4-yl | 3-chloro-2-ethyl-6-fluorophenyl | 3,4-dimethylphenyl (CH₃) | 1 | H | H | H | S |

TABLE 1-continued
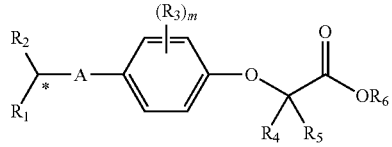
| Ex. | R₁ | R₂ | (R₃)ₘ ring | m | R₄ | R₅ | R₆ | A |
|---|---|---|---|---|---|---|---|---|
| 63 | 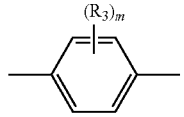 | 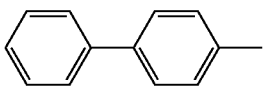 | 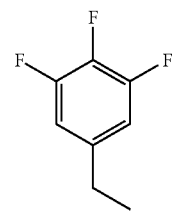 | 1 | H | H | H | S |
| 64 | 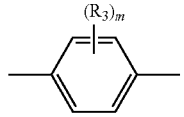 | 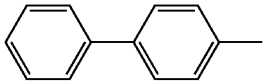 |  | 1 | H | H | H | S |
| 65 | 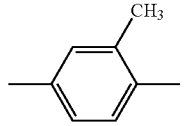 | 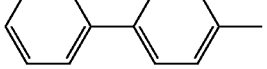 | 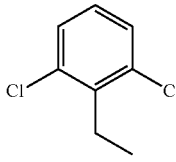 | 1 | H | H | H | S |
| 66 | 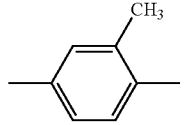 | 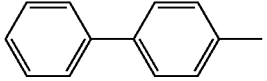 | 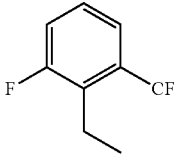 | 1 | H | H | H | S |
| 67 | 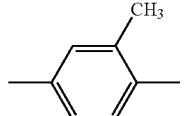 | 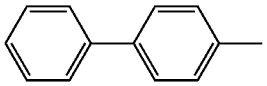 | 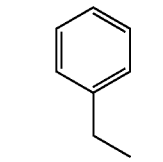 | 1 | CH₃ | CH₃ | H | S |
| 68 | 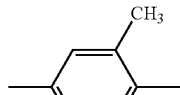 | 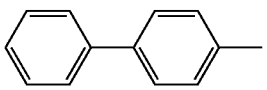 | 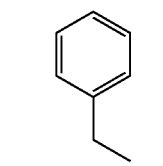 | 1 | H | CH₃CH₂ | H | S |
| 69 | 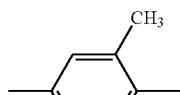 | 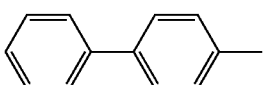 | 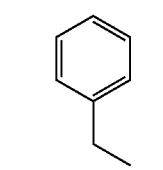 | 1 | CH₃ | CH₃CH₂ | H | S |

TABLE 1-continued
| Ex. | R₁ | R₂ | (R₃)ₘ ring | m | R₄ | R₅ | R₆ | A |
|---|---|---|---|---|---|---|---|---|
| 70 | 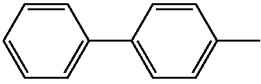 |  | 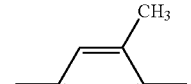 | 1 | H | H | K | S |
| 71 | 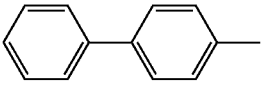 | 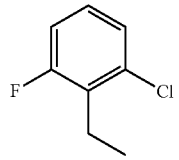 | 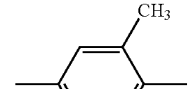 | 1 | H | H | K | S |
| 72 | 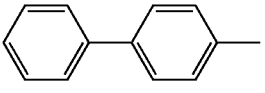 | 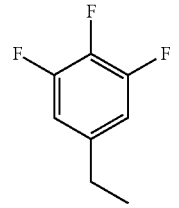 | 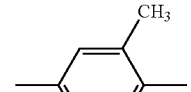 | 1 | H | H | K | S |
| 73 | 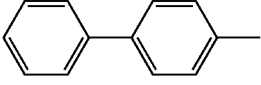 | 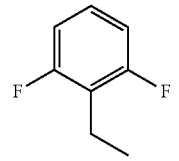 | 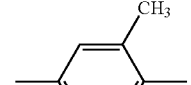 | 1 | H | H | K | S |
| 74 | 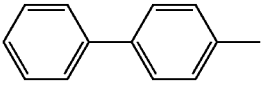 | 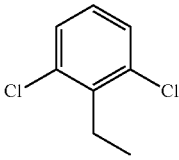 | 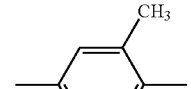 | 1 | H | H | K | S |
| 75 | 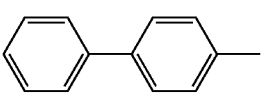 | 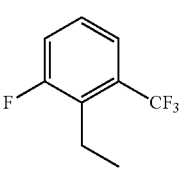 | 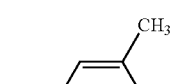 | 1 | H | H | K | S |
| 76 | 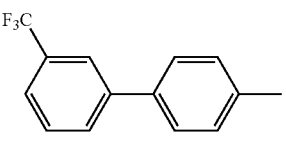 | 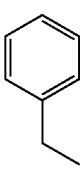 | 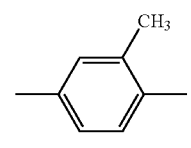 | 1 | H | H | H | S |

TABLE 1-continued
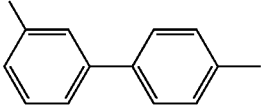
| Ex. | R₁ | R₂ | (R₃)ₘ ring | m | R₄ | R₅ | R₆ | A |
|---|---|---|---|---|---|---|---|---|
| 77 | 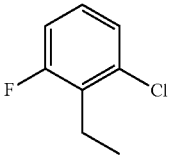 | 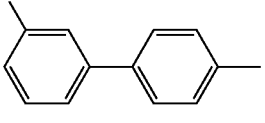 | 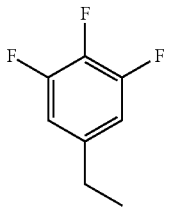 | 1 | H | H | H | S |
| 78 | 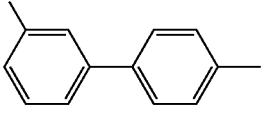 |  | 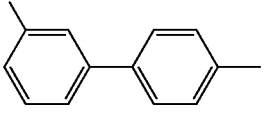 | 1 | H | H | H | S |
| 79 | 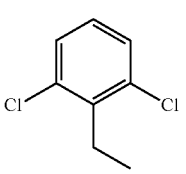 | 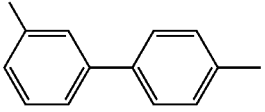 | 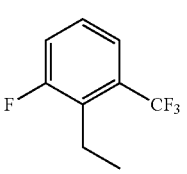 | 1 | H | H | H | S |
| 80 | 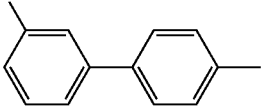 | 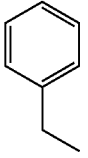 | 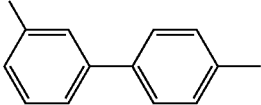 | 1 | H | H | H | S |
| 81 | 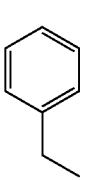 | | | 1 | H | H | H | S |
| 82 | | | | 1 | CH₃ | CH₃ | H | S |
| 83 | | | | 1 | H | CH₃CH₂ | H | S |

TABLE 1-continued
| Ex. | R₁ | R₂ | (R₃)ₘ ring | m | R₄ | R₅ | R₆ | A |
|---|---|---|---|---|---|---|---|---|
| 84 | 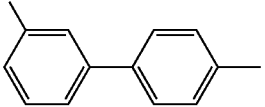 | 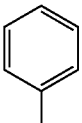 | 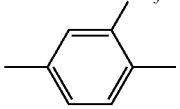 | 1 | CH₃ | CH₃CH₂ | H | S |
| 85 | 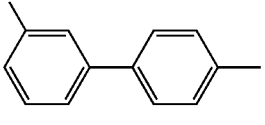 | 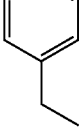 | 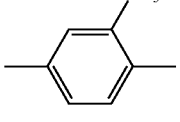 | 1 | H | H | K | S |
| 86 | 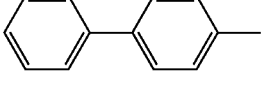 | 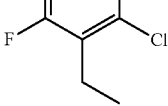 | 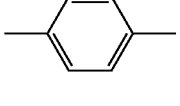 | 1 | H | H | K | S |
| 87 | 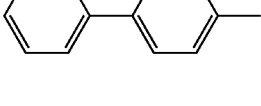 | 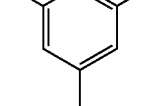 | 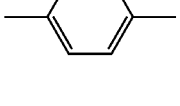 | 1 | H | H | K | S |
| 88 | 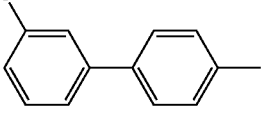 | 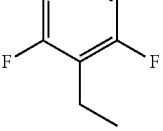 | 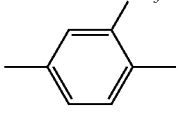 | 1 | H | H | K | S |
| 89 | 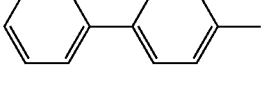 | 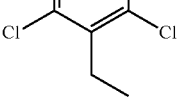 | 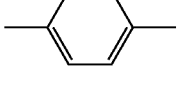 | 1 | H | H | K | S |
| 90 | 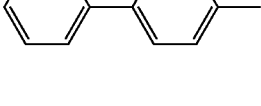 | 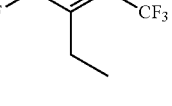 | 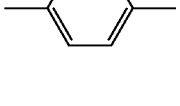 | 1 | H | H | K | S |

TABLE 1-continued

| Ex. | R₁ | R₂ | (R₃)ₘ structure | m | R₄ | R₅ | R₆ | A |
|---|---|---|---|---|---|---|---|---|
| 91 | 5-CF₃-pyridin-2-yl-phenyl | phenyl | 3,4-dimethylphenyl | 1 | H | H | H | S |
| 92 | 5-CF₃-pyridin-2-yl-phenyl | 2-chloro-6-fluorophenyl | 3,4-dimethylphenyl | 1 | H | H | H | S |
| 93 | 5-CF₃-pyridin-2-yl-phenyl | 2,3,4-trifluorophenyl | 3,4-dimethylphenyl | 1 | H | H | H | S |
| 94 | 5-CF₃-pyridin-2-yl-phenyl | 2,6-difluorophenyl | 3,4-dimethylphenyl | 1 | H | H | H | S |
| 95 | 5-CF₃-pyridin-2-yl-phenyl | 2,6-dichlorophenyl | 3,4-dimethylphenyl | 1 | H | H | H | S |
| 96 | 5-CF₃-pyridin-2-yl-phenyl | 2-fluoro-6-(trifluoromethyl)phenyl | 3,4-dimethylphenyl | 1 | H | H | H | S |
| 97 | 5-CF₃-pyridin-2-yl-phenyl | phenyl | 3,4-dimethylphenyl | 1 | CH₃ | H | H | S |

TABLE 1-continued

| Ex. | R₁ | R₂ | (R₃)ₘ aryl | m | R₄ | R₅ | R₆ | A |
|---|---|---|---|---|---|---|---|---|
| 98 | 5-CF₃-pyridin-2-yl-phenyl | phenyl-CH₂ | 3,4-diMe-phenyl (CH₃) | 1 | CH₃ | CH₃CH₂ | H | S |
| 99 | 5-CF₃-pyridin-2-yl-phenyl | phenyl-CH₂ | 3,4-diMe-phenyl (CH₃) | 1 | CH₃ | CH₃CH₂ | H | S |
| 100 | 5-CF₃-pyridin-2-yl-phenyl | phenyl-CH₂ | 3,4-diMe-phenyl (CH₃) | 1 | H | H | K | S |
| 101 | 5-CF₃-pyridin-2-yl-phenyl | 2-F-6-Cl-phenyl-CH₂ | 3,4-diMe-phenyl (CH₃) | 1 | H | H | K | S |
| 102 | 5-CF₃-pyridin-2-yl-phenyl | 3,4,5-triF-phenyl-CH₂ | 3,4-diMe-phenyl (CH₃) | 1 | H | H | K | S |
| 103 | 5-CF₃-pyridin-2-yl-phenyl | 2,6-diF-phenyl-CH₂ | 3,4-diMe-phenyl (CH₃) | 1 | H | H | K | S |
| 104 | 5-CF₃-pyridin-2-yl-phenyl | 2,6-diCl-phenyl-CH₂ | 3,4-diMe-phenyl (CH₃) | 1 | H | H | K | S |

TABLE 1-continued

| Ex. | R₁ | R₂ | (R₃)ₘ ring | m | R₄ | R₅ | R₆ | A |
|---|---|---|---|---|---|---|---|---|
| 105 | 5-(CF₃)-pyridin-2-yl-phenyl | 3-F, 2-Et, 6-CF₃-phenyl | 3-CH₃-phenyl (1,4) | 1 | H | H | K | S |
| 106 | 4-(CF₃)-phenyl-pyridin-5-yl | 2-Et-phenyl | 3-CH₃-phenyl (1,4) | 1 | H | H | H | S |
| 107 | 4-(CF₃)-phenyl-pyridin-5-yl | 3-F, 2-Et, 6-Cl-phenyl | 3-CH₃-phenyl (1,4) | 1 | H | H | H | S |
| 108 | 4-(CF₃)-phenyl-pyridin-5-yl | 3,4,5-triF-phenyl-Et | 3-CH₃-phenyl (1,4) | 1 | H | H | H | S |
| 109 | 4-(CF₃)-phenyl-pyridin-5-yl | 3,5-diF, 2-Et-phenyl | 3-CH₃-phenyl (1,4) | 1 | H | H | H | S |
| 110 | 4-(CF₃)-phenyl-pyridin-5-yl | 3,5-diCl, 2-Et-phenyl | 3-CH₃-phenyl (1,4) | 1 | H | H | H | S |
| 111 | 4-(CF₃)-phenyl-pyridin-5-yl | 3-F, 2-Et, 6-CF₃-phenyl | 3-CH₃-phenyl (1,4) | 1 | H | H | H | S |

TABLE 1-continued
| Ex. | R1 | R2 | (R3)m ring | m | R4 | R5 | R6 | A |
|---|---|---|---|---|---|---|---|---|
| 112 | 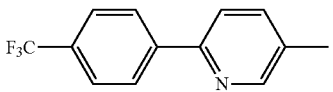 | 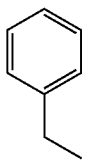 | 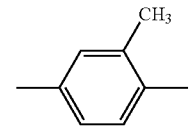 | 1 | CH3 | CH3 | H | S |
| 113 | 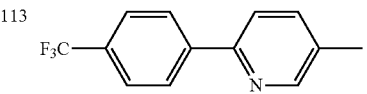 | 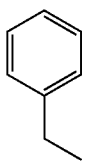 | 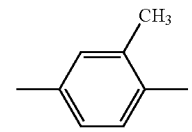 | 1 | H | CH3CH2 | H | S |
| 114 | 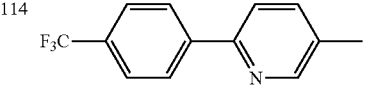 | 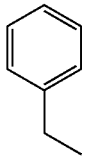 | 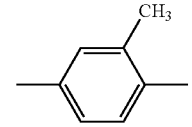 | 1 | CH3 | CH3CH2 | H | S |
| 115 | 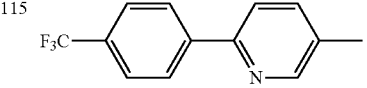 | 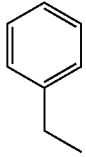 | 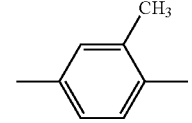 | 1 | H | H | K | S |
| 116 | 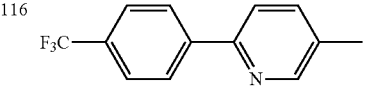 | 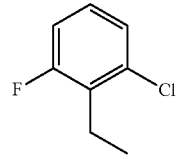 | 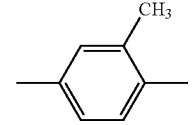 | 1 | H | H | K | S |
| 117 | 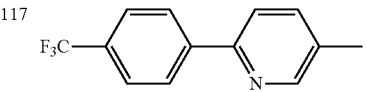 | 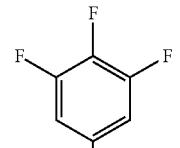 | 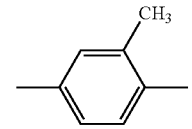 | 1 | H | H | K | S |
| 118 | 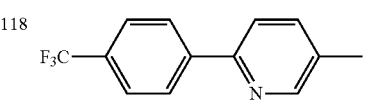 | 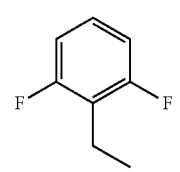 | 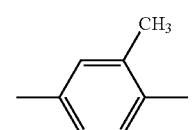 | 1 | H | H | K | S |

TABLE 1-continued
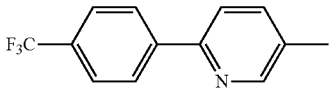
| Ex. | R1 | R2 | (R3)m | m | R4 | R5 | R6 | A |
|---|---|---|---|---|---|---|---|---|
| 119 | 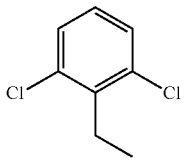 | 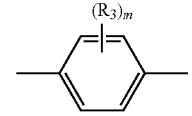 | 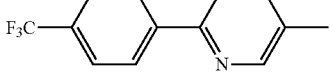 | 1 | H | H | K | S |
| 120 | 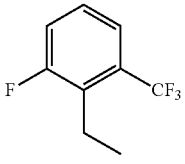 | 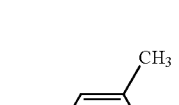 | 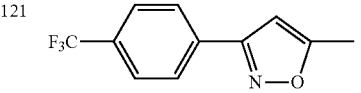 | 1 | H | H | K | S |
| 121 | 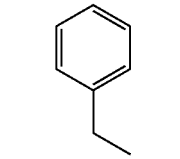 | 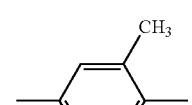 | 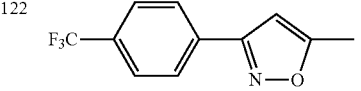 | 1 | H | H | H | S |
| 122 | 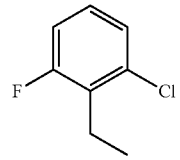 | 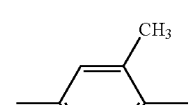 | 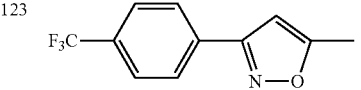 | 1 | H | H | H | S |
| 123 | 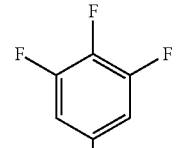 | 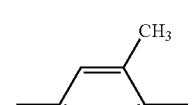 | 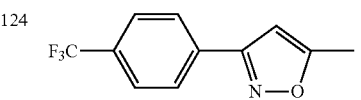 | 1 | H | H | H | S |
| 124 | 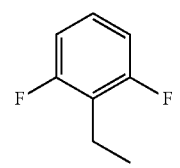 | 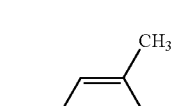 | 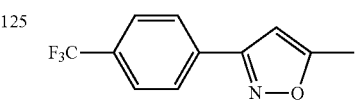 | 1 | H | H | H | S |
| 125 | 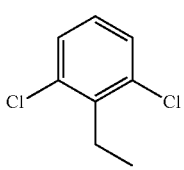 | 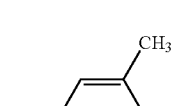 | | 1 | H | H | H | S |

TABLE 1-continued
| Ex. | R₁ | R₂ | (R₃)ₘ | m | R₄ | R₅ | R₆ | A |
|---|---|---|---|---|---|---|---|---|
| 126 | 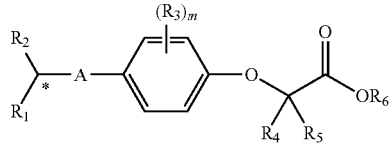 | 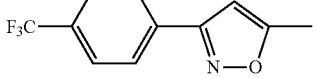 | 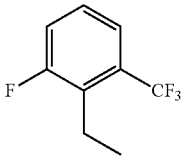 | 1 | H | H | H | S |
| 127 | 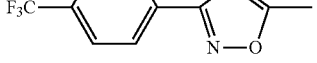 | 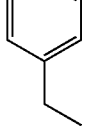 | 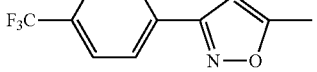 | 1 | CH₃ | CH₃ | H | S |
| 128 | 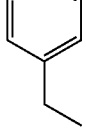 | 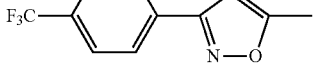 | 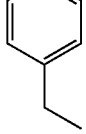 | 1 | H | CH₃CH₂ | H | S |
| 129 | 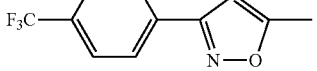 |  | 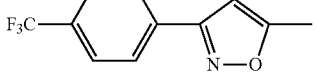 | 1 | CH₃ | CH₃CH₂ | H | S |
| 130 | 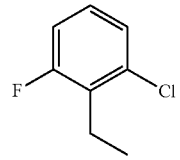 | 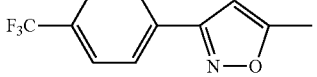 | 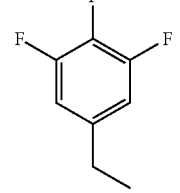 | 1 | H | H | K | S |
| 131 | | | | 1 | H | H | K | S |
| 132 | | | | 1 | H | H | K | S |

TABLE 1-continued

| Ex. | R₁ | R₂ | (R₃)ₘ ring | m | R₄ | R₅ | R₆ | A |
|---|---|---|---|---|---|---|---|---|
| 133 | 4-F₃C-phenyl-(5-methylisoxazol-3-yl) | 2,6-difluoro-phenyl with ethyl | 3,4-dimethylphenyl | 1 | H | H | K | S |
| 134 | 4-F₃C-phenyl-(5-methylisoxazol-3-yl) | 2,6-dichloro-phenyl with ethyl | 3,4-dimethylphenyl | 1 | H | H | K | S |
| 135 | 4-F₃C-phenyl-(5-methylisoxazol-3-yl) | 2-F-6-CF₃-phenyl with ethyl | 3,4-dimethylphenyl | 1 | H | H | K | S |
| 136 | 4-phenoxyphenyl | phenyl-ethyl | 3,4-dimethylphenyl | 1 | H | H | H | S |
| 137 | 4-phenoxyphenyl | 2-F-6-Cl-phenyl with ethyl | 3,4-dimethylphenyl | 1 | H | H | H | S |
| 138 | 4-phenoxyphenyl | 2,3,4-trifluoro-5-ethyl-phenyl | 3,4-dimethylphenyl | 1 | H | H | H | S |
| 139 | 4-phenoxyphenyl | 2,6-difluoro-phenyl with ethyl | 3,4-dimethylphenyl | 1 | H | H | H | S |

TABLE 1-continued

| Ex. | R₁ | R₂ | (R₃)ₘ aryl | m | R₄ | R₅ | R₆ | A |
|---|---|---|---|---|---|---|---|---|
| 140 | 4-phenoxyphenyl | 2,6-dichloro-ethylphenyl | 3,4-dimethylphenyl | 1 | H | H | H | S |
| 141 | 4-phenoxyphenyl | 2-F,6-CF₃-ethylphenyl | 3,4-dimethylphenyl | 1 | H | H | H | S |
| 142 | 4-phenoxyphenyl | ethylphenyl | 3,4-dimethylphenyl | 1 | CH₃ | CH₃ | H | S |
| 143 | 4-phenoxyphenyl | ethylphenyl | 3,4-dimethylphenyl | 1 | H | CH₃CH₂ | H | S |
| 144 | 4-phenoxyphenyl | ethylphenyl | 3,4-dimethylphenyl | 1 | CH₃ | CH₃CH₂ | H | S |
| 145 | 4-phenoxyphenyl | ethylphenyl | 3,4-dimethylphenyl | 1 | H | H | K | S |
| 146 | 4-phenoxyphenyl | 2-F,6-Cl-ethylphenyl | 3,4-dimethylphenyl | 1 | H | H | K | S |

TABLE 1-continued

[Structure: R2-CHR1-*-A-C6H3(R3)m-O-C(R4)(R5)-C(=O)-OR6]

| Ex. | R1 | R2 | (R3)m ring | m | R4 | R5 | R6 | A |
|---|---|---|---|---|---|---|---|---|
| 147 | 4-phenoxyphenyl | 3,4,5-trifluorophenyl | 2,4-dimethylphenyl | 1 | H | H | K | S |
| 148 | 4-phenoxyphenyl | 2,6-difluorophenyl | 2,4-dimethylphenyl | 1 | H | H | K | S |
| 149 | 4-phenoxyphenyl | 2,6-dichlorophenyl | 2,4-dimethylphenyl | 1 | H | H | K | S |
| 150 | 4-phenoxyphenyl | 2-fluoro-6-(trifluoromethyl)phenyl | 2,4-dimethylphenyl | 1 | H | H | K | S |

TABLE 2

| Ex. | $^1$H-NMR |
|---|---|
| 17 | δ 7.66 (s, 4H), 7.45 (d, 2H), 7.31 (d, 2H), 7.08 (m, 4H), 6.55 (d, 1H), 6.85 (m, 1H), 4.58 (s, 2H), 4.52 (t, 1H), 3.41 (q, 2H), 2.05 (s, 3H). |
| 18 | δ 7.74 (q, 2H), 7.16 (m, 4H), 7.02 (d, 1H), 6.80 (t, 4H), 6.61 (q, 1H), 6.40 (d, 1H), 4.64 (s, 2H), 4.38 (t, 1H), 3.23 (q, 2H), 2.14 (s, 3H). |
| 19 | δ 7.67 (s, 4H), 7.45 (d, 2H), 7.30 (d, 2H), 7.10 (m, 4H), 6.74 (m, 1H), 4.59 (s, 2H), 4.44 (t, 1H), 3.31 (q, 2H), 3.41 (q, 2H), 2.16 (s, 3H). |
| 20 | δ 7.66 (s, 4H), 7.45 (d, 2H), 7.33 (d, 2H), 7.08 (m, 2H), 7.05 (m, 3H), 6.50 (d, 1H), 4.61 (t, 1H), 4.56 (s, 2H), 3.56 (m, 2H), 2.16 (s, 3H). |
| 22 | δ 7.66 (s, 4H), 7.43 (d, 2H), 7.22 (m, 5H), 7.03 (m, 4H), 6.50 (d, 1H), 4.19 (m, 2H), 2.14 (s, 3H), 1.55 (s, 6H). |
| 23 | δ 7.67 (s, 4H), 7.45 (d, 2H), 7.23 (m, 5H), 7.03 (m, 4H), 6.51 (d, 1H), 4.54 (t, 1H), 4.30 (q, 1H), 3.27 (m, 2H), 2.18 (s, 3H), 1.98 (m, 2H), 1.10 (t, 3H). |
| 25 | δ 7.67 (s, 4H), 7.45 (d, 2H), 7.22 (m, 5H), 7.05 (m, 4H), 6.54 (d, 1H), 4.59 (s, 2H), 4.24 (m, 1H), 3.24 (m, 2H), 2.18 (s, 3H). |
| 26 | δ 7.66 (s, 4H), 7.45 (d, 2H), 7.31 (d, 2H), 7.08 (m, 4H), 6.55 (d, 1H), 6.85 (m, 1H), 4.58 (s, 2H), 4.52 (t, 1H), 3.41 (q, 2H), 2.05 (s, 3H). |
| 27 | δ 7.74 (q, 2H), 7.16 (m, 4H), 7.02 (d, 1H), 6.80 (t, 4H), 6.61 (q, 1H), 6.40 (d, 1H), 4.64 (s, 2H), 4.38 (t, 1H), 3.23 (q, 2H), 2.14 (s, 3H). |
| 28 | δ 7.67 (s, 4H), 7.45 (d, 2H), 7.30 (d, 2H), 7.10 (m, 4H), 6.74 (m, 1H), 4.59 (s, 2H), 4.44 (t, 1H), 3.31 (q, 2H), 3.41 (q, 2H), 2.16 (s, 3H). |
| 29 | δ 7.66 (s, 4H), 7.45 (d, 2H), 7.33 (d, 2H), 7.08 (m, 2H), 7.05 (m, 3H), 6.50 (d, 1H), 4.61 (t, 1H), 4.56 (s, 2H), 3.56 (m, 2H), 2.16 (s, 3H). |
| 31 | δ 7.51 (m, 2H), 7.39 (d, 2H), 7.20~7.03 (m, 11H), 6.57 (d, 1H), 4.63 (s, 2H), 3.25 (m, 2H), 2.17 (s, 3H). |
| 32 | δ 7.51 (m, 2H), 7.39 (d, 2H), 7.29 (d, 2H), 7.10 (m, 6H), 6.84 (t, 1H), 6.50 (d, 1H), 4.57 (s, 2H), 4.51 (q, 1H), 3.38 (m, 2H), 2.17 (s, 3H). |
| 33 | δ 7.52 (t, 2H), 7.42 (d, 2H), 7.18 (d, 2H), 7.10 (m, 4H), 6.62 (m, 3H), 4.65 (s, 2H), 4.19 (q, 1H), 3.17 (m, 2H), 2.19 (s, 3H). |
| 34 | δ 7.51 (m, 2H), 7.39 (d, 2H), 7.27 (d, 2H), 7.10 (m, 5H), 6.75 (t, 2H), 6.58 (d, 1H), 4.64 (s, 2H), 4.44 (q, 1H), 3.29 (m, 2H), 2.18 (s, 3H). |
| 36 | δ 7.52 (m, 2H), 7.40 (m, 3H), 7.27~7.06 (m, 8H), 6.55 (d, 1H), 6.55 (d, 1H), 4.66 (s, 2H), 4.47 (q, 1H), 3.44 (m, 2H), 2.17 (s, 3H). |

TABLE 2-continued

| Ex. | $^1$H-NMR |
|---|---|
| 40 | δ 7.51 (m, 2H), 7.39 (d, 2H), δ 7.20~7.03 (m, 11H), 6.57 (d, 1H), 4.63 (s, 2H), 3.25 (m, 2H), 2.17 (s, 3H). |
| 41 | δ 7.51 (m, 2H), 7.39 (d, 2H), 7.29 (d, 2H), 7.10 (m, 6H), 6.84 (t, 1H), 6.55 (d, 1H), 4.57 (s, 2H), 4.51 (q, 1H), 3.38 (m, 2H), 2.17 (s, 3H). |
| 42 | δ 7.52 (t, 2H), 7.42 (d, 2H), 7.18 (d, 2H), 7.10 (m, 4H), 6.62 (m, 3H), 4.65 (s, 2H), 4.19 (q, 1H), 3.17 (m, 2H), 2.19 (s, 3H). |
| 43 | δ 7.51 (m, 2H), 7.39 (d, 2H), 7.27 (d, 2H), 7.10 (m, 5H), 6.75 (t, 2H), 6.58 (d, 1H), 4.64 (s, 2H), 4.44 (q, 1H), 3.29 (m, 2H), 2.18 (s, 3H). |
| 45 | δ 7.52 (m, 2H), 7.40 (m, 3H), 7.27~7.06 (m, 8H), 6.55 (d, 1H), 6.55 (d, 1H), 4.66 (s, 2H), 4.47 (q, 1H), 3.44 (m, 2H), 2.17 (s, 3H). |
| 46 | δ 7.34 (d, 2H), 7.17 (m, 7H), 7.07 (m, 2H), 7.02 (d, 2H), 6.56 (d, 1H), 4.71 (s, 2H), 4.28 (q, 1H), 3.18 (m, 2H), 2.17 (s, 3H). |
| 47 | δ 7.3 (d, 2H), 7.29 (d, 2H), 7.14 (m, 2H), 7.08 (m, 4H), 6.84 (m, 1H), 6.56 (d, 1H), 4.64 (s, 2H), 4.50 (q, 1H), 3.38 (m, 2H), 2.17 (s, 3H). |
| 49 | δ 7.34 (d, 2H), 7.28 (d, 2H), 7.14 (m, 2H), 7.08 (m, 3H), 6.75 (t, 2H), 6.57 (d, 1H), 4.65 (s, 2H), 4.43 (q, 1H), 3.29 (m, 2H), 2.18 (s, 3H). |
| 50 | δ 7.34 (q, 4H), 7.21 (d, 2H), 7.15 (m, 2H), 7.07 (m, 3H), 6.54 (d, 1H), 4.62 (s, 2H), 4.59 (q, 1H), 3.54 (m, 2H), 2.16 (s, 3H). |
| 55 | δ 7.34 (d, 2H), 7.17 (m, 7H), 7.07 (m, 2H), 7.02 (d, 2H), 6.56 (d, 1H), 4.71 (s, 2H), 4.28 (q, 1H), 3.18 (m, 2H), 2.17 (s, 3H). |
| 56 | δ 7.34 (d, 2H), 7.29 (d, 2H), 7.14 (m, 2H), 7.08 (m, 4H), 6.84 (m, 1H), 6.56 (d, 1H), 4.64 (s, 2H), 4.50 (q, 1H), 3.38 (m, 2H), 2.17 (s, 3H). |
| 58 | δ 7.34 (d, 2H), 7.28 (d, 2H), 7.14 (m, 2H), 7.08 (m, 3H), 6.75 (t, 2H), 6.57 (d, 1H), 4.65 (s, 2H), 4.43 (q, 1H), 3.29 (m, 2H), 2.18 (s, 3H). |
| 59 | δ 7.34 (q, 4H), 7.21 (d, 2H), 7.15 (m, 2H), 7.07 (m, 3H), 6.54 (d, 1H), 4.62 (s, 2H), 4.59 (q, 1H), 3.54 (m, 2H), 2.16 (s, 3H). |
| 61 | δ 7.55 (q, 2H), 7.42 (m, 4H), 7.31 (m, 1H), 7.17 (m, 5H), 7.05 (m, 4H), 6.54 (m, 1H), 4.60 (s, 2H), 4.28 (m, 2H), 3.21 (m, 2H), 2.17 (s, 3H). |
| 62 | δ 7.55 (q, 2H), 7.42 (m, 4H), 7.31 (m, 3H), 7.08 (m, 4H), 6.85 (m, 1H), 6.54 (m, 1H), 4.61 (s, 2H), 4.50 (q, 2H), 3.39 (m, 2H), 2.17 (s, 3H). |
| 63 | δ 7.57 (q, 2H), 7.47 (q, 2H), 7.43 (m, 2H), 7.34 (m, 1H), 7.18 (d, 2H), 7.09 (m, 2H), 6.63 (m, 3H), 4.65 (s, 2H), 4.19 (q, 1H), 3.16 (m, 2H), 2.18 (s, 3H). |
| 66 | δ 7.56 (q, 2H), 7.41 (m, 5H), 7.33 (m, 1H), 7.27 (d, 2H), 7.12 (t, 1H), 7.06 (m, 2H), 6.55 (d, 1H), 4.61 (s, 2H), 4.48 (q, 1H), 3.45 (m, 2H), 2.17 (s, 3H). |
| 70 | δ 7.55 (q, 2H), 7.42 (m, 4H), 7.31 (m, 1H), 7.17 (m, 5H), 7.05 (m, 4H), 6.54 (m, 1H), 4.60 (s, 2H), 4.28 (m, 2H), 3.21 (m, 2H), 2.17 (s, 3H). |
| 71 | δ 7.55 (q, 2H), 7.42 (m, 4H), 7.31 (m, 3H), 7.08 (m, 4H), 6.85 (m, 1H), 6.54 (m, 1H), 4.61 (s, 2H), 4.5 (q, 2H), 3.39 (m, 2H), 2.17 (s, 3H). |
| 72 | δ 7.57 (q, 2H), 7.47 (q, 2H), 7.43 (m, 2H), 7.34 (m, 1H), 7.18 (d, 2H), 7.09 (m, 2H), 6.63 (m, 3H), 4.65 (s, 2H), 4.19 (q, 1H), 3.16 (m, 2H), 2.18 (s, 3H). |
| 75 | δ 7.56 (q, 2H), 7.41 (m, 5H), 7.33 (m, 1H), 7.27 (d, 2H), 7.12 (t, 1H), 7.06 (m, 2H), 6.55 (d, 1H), 4.61 (s, 2H), 4.48 (q, 1H), 3.45 (m, 2H), 2.17 (s, 3H). |
| 76 | δ 7.79 (s, 1H), 7.72 (d, 1H), 7.57 (d, 1H), 7.52 (t, 1H), 7.45 (d, 2H), 7.24~7.13 (m, 5H), 7.08 (m, 2H), 7.03 (d, 2H), 6.56 (d, 1H), 4.63 (s, 2H), 4.29 (q, 1H), 3.25 (m, 2H), 2.17 (s, 3H). |
| 77 | δ 7.78 (s, 1H), 7.72 (d, 1H), 7.57 (d, 1H), 7.52 (t, 1H), 7.45 (d, 2H), 7.32 (q, 2H), 7.09 (m, 4H), 6.84 (m, 1H), 6.54 (m, 1H), 4.63 (s, 2H), 4.52 (q, 2H), 3.39 (m, 2H), 2.18 (s, 3H). |
| 78 | δ 7.79 (s, 1H), 7.72 (d, 1H), 7.58 (d, 1H), 7.54 (t, 1H), 7.47 (d, 2H), 7.21 (d, 2H), 7.09 (d, 2H), 6.63 (m, 2H), 6.59 (d, 1H), 4.65 (s, 2H), 4.20 (q, 1H), 3.17 (m, 2H), 2.19 (s, 3H). |
| 79 | δ 7.78 (s, 1H), 7.72 (d, 1H), 7.57 (d, 1H), 7.52 (t, 1H), 7.45 (d, 2H), 7.30 (d, 2H), 7.09 (m, 3H), 6.76 (t, 2H), 6.58 (d, 1H), 4.64 (s, 2H), 4.45 (q, 1H), 3.30 (m, 2H), 2.19 (s, 3H). |
| 81 | δ 7.79 (s, 1H), 7.72 (d, 1H), 7.57 (d, 1H), 7.44 (m, 3H), 7.12 (t, 1H), 7.07 (m, 2H), 6.56 (d, 1H), 4.68 (s, 2H), 4.49 (1, 1H), 3.45 (m, 2H), 2.17 (s, 3H). |
| 85 | δ 7.79 (s, 1H), 7.72 (d, 1H), 7.57 (d, 1H), 7.52 (t, 1H), 7.45 (d, 2H), 7.24~7.13 (m, 5H), 7.08 (m, 2H), 7.03 (d, 2H), 6.56 (d, 1H), 4.63 (s, 2H), 4.29 (q, 1H), 3.25 (m, 2H), 2.17 (s, 3H). |
| 86 | δ 7.78 (s, 1H), 7.72 (d, 1H), 7.57 (d, 1H), 7.52 (t, 1H), 7.45 (d, 2H), 7.32 (q, 2H), 7.09 (m, 4H), 6.84 (m, 1H), 6.54 (m, 1H), 4.63 (s, 2H), 4.52 (q, 2H), 3.39 (m, 2H), 2.18 (s, 3H). |
| 87 | δ 7.79 (s, 1H), 7.72 (d, 1H), 7.58 (d, 1H), 7.54 (t, 1H), 7.47 (d, 2H), 7.21 (d, 2H), 7.09 (d, 2H), 6.63 (m, 2H), 6.59 (d, 1H), 4.65 (s, 2H), 4.20 (q, 1H), 3.17 (m, 2H), 2.19 (s, 3H). |
| 88 | δ 7.78 (s, 1H), 7.72 (d, 1H), 7.57 (d, 1H), 7.52 (t, 1H), 7.45 (d, 2H), 7.30 (d, 2H), 7.09 (m, 3H), 6.76 (t, 2H), 6.58 (d, 1H), 4.64 (s, 2H), 4.45 (q, 1H), 3.30 (m, 2H), 2.19 (s, 3H). |
| 90 | δ 7.79 (s, 1H), 7.72 (d, 1H), 7.57 (d, 1H), 7.44 (m, 3H), 7.12 (t, 1H), 7.07 (m, 2H), 6.56 (d, 1H), 4.68 (s, 2H), 4.49 (1, 1H), 3.45 (m, 2H), 2.17 (s, 3H). |
| 106 | δ 8.15 (d, 1H), 7.94 (d, 2H), 7.74 (q, 1H), 7.68 (d, 2H), 7.63 (d, 1H), 7.23 (t, 2H), 7.16 (t, 1H), 7.08 (d, 2H), 7.02 (d, 1H), 6.98 (q, 1H), 6.54 (d, 1H), 4.56 (s, 2H), 4.30 (q, 1H), 3.37 (m, 1H), 2.15 (s, 3H). |
| 108 | δ 8.10 (t, 3H), 7.96 (d, 1H), 7.79 (m, 3H), 7.00 (s, 1H), 6.95 (d, 1H), 6.75 (t, 2H), 6.60 (d, 1H), 4.62 (s, 2H), 4.26 (q, 1H), 3.31 (m, 1H), 3.15 (m, 1H), 2.15 (s, 3H). |
| 109 | δ 8.17 (s, 1H), 8.02 (d, 2H), 7.84 (d, 1H), 7.69 (t, 3H), 7.12 (m, 2H), 7.04 (d, 1H), 6.78 (t, 1H), 6.57 (d, 1H), 4.61 (s, 2H), 4.41 (q, 1H), 3.35 (m, 2H), 2.17 (s, 3H). |
| 111 | δ 8.18 (s, 1H), 8.01 (d, 2H), 7.90 (d, 1H), 7.70 (q, 3H), 7.44 (t, 1H), 7.30 (m, 1H), 7.14 (t, 1H), 7.03 (m, 2H), 6.56 (d, 1H), 4.60 (s, 2H), 4.44 (q, 1H), 3.53 (m, 1H), 3.41 (m, 1H), 2.16 (s, 3H). |
| 115 | δ 8.15 (d, 1H), 7.94 (d, 2H), 7.74 (q, 1H), 7.68 (d, 2H), 7.63 (d, 1H), 7.23 (t, 2H), 7.16 (t, 1H), 7.08 (d, 2H), 7.02 (d, 1H), 6.98 (q, 1H), 6.54 (d, 1H), 4.56 (s, 2H), 4.30 (q, 1H), 3.37 (m, 1H), 2.15 (s, 3H). |
| 117 | δ 8.10 (t, 3H), 7.96 (d, 1H), 7.79 (m, 3H), 7.00 (s, 1H), 6.95 (d, 1H), 6.75 (t, 2H), 6.60 (d, 1H), 4.62 (s, 2H), 4.26 (q, 1H), 3.31 (m, 1H), 3.15 (m, 1H), 2.15 (s, 3H). |
| 118 | δ 8.17 (s, 1H), 8.02 (d, 2H), 7.84 (d, 1H), 7.69 (t, 3H), 7.12 (m, 2H), 7.04 (d, 1H), 6.78 (t, 1H), 6.57 (d, 1H), 4.61 (s, 2H), 4.41 (q, 1H), 3.35 (m, 2H), 2.17 (s, 3H). |
| 120 | δ 8.18 (s, 1H), 8.01 (d, 2H), 7.90 (d, 1H), 7.70 (q, 3H), 7.44 (t, 1H), 7.30 (m, 1H), 7.14 (t, 1H), 7.03 (m, 2H), 6.56 (d, 1H), 4.60 (s, 2H), 4.44 (q, 1H), 3.53 (m, 1H), 3.41 (m, 1H), 2.16 (s, 3H). |
| 121 | δ 7.69 (m, 2H), 7.15 (m, 9H), 6.52 (d, 1H), 6.24 (s, 1H), 4.58 (s, 2H), 4.23 (q, 1H), 3.39 (m, 2H), 2.16 (s, 3H). |
| 122 | δ 7.73 (m, 2H), 7.14 (m, 6H), 6.90 (m, 1H), 6.56 (d, 2H), 4.65 (q, 1H), 4.59 (s, 2H), 3.42 (m, 2H), 2.17 (s, 3H). |
| 123 | δ 7.69 (m, 2H), 7.48 (d, 2H), 7.21 (d, 2H), 7.10 (d, 2H), 6.63 (m, 2H), 4.65 (s, 2H), 4.20 (t, 1H), 3.17 (m, 2H), 2.18 (s, 3H). |
| 124 | δ 7.73 (m, 2H), δ 7.14 (m, 6H), δ 6.90 (m, 1H), δ 6.56 (d, 2H), δ 4.59 (s, 2H), δ 4.26 (q, 1H), δ 3.39 (m, 2H), δ 2.17 (s, 3H). |
| 130 | δ 7.69 (m, 2H), 7.15 (m, 9H), 6.52 (d, 1H), 6.24 (s, 1H), 4.58 (s, 2H), 4.23 (q, 1H), 3.39 (m, 2H), 2.16 (s, 3H). |
| 131 | δ 7.73 (m, 2H), 7.14 (m, 6H), 6.90 (m, 1H), 6.56 (d, 2H), 4.65 (q, 1H), 4.59 (s, 2H), 3.42 (m, 2H), 2.17 (s, 3H). |
| 132 | δ 7.73 (m, 2H), 7.14 (m, 6H), 6.90 (m, 1H), 6.56 (d, 2H), 4.65 (q, 1H), 4.59 (s, 2H), 3.42 (m, 2H), 2.17 (s, 3H). |
| 133 | δ 7.73 (m, 2H), 7.14 (m, 6H), 6.90 (m, 1H), 6.56 (d, 2H), 4.59 (s, 2H), 4.26 (q, 1H), 3.39 (m, 2H), 2.17 (s, 3H). |
| 136 | δ 7.30~6.57 (m, 16H), 6.55 (d, 1H), 4.59 (s, 2H), 4.18 (q, 1H), 3.24 (m, 2H), 2.18 (s, 3H). |
| 137 | δ 7.30~6.57 (m, 14H), 6.54 (d, 1H), δ 4.58 (s, 2H), 4.34 (q, 1H), 3.24 (m, 2H), 2.18 (s, 3H). |
| 139 | δ 7.30~6.55 (m, 14H), 6.54 (d, 1H), 4.59 (s, 2H), 4.34 (q, 1H), 3.24 (m, 2H), 2.18 (s, 3H). |
| 140 | δ 7.29~6.52 (m, 14H), 6.52 (d, 1H), 4.57 (s, 2H), 4.50 (q, 1H), 3.47 (m, 2H), 2.17 (s, 3H). |
| 145 | δ 7.30~6.57 (m, 16H), 6.55 (d, 1H), 4.59 (s, 2H), 4.18 (q, 1H), 3.24 (m, 2H), 2.18 (s, 3H). |

TABLE 2-continued

| Ex. | $^1$H-NMR |
|---|---|
| 146 | δ 7.30~6.57 (m, 14H), 6.54 (d, 1H), 4.58 (s, 2H), 4.34 (q, 1H), 3.24 (m, 2H), 2.18 (s, 3H). |
| 148 | δ 7.30~6.55 (m, 14H), 6.54 (d, 1H), 4.59 (s, 2H), 4.34 (q, 1H), 3.24 (m, 2H), 2.18 (s, 3H). |
| 149 | δ 7.29~6.52 (m, 14H), 6.52 (d, 1H), 4.57 (s, 2H), 4.50 (q, 1H), 3.47 (m, 2H), 2.17 (s, 3H). |

Example 151

Preparation of Compound S151

[Process A]

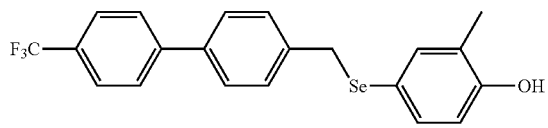

S151

590 mg of 4-iodo-2-methylphenol was dissolved in 20 ml of anhydride tetrahydrofuran in the presence of nitrogen and at that time temperature was maintained at 0° C. 1.5 ml of isopropylmagnesiumchloride (2 M) was slowly added thereto, followed by reaction for 10 minutes. The reaction solution was cooled down to −78° C., to which 2.00 ml of tert-butyl lithium (1.7 M-hexane solution, 1.0 equivalent) was slowly added. After stirring for 10 minutes, 158 mg of solid Se (2 mmol, 1.0 equivalent) was added thereto at the same temperature at a time. The reaction continued for 40 minutes with raising the temperature up to 15° C. 541 mg (2 mmol, 1.0 equivalent) of 4-chloromethyl-4'-trifluoromethyl-biphenyl was dissolved in 10 ml of anhydride THF, which was slowly added thereto at the same temperature. After one more hour of reaction, the reaction was terminated by ammonium chloride solution, and the organic solvent was extracted by using ethylacetate and sodium chloride solution, which was dried over magnesium sulfate to eliminate moisture of the organic layer. After filtering, the solvent was distilled under reduced pressure, and the residue was purified by silica gel column chromatography to give 712 mg (yield: 84%) of the target compound.
$^1$H NMR (300 MHz, CDCl$_3$) δ7.67 (s, 4H), 67.50 (d, 2H), 67.28 (t, 2H), 67.13 (s, 1H), 67.07 (q, 1H), 66.68 (d, 1H) 65.20 (s, 1H), 64.02 (s, 2H), 62.17 (s, 3H)

Example 152

Preparation of Compound S152

[Process B]

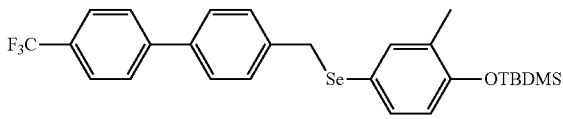

S152

842 mg (2 mmol) of the compound S151 and 290 mg (2.0 equivalent) of imidazole were completely dissolved in 20 ml of dimethylformamide. 165 mg (1.1 equivalent) of tert-butyldimethylsilylchloride was slowly added thereto, followed by stirring at room temperature for 4 hours. Upon completion of the reaction, the organic solvent was extracted by using ammonium chloride solution and ethylacetate. Moisture of the organic layer was dried over magnesium sulfate. Silica gel column was used to purify and the solvent was distillated under reduced pressure to give 1018 mg (yield: 95%) of the target compound.
$^1$H NMR (300 MHz, CDCl$_3$) δ7.67 (s, 4H), 67.50 (d, 2H), 67.27 (t, 2H), 67.13 (s, 1H), 67.05 (q, 1H), 66.66 (d, 1H), 64.04 (s, 2H), 62.15 (s, 3H), 61.01 (s, 9H), 60.20 (s, 6H).

Example 153

Preparation of Compound S153

[Process C]

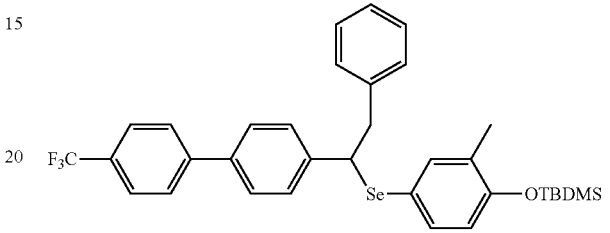

S153

1071 mg (2 mmol) of the compound S152 was dissolved in 20 ml of anhydride tetrahydrofuran and the temperature was lowered to −78° C. 3.6 ml (1.8 M, 2.0 equivalent) of lithium diisopropyl amide (LDA) was slowly added thereto. Then, 301 μl (2.2 mmol) of benzylbromide was added to the reaction solution, and the temperature was slowly raised to room temperature. After 30 more minutes of reaction, the reaction was terminated by ammonium chloride solution, and the organic solvent was extracted by using ethylacetate and sodium chloride solution, which was dried over magnesium sulfate to eliminate moisture of the organic layer. After filtering, the solvent was distilled under reduced pressure, and the residue was purified by silica gel column chromatography to give 938 mg (yield: 75%) of the target compound.
$^1$H NMR (300 MHz, CDCl$_3$) δ7.67 (s, 4H), 67.47-7.05 (m, 11H), δ6.63 (d, 1H), 64.30 (m, 1H), 63.54 (m, 1H), 63.24 (m, 1H), 62.12 (s, 3H), 61.01 (s, 9H), 60.21 (s, 6H).

Example 154

Preparation of Compound S154

[Process C]

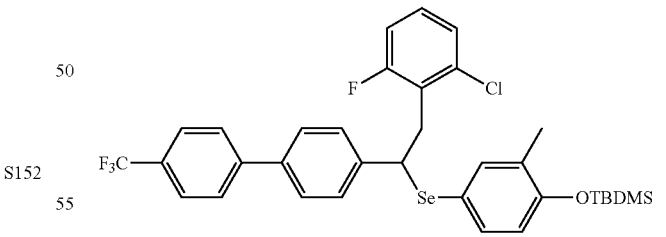

S154

1071 mg (2 mmol) of the compound S152 was dissolved in 20 ml of anhydride tetrahydrofuran and the temperature was lowered to −78° C. 3.6 ml (1.8 M, 2.0 equivalent) of lithium diisopropyl amide (LDA) was slowly added thereto. Then, 297 μl (2.2 mmol) of 2-chloro-5-fluorobenzylbromide was added to the reaction solution, and the temperature was slowly raised to room temperature. After 30 more minutes of reaction, the reaction was terminated by ammonium chloride solution, and the organic solvent was extracted by using ethylacetate and sodium chloride solution, which was dried over magnesium sulfate to eliminate moisture of the organic layer.

After filtering, the solvent was distillated under reduced pressure, and the residue was purified by silica gel column chromatography to give 1017 mg (yield: 75%) of the target compound.

$^1$H NMR (300 MHz, CDCl$_3$) δ7.66 (s, 4H), δ7.45 (d, 2H), δ7.31 (d, 2H), δ7.08 (m, 4H), δ6.85 (m, 1H), δ6.60 (d, 1H), δ4.50 (t, 1H), δ3.41 (d, 2H), δ2.11 (s, 3H), δ1.01 (s, 9H), δ0.20 (s, 6H).

Example 155

Preparation of Compound S155

[Process C]

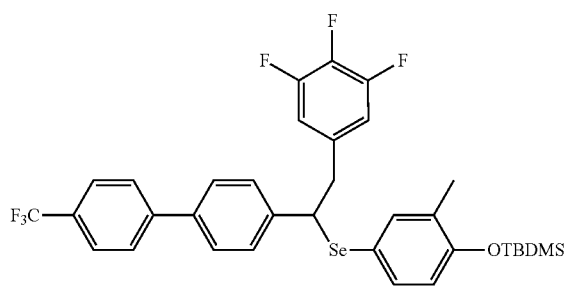

S155

1071 mg (2 mmol) of the compound S152 was dissolved in 20 ml of anhydride tetrahydrofuran and the temperature was lowered to −78° C. 3.6 ml (1.8 M, 2.0 equivalent) of lithium diisopropyl amide (LDA) was slowly added thereto. Then, 310 μl (2.2 mmol) of 3,4,5-trifluorobenzylbromide was added to the reaction solution, and the temperature was slowly raised to room temperature. After 30 more minutes of reaction, the reaction was terminated by ammonium chloride solution, and the organic solvent was extracted by using ethylacetate and sodium chloride solution, which was dried over magnesium sulfate to eliminate moisture of the organic layer. After filtering, the solvent was distillated under reduced pressure, and the residue was purified by silica gel column chromatography to give 1020 mg (yield: 75%) of the target compound (EIMS: 681.1[M+H]$^+$).

Example 156

Preparation of Compound S156

[Process C]

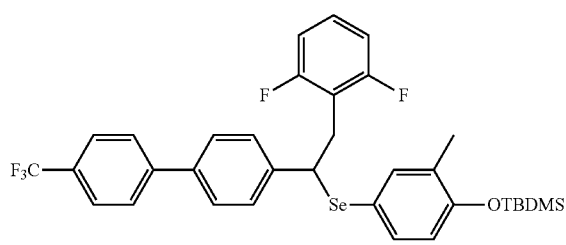

S156

1071 mg (2 mmol) of the compound S152 was dissolved in 20 ml of anhydride tetrahydrofuran and the temperature was lowered to −78° C. 3.6 ml (1.8 M, 2.0 equivalent) of lithium diisopropyl amide (LDA) was slowly added thereto. Then, 285 μl (2.2 mmol) of 2,5-difluorobenzylbromide was added to the reaction solution, and the temperature was slowly raised to room temperature. After 30 more minutes of reaction, the reaction was terminated by ammonium chloride solution, and the organic solvent was extracted by using ethylacetate and sodium chloride solution, which was dried over magnesium sulfate to eliminate moisture of the organic layer. After filtering, the solvent was distillated under reduced pressure, and the residue was purified by silica gel column chromatography to give 992 mg (yield: 75%) of the target compound.

$^1$H NMR (300 MHz, CDCl$_3$) δ7.67 (s, 4H), δ7.45 (d, 2H), δ7.30 (d, 2H), δ7.09 (m, 4H), δ6.75 (m, 1H), δ6.54 (m, 1H), δ4.44 (t, 1H), δ3.35 (m, 2H), δ2.19 (s, 3H), δ1.01 (s, 9H), δ0.20 (s, 6H).

Example 157

Preparation of Compound S157

[Process C]

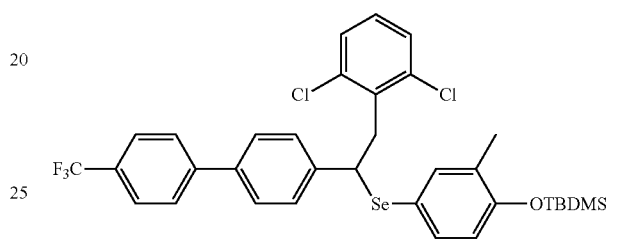

S157

1071 mg (2 mmol) of the compound S152 was dissolved in 20 ml of anhydride tetrahydrofuran and the temperature was lowered to −78° C. 3.6 ml (1.8 M, 2.0 equivalent) of lithium diisopropyl amide (LDA) was slowly added thereto. Then, 330 μl (2.2 mmol) of 2,5-dichlorobenzylbromide was added to the reaction solution, and the temperature was slowly raised to room temperature. After 30 more minutes of reaction, the reaction was terminated by ammonium chloride solution, and the organic solvent was extracted by using ethylacetate and sodium chloride solution, which was dried over magnesium sulfate to eliminate moisture of the organic layer. After filtering, the solvent was distillated under reduced pressure, and the residue was purified by silica gel column chromatography to give 1042 mg (yield: 75%) of the target compound.

$^1$H NMR (300 MHz, CDCl$_3$) δ7.66 (s, 4H), δ7.45 (d, 2H), δ7.33 (d, 2H), δ7.08 (m, 2H), δ7.05 (m, 3H), δ6.52 (d, 1H), δ4.61 (q, 1H), δ3.58 (m, 2H), δ2.19 (s, 3H), δ1.01 (s, 9H), δ0.20 (s, 6H).

Example 158

Preparation of Compound S158

[Process C]

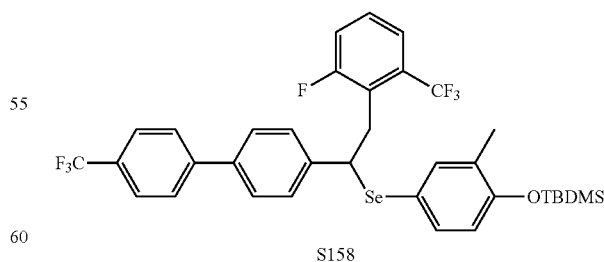

S158

1071 mg (2 mmol) of the compound S152 was dissolved in 20 ml of anhydride tetrahydrofuran and the temperature was lowered to −78° C. 3.6 ml (1.8 M, 2.0 equivalent) of lithium diisopropyl amide (LDA) was slowly added thereto. Then, 561 mg (2.2 mmol) of 2-chloro-5-trifluoromethylbenzylbromide was added to the reaction solution, and the temperature was slowly raised to room temperature. After 30 more minutes of reaction, the reaction was terminated by ammonium chloride solution, and the organic solvent was extracted by using ethylacetate and sodium chloride solution, which was dried over magnesium sulfate to eliminate moisture of the organic layer. After filtering, the solvent was distillated under reduced pressure, and the residue was purified by silica gel column chromatography to give 1068 mg (yield: 75%) of the target compound (EIMS: 713.1[M+H]⁺).

Example 159

Preparation of Compound S159

[Process D]

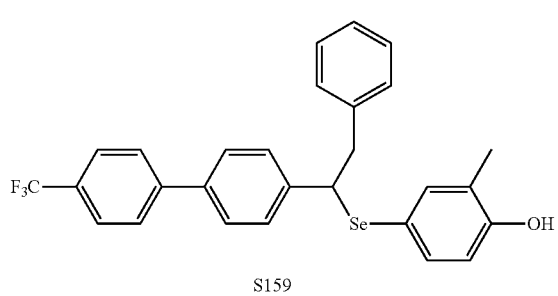

S159

1251 mg (2 mmol) of the compound S153 prepared in example 153 was completely dissolved in 20 ml of tetrahydrofuran. 5 ml (1M-tetrahydrofuran solution, 2.5 equivalent) of tetrabutylammoniumfluoride (TBAF) was slowly added thereto at room temperature. After 30 minutes of reaction, the organic solvent was extracted by using ammonium chloride solution and ethylacetate, which was dried over magnesium sulfate to eliminate moisture of the organic layer. After filtering, the solvent was distillated under reduced pressure, and the residue was purified by silica gel column chromatography to give 940 mg (yield: 92%) of the target compound.

$^1$H NMR (300 MHz, CDCl$_3$) δ7.67 (s, 4H), 67.47-7.05 (m, 11H), 66.63 (d, 1H), 64.30 (m, 1H), 63.54 (m, 1H), 63.24 (m, 1H), 62.14 (s, 3H).

Example 160

Preparation of Compound S160

[Process E]

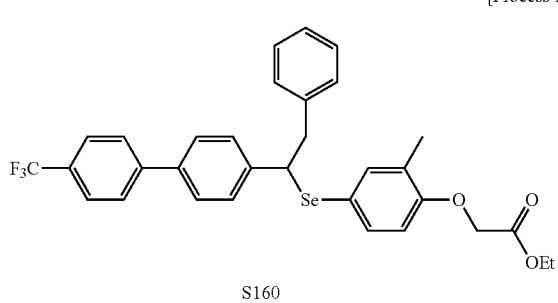

S160

511 mg (1 mmol) of the compound S159 prepared in example 159 was well mixed with 10 ml of acetone containing 5% water and 346 mg (2.5 mmol, 2.5 equivalent) of potassium carbonate at room temperature. 134 μl (1.2 mmol, 1.2 equivalent) of bromoacetateethylester was added thereto, following vigorous stirring for 4 hours. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 556 mg (yield: 93%) of the target compound.

$^1$H NMR (300 MHz, CDCl$_3$) δ7.67 (s, 4H), 67.45 (d, 2H), 67.22 (m, 5H), 67.05 (m, 4H), 66.54 (d, 1H), 64.59 (s, 2H), 64.26 (m, 3H), 63.24 (m, 2H), 62.18 (s, 3H), 61.27 (t, 3H).

Example 161

Preparation of Compound S161

[Process E]

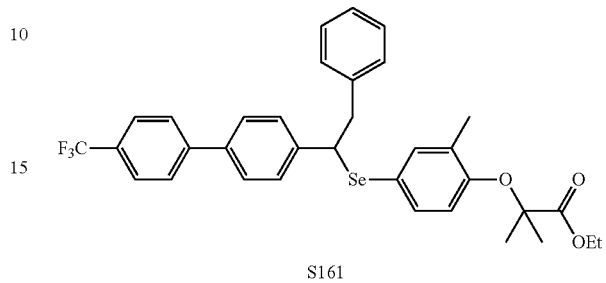

S161

511 mg (1 mmol) of the compound S159 prepared in example 159 was well mixed with 10 ml of acetone containing 5% water and 346 mg (2.5 mmol, 2.5 equivalent) of potassium carbonate at room temperature. 210 μl (1.2 mmol, 1.2 equivalent) of ethyl-2-bromo-2-methylpropanate was added thereto. The mixture was heated at 60~90° C. with supplementing acetone for 4 hours with stirring vigorously. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 500 mg (yield: 80%) of the target compound.

$^1$H NMR (300 MHz, CDCl$_3$) δ7.66 (s, 4H), 67.43 (d, 2H), 67.22 (m, 5H), 67.03 (m, 4H), 66.50 (d, 1H), 64.28 (q, 1H), 64.19 (m, 2H), 62.12 (s, 3H), 61.54 (s, 6H), 61.19 (t, 3H).

Example 162

Preparation of Compound S162

[Process E]

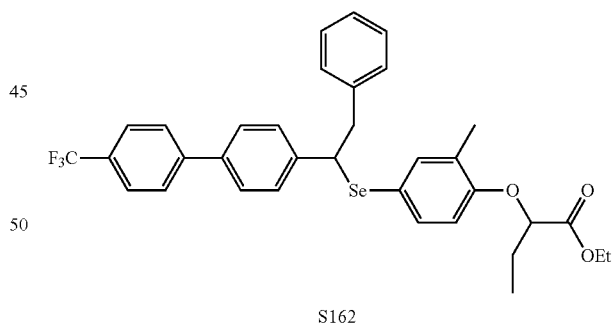

S162

511 mg (1 mmol) of the compound S159 prepared in example 159 was well mixed with 10 ml of acetone containing 5% water and 346 mg (2.5 mmol, 2.5 equivalent) of potassium carbonate at room temperature. 146 μl (1.2 mmol, 1.2 equivalent) of ethyl-2-bromobutylate was added thereto. The mixture was heated at 60~90° C. with supplementing acetone for 4 hours with stirring vigorously. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 519 mg (yield: 83%) of the target compound.

$^1$H NMR (300 MHz, CDCl$_3$) δ7.67 (s, 4H), 67.46 (d, 2H), 67.23 (m, 5H), 67.03 (m, 4H), 66.51 (d, 1H), 64.53 (t, 1H), 64.21 (m, 3H), 63.27 (m, 2H), 62.19 (s, 3H), 61.99 (m, 2H), 61.28 (t, 3H), 61.09 (t, 3H).

Example 163

Preparation of Compound S163

[Process E]

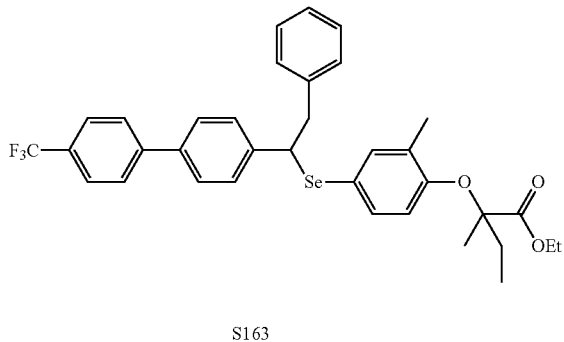

S163

511 mg (1 mmol) of the compound S159 prepared in example 159 was well mixed with 10 ml of acetone containing 5% water and 346 mg (2.5 mmol, 2.5 equivalent) of potassium carbonate at room temperature. 193 μl (1.2 mmol, 1.2 equivalent) of ethyl-2-bromo-2-methylbutylate was added thereto. The mixture was heated at 60~90° C. with supplementing acetone for 4 hours with stirring vigorously. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 512 mg (yield: 80%) of the target compound (EIMS: 641.1[M+H]$^+$).

Example 164

Preparation of Compound S164

[Process F]

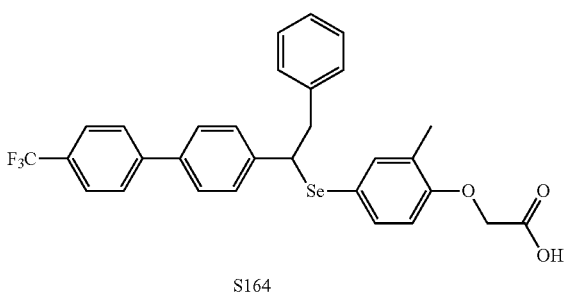

S164

597 mg (1 mmol) of the compound 5160 prepared in example 160 was mixed well with 15 ml of THF and 10 ml of water, to which 0.6 ml of 2.0 M lithium hydroxide solution was slowly added at 0° C. After stirring at 0° C. for 60 minutes, 2.5 ml of 0.5 M NaHSO$_4$ was added thereto. The organic solvent was extracted by using sodium chloride solution and ethylacetate. After filtering, the solvent was distillated under reduced pressure, and the residue was purified by LH-20 column chromatography to give 517 mg (yield: 93%) of the target compound.

$^1$H NMR (300 MHz, CDCl$_3$) δ7.67 (s, 4H), 67.45 (d, 2H), δ7.22 (m, 5H), 67.05 (m, 4H), 66.54 (d, 1H), 64.59 (s, 2H), 64.24 (m, 1H), 63.24 (m, 2H), 62.18 (s, 3H).

Example 165

Preparation of Compound S165

[Process E]

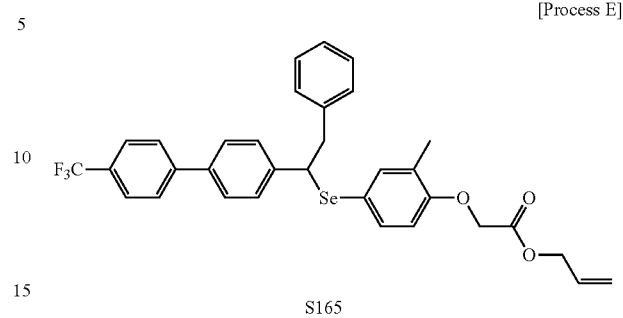

S165

511 mg (1 mmol) of the compound S159 prepared in example 159 was well mixed with 10 ml of acetone containing 5% water and 346 mg (2.5 mmol, 2.5 equivalent) of potassium carbonate at room temperature. 219 mg (1.2 mmol, 1.1 equivalent) of bromoacetateallylester was added thereto, followed by vigorous stirring for 4 hours. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 572 mg (yield: 94%) of the target compound (EIMS: 611.1 [M+H]$^+$).

Example 166

Preparation of Compound S166

[Process F]

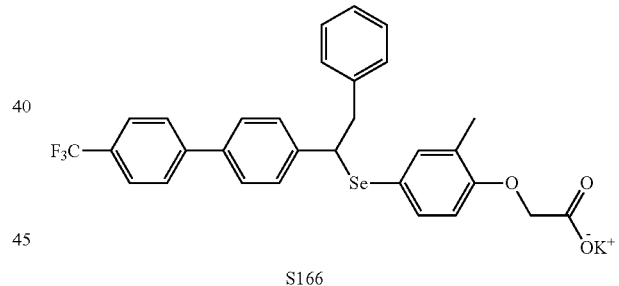

S166

504 mg (1 mmol) of the compound 5165 prepared in example 165 and 56 mg (0.05 mmol, 0.05 equivalent) of palladiumtetrakistriphenylphosphine were dissolved in 20 ml of anhydride dichloromethane, followed by stirring at room temperature. 174 mg (1 mmol, 1.0 equivalent) of potassium 2-ethylhexanoate was dissolved in 2 ml of anhydride dichloromethane, which was slowly added to the reaction solution. After stirring at room temperature for one hour, centrifugation was performed to eliminate the solvent. The solid produced thereby was washed with 20 ml of dichloromethane and 20 ml of normal hexane, followed by drying to give 547 mg (yield: 90%) of the target compound.

$^1$H NMR (300 MHz, CDCl$_3$) δ7.67 (s, 4H), 67.45 (d, 2H), 67.22 (m, 5H), 67.05 (m, 4H), 66.54 (d, 1H), 64.59 (s, 2H), 64.24 (m, 1H), 63.24 (m, 2H), 62.18 (s, 3H).

Examples 167~301

The compounds shown in Table 3 were prepared by the methods of examples 151~166 and NMRs of the compounds are same as the compounds of examples 17~149.

TABLE 3

[Structure: R2R1C*-A-[phenyl(R3)m]-O-C(R4)(R5)-C(=O)-OR6]

(R3)m group shown as para-disubstituted phenyl.

| Ex. | R1 | R2 | (R3)m phenyl | m | R4 | R5 | R6 | A |
|---|---|---|---|---|---|---|---|---|
| 167 | 4'-(F3C)-biphenyl-4-yl | 3-chloro-2-ethyl-1-fluorophenyl | 3,4-dimethylphenyl (CH3) | 1 | H | H | H | Se |
| 168 | 4'-(F3C)-biphenyl-4-yl | 2-ethyl-1,3,5-trifluorophenyl | 3,4-dimethylphenyl (CH3) | 1 | H | H | H | Se |
| 169 | 4'-(F3C)-biphenyl-4-yl | 2-ethyl-1,3-difluorophenyl | 3,4-dimethylphenyl (CH3) | 1 | H | H | H | Se |
| 170 | 4'-(F3C)-biphenyl-4-yl | 1,3-dichloro-2-ethylphenyl | 3,4-dimethylphenyl (CH3) | 1 | H | H | H | Se |
| 171 | 4'-(F3C)-biphenyl-4-yl | 2-ethyl-1-fluoro-3-(trifluoromethyl)phenyl | 3,4-dimethylphenyl (CH3) | 1 | H | H | H | Se |
| 172 | 4'-(F3C)-biphenyl-4-yl | 2-ethylphenyl | 3,4-dimethylphenyl (CH3) | 1 | H | H | H | Se |
| 173 | 4'-(F3C)-biphenyl-4-yl | 2-ethylphenyl | 3,4-dimethylphenyl (CH3) | 1 | CH3 | CH3 | H | Se |

TABLE 3-continued
| Ex. | R₁ | R₂ | (R₃)ₘ ring | m | R₄ | R₅ | R₆ | A |
|---|---|---|---|---|---|---|---|---|
| 174 | 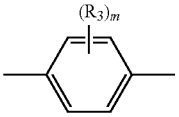 | 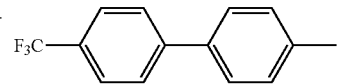 | 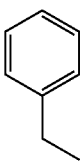 | 1 | H | CH₃CH₂ | H | Se |
| 175 | 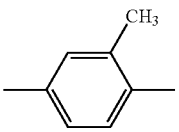 | 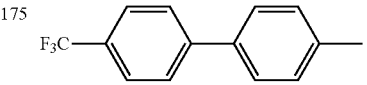 | 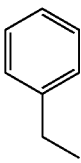 | 1 | CH₃ | CH₃CH₂ | H | Se |
| 176 | 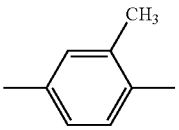 | 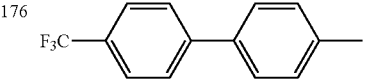 | 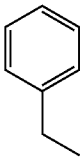 | 1 | H | H | K | Se |
| 177 | 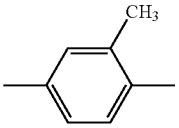 | 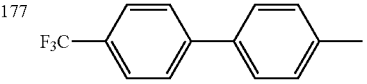 | 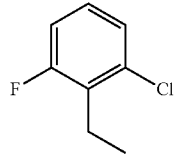 | 1 | H | H | K | Se |
| 178 | 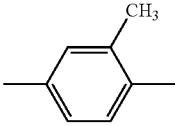 | 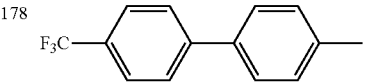 | 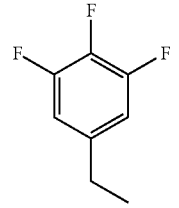 | 1 | H | H | K | Se |
| 179 | 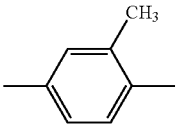 | 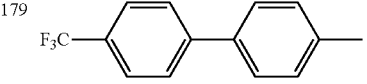 | 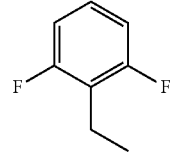 | 1 | H | H | K | Se |
| 180 | 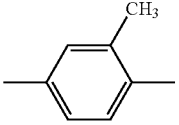 | 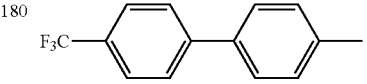 | 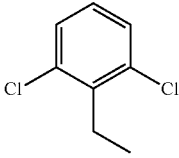 | 1 | H | H | K | Se |

TABLE 3-continued

| Ex. | R₁ | R₂ | (R₃)ₘ | m | R₄ | R₅ | R₆ | A |
|---|---|---|---|---|---|---|---|---|
| 181 | 4'-(trifluoromethyl)biphenyl-4-yl | 2-fluoro-6-(trifluoromethyl)phenyl, ethyl | 3,4-dimethylphenyl | 1 | H | H | K | Se |
| 182 | 4'-fluorobiphenyl-4-yl | phenyl | 3,4-dimethylphenyl | 1 | H | H | H | Se |
| 183 | 4'-fluorobiphenyl-4-yl | 2-chloro-6-fluorophenyl, ethyl | 3,4-dimethylphenyl | 1 | H | H | H | Se |
| 184 | 4'-fluorobiphenyl-4-yl | 2,3,4-trifluorophenyl, ethyl | 3,4-dimethylphenyl | 1 | H | H | H | Se |
| 185 | 4'-fluorobiphenyl-4-yl | 2,6-difluorophenyl, ethyl | 3,4-dimethylphenyl | 1 | H | H | H | Se |
| 186 | 4'-fluorobiphenyl-4-yl | 2,6-dichlorophenyl, ethyl | 3,4-dimethylphenyl | 1 | H | H | H | Se |
| 187 | 4'-fluorobiphenyl-4-yl | 2-fluoro-6-(trifluoromethyl)phenyl, ethyl | 3,4-dimethylphenyl | 1 | H | H | H | Se |

TABLE 3-continued
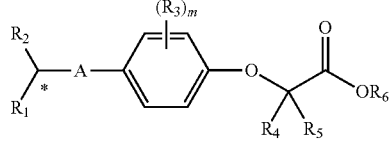
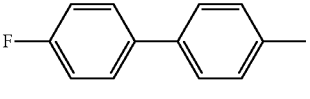
| Ex. | R₁ | R₂ | (R₃)ₘ ring | m | R₄ | R₅ | R₆ | A |
|---|---|---|---|---|---|---|---|---|
| 188 | 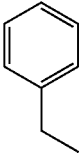 | 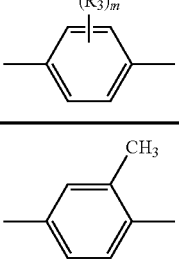 | 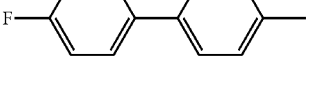 | 1 | CH₃ | CH₃ | H | Se |
| 189 | 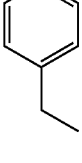 | 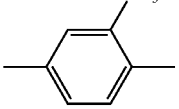 | 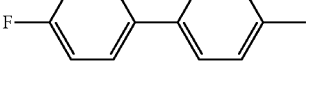 | 1 | H | CH₃CH₂ | H | Se |
| 190 | 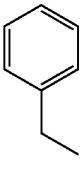 | 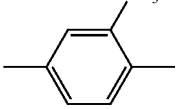 | 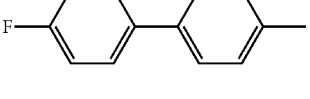 | 1 | CH₃ | CH₃CH₂ | H | Se |
| 191 | 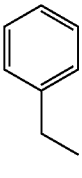 | 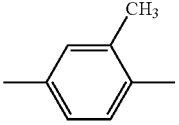 | 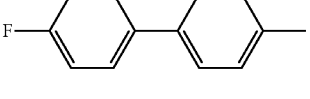 | 1 | H | H | K | Se |
| 192 | 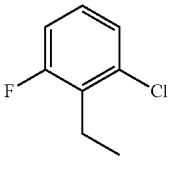 | 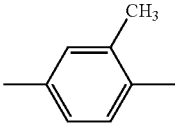 | 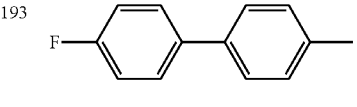 | 1 | H | H | K | Se |
| 193 | 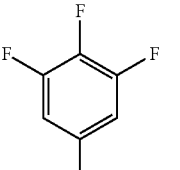 | 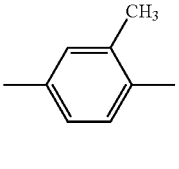 | 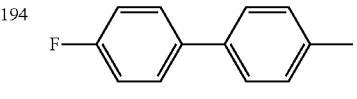 | 1 | H | H | K | Se |
| 194 | 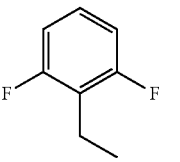 | 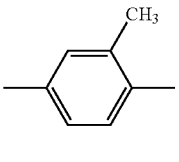 |  | 1 | H | H | K | Se |

TABLE 3-continued

| Ex. | R₁ | R₂ | (R₃)ₘ ring | m | R₄ | R₅ | R₆ | A |
|---|---|---|---|---|---|---|---|---|
| 195 | 4'-fluoro-biphenyl-4-yl | 2,6-dichloro-3-ethylphenyl | 3,4-dimethylphenyl | 1 | H | H | K | Se |
| 196 | 4'-fluoro-biphenyl-4-yl | 3-fluoro-2-ethyl-6-(trifluoromethyl)phenyl | 3,4-dimethylphenyl | 1 | H | H | K | Se |
| 197 | 3',4',5'-trifluoro-biphenyl-4-yl | 2-ethylphenyl | 3,4-dimethylphenyl | 1 | H | H | H | Se |
| 198 | 3',4',5'-trifluoro-biphenyl-4-yl | 3-fluoro-6-chloro-2-ethylphenyl | 3,4-dimethylphenyl | 1 | H | H | H | Se |
| 199 | 3',4',5'-trifluoro-biphenyl-4-yl | 2,3-difluoro-5-ethylphenyl | 3,4-dimethylphenyl | 1 | H | H | H | Se |
| 200 | 3',4',5'-trifluoro-biphenyl-4-yl | 2,6-difluoro-3-ethylphenyl | 3,4-dimethylphenyl | 1 | H | H | H | Se |
| 201 | 3',4',5'-trifluoro-biphenyl-4-yl | 2,6-dichloro-3-ethylphenyl | 3,4-dimethylphenyl | 1 | H | H | H | Se |

TABLE 3-continued

| Ex. | R₁ | R₂ | (R₃)ₘ ring | m | R₄ | R₅ | R₆ | A |
|---|---|---|---|---|---|---|---|---|
| 202 | 3,4,5-trifluorobiphenyl | 3-F-2-ethyl-1-CF₃-phenyl | 3,4-diCH₃-phenyl | 1 | H | H | H | Se |
| 203 | 3,4,5-trifluorobiphenyl | 2-ethylphenyl | 3,4-diCH₃-phenyl | 1 | CH₃ | CH₃ | H | Se |
| 204 | 3,4,5-trifluorobiphenyl | 2-ethylphenyl | 3,4-diCH₃-phenyl | 1 | H | CH₃CH₂ | H | Se |
| 205 | 3,4,5-trifluorobiphenyl | 2-ethylphenyl | 3,4-diCH₃-phenyl | 1 | CH₃ | CH₃CH₂ | H | Se |
| 206 | 3,4,5-trifluorobiphenyl | 2-ethylphenyl | 3,4-diCH₃-phenyl | 1 | H | H | K | Se |
| 207 | 3,4,5-trifluorobiphenyl | 3-F-2-ethyl-1-Cl-phenyl | 3,4-diCH₃-phenyl | 1 | H | H | K | Se |
| 208 | 3,4,5-trifluorobiphenyl | 2,3-diF-5-ethyl-phenyl | 3,4-diCH₃-phenyl | 1 | H | H | K | Se |

TABLE 3-continued

| Ex. | R₁ | R₂ | (R₃)ₘ ring | m | R₄ | R₅ | R₆ | A |
|---|---|---|---|---|---|---|---|---|
| 209 | 3,4,5-trifluorobiphenyl-4'-yl | 2,6-difluorophenyl-ethyl | 3,4-dimethylphenyl (CH₃) | 1 | H | H | K | Se |
| 210 | 3,4,5-trifluorobiphenyl-4'-yl | 2,6-dichlorophenyl-ethyl | 3,4-dimethylphenyl (CH₃) | 1 | H | H | K | Se |
| 211 | 3,4,5-trifluorobiphenyl-4'-yl | 2-fluoro-6-trifluoromethylphenyl-ethyl | 3,4-dimethylphenyl (CH₃) | 1 | H | H | K | Se |
| 212 | biphenyl-4-yl | phenyl-ethyl | 3,4-dimethylphenyl (CH₃) | 1 | H | H | H | Se |
| 213 | biphenyl-4-yl | 3-fluoro-chlorophenyl-ethyl | 3,4-dimethylphenyl (CH₃) | 1 | H | H | H | Se |
| 214 | biphenyl-4-yl | 3,4,5-trifluorophenyl-ethyl | 3,4-dimethylphenyl (CH₃) | 1 | H | H | H | Se |
| 215 | biphenyl-4-yl | 2,6-difluorophenyl-ethyl | 3,4-dimethylphenyl (CH₃) | 1 | H | H | H | Se |

TABLE 3-continued
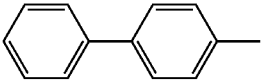
| Ex. | R₁ | R₂ | (R₃)ₘ ring | m | R₄ | R₅ | R₆ | A |
|---|---|---|---|---|---|---|---|---|
| 216 | 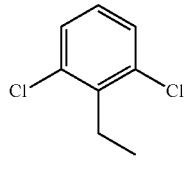 | 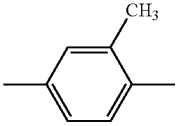 | 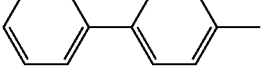 | 1 | H | H | H | Se |
| 217 | 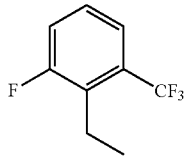 | 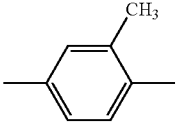 | 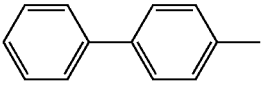 | 1 | H | H | H | Se |
| 218 | 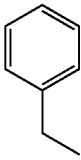 | 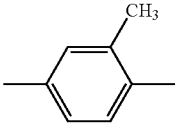 | 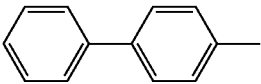 | 1 | CH₃ | CH₃ | H | Se |
| 219 | 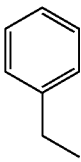 | 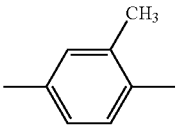 | 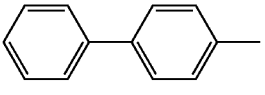 | 1 | H | CH₃CH₂ | H | Se |
| 220 | 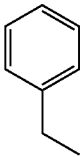 | 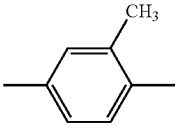 | 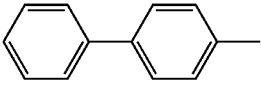 | 1 | CH₃ | CH₃CH₂ | H | Se |
| 221 | 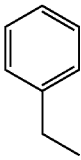 | 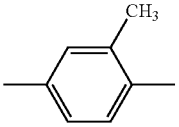 | 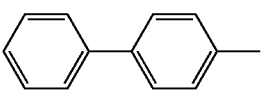 | 1 | H | H | K | Se |
| 222 | 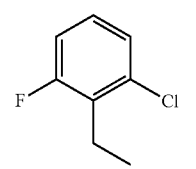 | 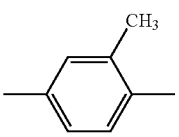 | | 1 | H | H | K | Se |

TABLE 3-continued
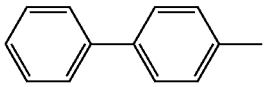
| Ex. | R₁ | R₂ | (R₃)ₘ ring | m | R₄ | R₅ | R₆ | A |
|---|---|---|---|---|---|---|---|---|
| 223 | 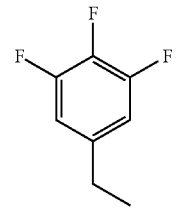 | 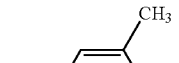 | 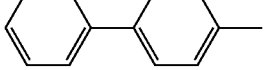 | 1 | H | H | K | Se |
| 224 | 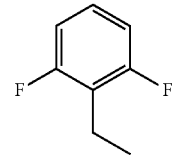 | 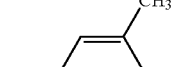 | 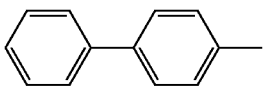 | 1 | H | H | K | Se |
| 225 | 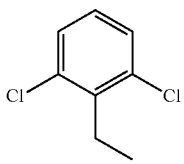 | 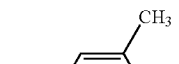 | 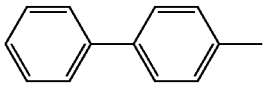 | 1 | H | H | K | Se |
| 226 | 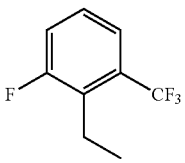 | 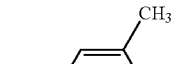 | 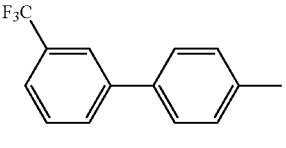 | 1 | H | H | K | Se |
| 227 | 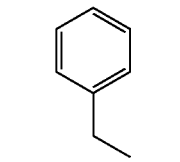 | 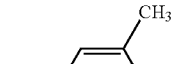 | 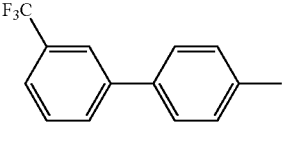 | 1 | H | H | H | Se |
| 228 | 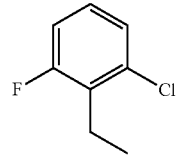 | 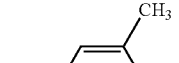 | 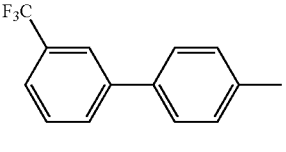 | 1 | H | H | H | Se |
| 229 | 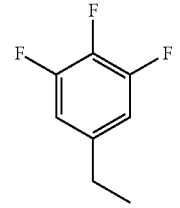 | 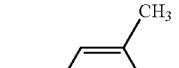 | | 1 | H | H | H | Se |

TABLE 3-continued
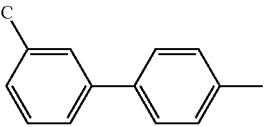
| Ex. | R₁ | R₂ | (R₃)ₘ ring | m | R₄ | R₅ | R₆ | A |
|---|---|---|---|---|---|---|---|---|
| 230 |  | 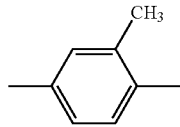 | 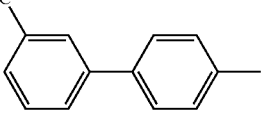 | 1 | H | H | H | Se |
| 231 | 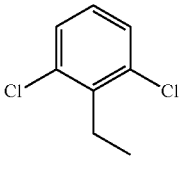 | 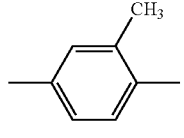 | 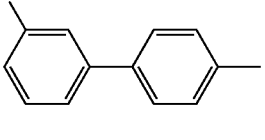 | 1 | H | H | H | Se |
| 232 | 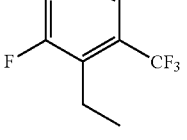 | 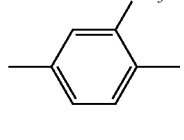 | 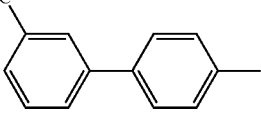 | 1 | H | H | H | Se |
| 233 | 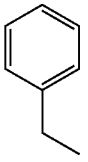 | 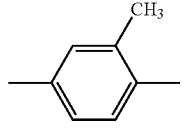 | 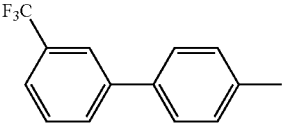 | 1 | CH₃ | CH₃ | H | Se |
| 234 | 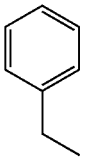 | 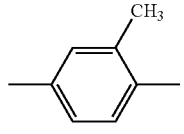 | 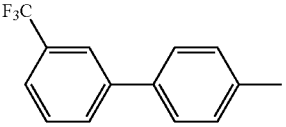 | 1 | H | CH₃CH₂ | H | Se |
| 235 | 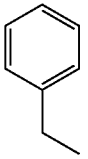 | 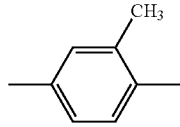 | 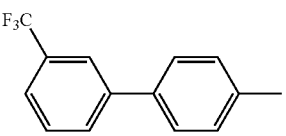 | 1 | CH₃ | CH₃CH₂ | H | Se |
| 236 | 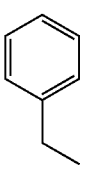 | 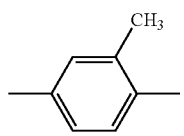 | | 1 | H | H | K | Se |

TABLE 3-continued
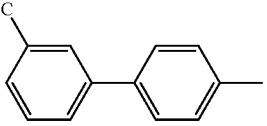
| Ex. | R₁ | R₂ | (R₃)ₘ | m | R₄ | R₅ | R₆ | A |
|---|---|---|---|---|---|---|---|---|
| 237 | 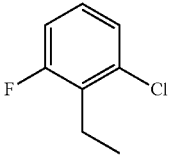 | 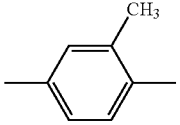 | 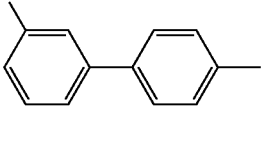 | 1 | H | H | K | Se |
| 238 | 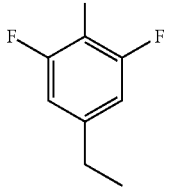 | 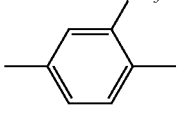 | 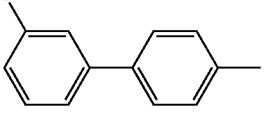 | 1 | H | H | K | Se |
| 239 | 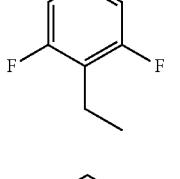 | 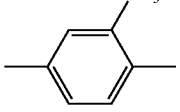 | 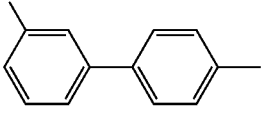 | 1 | H | H | K | Se |
| 240 | 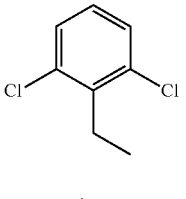 | 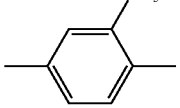 | 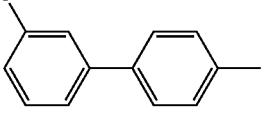 | 1 | H | H | K | Se |
| 241 | 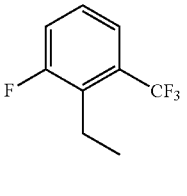 | 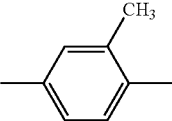 | 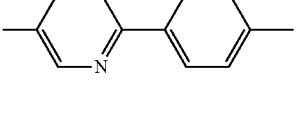 | 1 | H | H | K | Se |
| 242 | 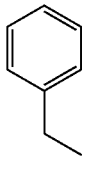 | 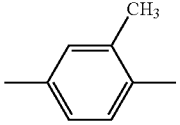 | 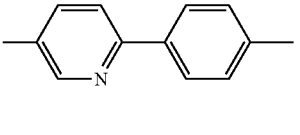 | 1 | H | H | H | Se |
| 243 | 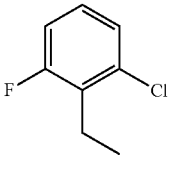 | 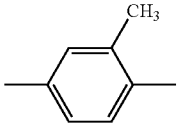 | | 1 | H | H | H | Se |

TABLE 3-continued

| Ex. | R₁ | R₂ | (R₃)ₘ ring | m | R₄ | R₅ | R₆ | A |
|---|---|---|---|---|---|---|---|---|
| 244 | 5-(F₃C)-pyridin-2-yl-phenyl | 3,4,5-trifluorophenyl-CH₂ | 3,4-dimethylphenyl | 1 | H | H | H | Se |
| 245 | 5-(F₃C)-pyridin-2-yl-phenyl | 2,6-difluorophenyl-CH₂ | 3,4-dimethylphenyl | 1 | H | H | H | Se |
| 246 | 5-(F₃C)-pyridin-2-yl-phenyl | 2,6-dichlorophenyl-CH₂ | 3,4-dimethylphenyl | 1 | H | H | H | Se |
| 247 | 5-(F₃C)-pyridin-2-yl-phenyl | 2-F-6-CF₃-phenyl-CH₂ | 3,4-dimethylphenyl | 1 | H | H | H | Se |
| 248 | 5-(F₃C)-pyridin-2-yl-phenyl | phenyl-CH₂ | 3,4-dimethylphenyl | 1 | CH₃ | H | H | Se |
| 249 | 5-(F₃C)-pyridin-2-yl-phenyl | phenyl-CH₂ | 3,4-dimethylphenyl | 1 | CH₃ | CH₃CH₂ | H | Se |
| 250 | 5-(F₃C)-pyridin-2-yl-phenyl | phenyl-CH₂ | 3,4-dimethylphenyl | 1 | CH₃ | CH₃CH₂ | H | Se |

TABLE 3-continued

| Ex. | R₁ | R₂ | (R₃)ₘ | m | R₄ | R₅ | R₆ | A |
|---|---|---|---|---|---|---|---|---|
| 251 | 5-(trifluoromethyl)pyridin-2-yl-phenyl- | phenyl- | 3,4-dimethyl | 1 | H | H | K | Se |
| 252 | 5-(trifluoromethyl)pyridin-2-yl-phenyl- | 3-fluoro-2-chlorophenyl- | 3,4-dimethyl | 1 | H | H | K | Se |
| 253 | 5-(trifluoromethyl)pyridin-2-yl-phenyl- | 2,3,4-trifluorophenyl- | 3,4-dimethyl | 1 | H | H | K | Se |
| 254 | 5-(trifluoromethyl)pyridin-2-yl-phenyl- | 2,6-difluorophenyl- | 3,4-dimethyl | 1 | H | H | K | Se |
| 255 | 5-(trifluoromethyl)pyridin-2-yl-phenyl- | 2,6-dichlorophenyl- | 3,4-dimethyl | 1 | H | H | K | Se |
| 256 | 5-(trifluoromethyl)pyridin-2-yl-phenyl- | 2-fluoro-6-trifluoromethylphenyl- | 3,4-dimethyl | 1 | H | H | K | Se |
| 257 | 5-(trifluoromethyl)pyridin-2-yl-phenyl- | phenyl- | 3,4-dimethyl | 1 | H | H | H | Se |

TABLE 3-continued

| Ex. | R₁ | R₂ | (R₃)ₘ | m | R₄ | R₅ | R₆ | A |
|---|---|---|---|---|---|---|---|---|
| 258 | 4-(F₃C)phenyl-2-(5-methyl)pyridyl | 2-chloro-6-fluoro-3-ethylphenyl | 2,4-dimethylphenyl | 1 | H | H | H | Se |
| 259 | 4-(F₃C)phenyl-2-(5-methyl)pyridyl | 3,4,5-trifluorophenyl-ethyl | 2,4-dimethylphenyl | 1 | H | H | H | Se |
| 260 | 4-(F₃C)phenyl-2-(5-methyl)pyridyl | 2,6-difluoro-3-ethylphenyl | 2,4-dimethylphenyl | 1 | H | H | H | Se |
| 261 | 4-(F₃C)phenyl-2-(5-methyl)pyridyl | 2,6-dichloro-3-ethylphenyl | 2,4-dimethylphenyl | 1 | H | H | H | Se |
| 262 | 4-(F₃C)phenyl-2-(5-methyl)pyridyl | 2-fluoro-6-(CF₃)-3-ethylphenyl | 2,4-dimethylphenyl | 1 | H | H | H | Se |
| 263 | 4-(F₃C)phenyl-2-(5-methyl)pyridyl | 2-ethylphenyl | 2,4-dimethylphenyl | 1 | H | H | H | Se |
| 264 | 4-(F₃C)phenyl-2-(5-methyl)pyridyl | 2-ethylphenyl | 2,4-dimethylphenyl | 1 | H | CH₃CH₂ | H | Se |

TABLE 3-continued
| Ex. | R₁ | R₂ | (R₃)ₘ | m | R₄ | R₅ | R₆ | A |
|---|---|---|---|---|---|---|---|---|
| 265 | 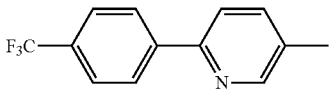 | 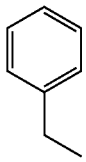 | 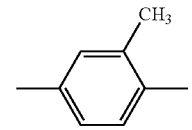 | 1 | CH₃ | CH₃CH₂ | H | Se |
| 266 | 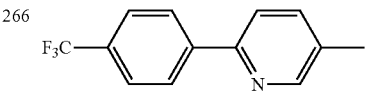 | 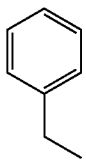 | 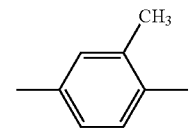 | 1 | H | H | K | Se |
| 267 | 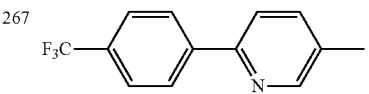 | 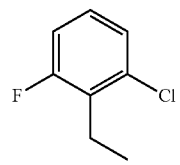 | 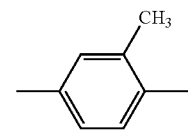 | 1 | H | H | K | Se |
| 268 | 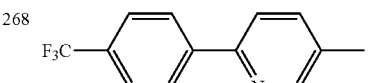 | 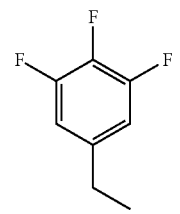 | 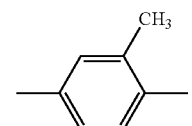 | 1 | H | H | K | Se |
| 269 | 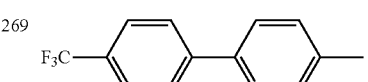 |  | 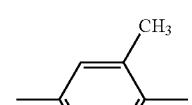 | 1 | H | H | K | Se |
| 270 | 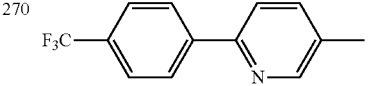 | 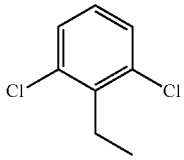 | 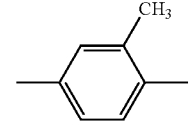 | 1 | H | H | K | Se |
| 271 | 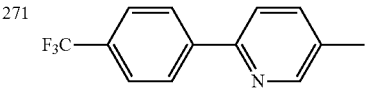 | 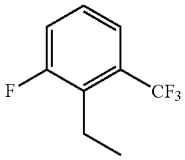 | 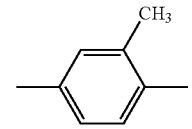 | 1 | H | H | K | Se |

TABLE 3-continued

| Ex. | R₁ | R₂ | (R₃)ₘ | m | R₄ | R₅ | R₆ | A |
|---|---|---|---|---|---|---|---|---|
| 272 | 4-(F₃C)-phenyl-(5-methylisoxazol-3-yl) | phenyl | 3,4-dimethyl | 1 | H | H | H | Se |
| 273 | 4-(F₃C)-phenyl-(5-methylisoxazol-3-yl) | 2-F,6-Cl-phenyl | 3,4-dimethyl | 1 | H | H | H | Se |
| 274 | 4-(F₃C)-phenyl-(5-methylisoxazol-3-yl) | 2,3,4-triF-phenyl | 3,4-dimethyl | 1 | H | H | H | Se |
| 275 | 4-(F₃C)-phenyl-(5-methylisoxazol-3-yl) | 2,6-diF-phenyl | 3,4-dimethyl | 1 | H | H | H | Se |
| 276 | 4-(F₃C)-phenyl-(5-methylisoxazol-3-yl) | 2,6-diCl-phenyl | 3,4-dimethyl | 1 | H | H | H | Se |
| 277 | 4-(F₃C)-phenyl-(5-methylisoxazol-3-yl) | 2-F,6-CF₃-phenyl | 3,4-dimethyl | 1 | H | H | H | Se |
| 278 | 4-(F₃C)-phenyl-(5-methylisoxazol-3-yl) | phenyl | 3,4-dimethyl | 1 | CH₃ | CH₃ | H | Se |

TABLE 3-continued

| Ex. | R₁ | R₂ | (R₃)ₘ aryl | m | R₄ | R₅ | R₆ | A |
|---|---|---|---|---|---|---|---|---|
| 279 | 3-(4-trifluoromethylphenyl)-5-methylisoxazole | phenyl | 3,4-dimethylphenyl | 1 | H | CH₃CH₂ | H | Se |
| 280 | 3-(4-trifluoromethylphenyl)-5-methylisoxazole | phenyl | 3,4-dimethylphenyl | 1 | CH₃ | CH₃CH₂ | H | Se |
| 281 | 3-(4-trifluoromethylphenyl)-5-methylisoxazole | phenyl | 3,4-dimethylphenyl | 1 | H | H | K | Se |
| 282 | 3-(4-trifluoromethylphenyl)-5-methylisoxazole | 2-chloro-6-fluorophenyl | 3,4-dimethylphenyl | 1 | H | H | K | Se |
| 283 | 3-(4-trifluoromethylphenyl)-5-methylisoxazole | 2,3,4-trifluorophenyl | 3,4-dimethylphenyl | 1 | H | H | K | Se |
| 284 | 3-(4-trifluoromethylphenyl)-5-methylisoxazole | 2,6-difluorophenyl | 3,4-dimethylphenyl | 1 | H | H | K | Se |
| 285 | 3-(4-trifluoromethylphenyl)-5-methylisoxazole | 2,6-dichlorophenyl | 3,4-dimethylphenyl | 1 | H | H | K | Se |

TABLE 3-continued

| Ex. | R₁ | R₂ | (R₃)ₘ | m | R₄ | R₅ | R₆ | A |
|---|---|---|---|---|---|---|---|---|
| 286 | 3-(4-trifluoromethylphenyl)-5-methylisoxazol-yl | 2-fluoro-6-trifluoromethyl-3-ethylphenyl | 3-methyl-4-ethylphenyl | 1 | H | H | K | Se |
| 287 | 4-phenoxyphenyl | phenyl | 3-methyl-4-ethylphenyl | 1 | H | H | H | Se |
| 288 | 4-phenoxyphenyl | 2-fluoro-6-chloro-3-ethylphenyl | 3-methyl-4-ethylphenyl | 1 | H | H | H | Se |
| 289 | 4-phenoxyphenyl | 2,3,4-trifluoro-5-ethylphenyl | 3-methyl-4-ethylphenyl | 1 | H | H | H | Se |
| 290 | 4-phenoxyphenyl | 2,6-difluoro-3-ethylphenyl | 3-methyl-4-ethylphenyl | 1 | H | H | H | Se |
| 291 | 4-phenoxyphenyl | 2,6-dichloro-3-ethylphenyl | 3-methyl-4-ethylphenyl | 1 | H | H | H | Se |
| 292 | 4-phenoxyphenyl | 2-fluoro-6-trifluoromethyl-3-ethylphenyl | 3-methyl-4-ethylphenyl | 1 | H | H | H | Se |

TABLE 3-continued

| Ex. | R₁ | R₂ | (R₃)ₘ ring | m | R₄ | R₅ | R₆ | A |
|---|---|---|---|---|---|---|---|---|
| 293 | 4-phenoxyphenyl | benzyl | 3,4-dimethylphenyl | 1 | CH₃ | CH₃ | H | Se |
| 294 | 4-phenoxyphenyl | benzyl | 3,4-dimethylphenyl | 1 | H | CH₃CH₂ | H | Se |
| 295 | 4-phenoxyphenyl | benzyl | 3,4-dimethylphenyl | 1 | CH₃ | CH₃CH₂ | H | Se |
| 296 | 4-phenoxyphenyl | benzyl | 3,4-dimethylphenyl | 1 | H | H | K | Se |
| 297 | 4-phenoxyphenyl | 2-chloro-6-fluorobenzyl | 3,4-dimethylphenyl | 1 | H | H | K | Se |
| 298 | 4-phenoxyphenyl | 3,4,5-trifluorobenzyl | 3,4-dimethylphenyl | 1 | H | H | K | Se |
| 299 | 4-phenoxyphenyl | 2,6-difluorobenzyl | 3,4-dimethylphenyl | 1 | H | H | K | Se |

TABLE 3-continued

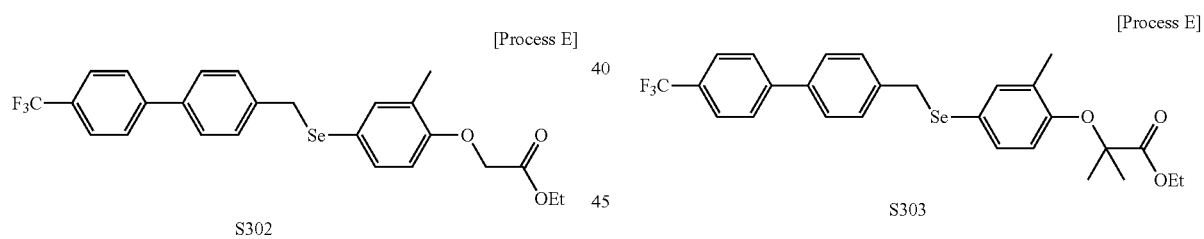

| Ex. | R₁ | R₂ | (R₃)ₘ aryl | m | R₄ | R₅ | R₆ | A |
|---|---|---|---|---|---|---|---|---|
| 300 | phenyl-O-(4-tolyl)- | 2,6-dichloro-(ethyl)phenyl- | 3,4-dimethylphenyl-CH₃ | 1 | H | H | K | Se |
| 301 | phenyl-O-(4-tolyl)- | 2-F-6-CF₃-(ethyl)phenyl- | 3,4-dimethylphenyl-CH₃ | 1 | H | H | K | Se |

Example 302

Preparation of Compound S302

[Process E]

S302

421 mg (1 mmol) of the compound S151 prepared in example 151 was well mixed with 10 ml of acetone containing 5% water and 346 mg (2.5 mmol, 2.5 equivalent) of potassium carbonate at room temperature. 134 μl (1.2 mmol, 1.2 equivalent) of bromoacetateethylester was added thereto, followed by vigorous stirring for 4 hours. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 472 mg (yield: 93%) of the target compound.

$^1$H NMR (300 MHz, CDCl₃) δ7.66 (d, 4H), 67.46 (d, 2H), 67.23 (m, 4H), 66.57 (d, 1H), 64.61 (s, 2H), 64.25 (q, 2H), 64.04 (s, 2H), 62.23 (s, 3H), 61.28 (s, 3H).

Example 303

Preparation of Compound S303

[Process E]

S303

421 mg (1 mmol) of the compound S151 prepared in example 151 was well mixed with 10 ml of acetone containing 5% water and 346 mg (2.5 mmol, 2.5 equivalent) of potassium carbonate at room temperature. 210 μl (1.2 mmol, 1.2 equivalent) of ethyl-2-bromo-2-methylpropanate was added thereto. The mixture was heated at 60~90° C. with supplementing acetone for 4 hours with stirring vigorously. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 428 mg (yield: 80%) of the target compound.

$^1$H NMR (300 MHz, CDCl₃) δ7.66 (d, 4H), 67.46 (d, 2H), 67.23 (m, 4H), 66.57 (d, 1H), 64.25 (q, 2H), 64.04 (s, 2H), 62.23 (s, 3H), 61.56 (s, 6H), 61.28 (s, 3H).

Example 304

Preparation of Compound S304

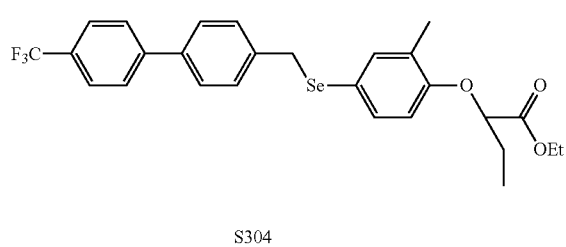

S304

[Process E]

421 mg (1 mmol) of the compound S151 prepared in example 151 was well mixed with 10 ml of acetone containing 5% water and 346 mg (2.5 mmol, 2.5 equivalent) of potassium carbonate at room temperature. 146 µl (1.2 mmol, 1.2 equivalent) of ethyl-2-bromobutylate was added thereto. The mixture was heated at 60~90° C. with supplementing acetone for 4 hours with stirring vigorously. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 444 mg (yield: 83%) of the target compound.

$^1$H NMR (300 MHz, CDCl$_3$) δ7.66 (d, 4H), 67.46 (d, 2H), δ7.23 (m, 4H), 66.57 (d, 1H), 64.33 (t, 1H), 64.25 (q, 2H), 64.04 (s, 2H), 62.23 (s, 3H), 62.00 (m, 2H), 61.56 (s, 6H), 61.28 (s, 3H), 61.25 (m, 3H).

Example 305

Preparation of Compound S305

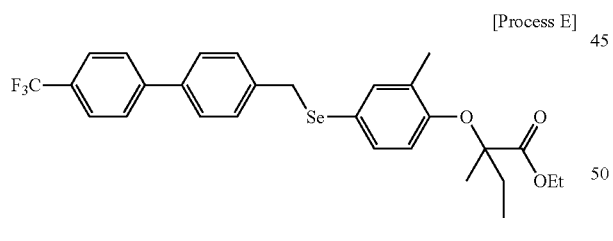

S305

[Process E]

421 mg (1 mmol) of the compound S151 prepared in example 151 was well mixed with 10 ml of acetone containing 5% water and 346 mg (2.5 mmol, 2.5 equivalent) of potassium carbonate at room temperature. 193 µl (1.2 mmol, 1.2 equivalent) of ethyl-2-bromo-2-methylbutylate was added thereto. The mixture was heated at 60~90° C. with supplementing acetone for 4 hours with stirring vigorously. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 440 mg (yield: 80%) of the target compound (EIMS: 551.1[M+H]$^+$).

Example 306

Preparation of Compound S306

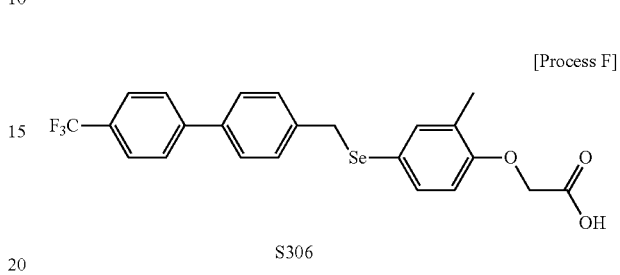

S306

[Process F]

460 mg (1 mmol) of the compound 5302 prepared in example 302 was mixed well with 15 ml of THF and 10 ml of water, to which 0.6 ml of 2.0 M lithium hydroxide solution was slowly added at 0° C. After stirring at 0° C. for 60 minutes, 2.5 ml of 0.5 M NaHSO$_4$ was added thereto. The organic solvent was extracted by using sodium chloride solution and ethylacetate. After filtering, the solvent was distillated under reduced pressure, and the residue was purified by LH-20 column chromatography to give 472 mg (yield: 93%) of the target compound.

$^1$H NMR (300 MHz, CDCl$_3$) δ7.66 (d, 4H), 67.46 (d, 2H), 67.23 (m, 4H), 66.57 (d, 1H), 64.61 (s, 2H), 64.04 (s, 2H), 62.22 (s, 3H).

Example 307

Preparation of Compound S307

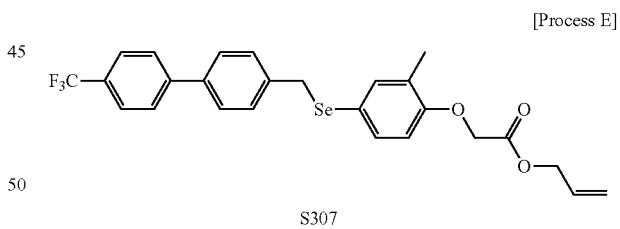

S307

[Process E]

421 mg (1 mmol) of the compound S151 prepared in example 151 was well mixed with 10 ml of acetone containing 5% water and 346 mg (2.5 mmol, 2.5 equivalent) of potassium carbonate at room temperature. 219 mg (1.2 mmol, 1.2 equivalent) of bromoacetateallylester was added thereto, followed by vigorous stirring for 4 hours. Upon completion of the reaction, the organic solvent was extracted by using sodium chloride solution and ethylacetate, which was dried over magnesium sulfate to eliminate moisture of the organic layer. After filtering, the solvent was distillated under reduced pressure, and the residue was purified by silica gel column chromatography using hexane/ethylacetate(v/v=5:1) to give 467 mg (yield: 90%) of the target compound (EIMS: 521.1 [M+H]$^+$).

Example 308

Preparation of Compound S308

[Process F]

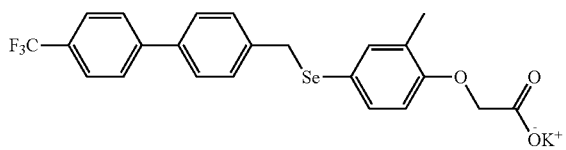
S308

519 mg (1 mmol) of the compound 5307 prepared in example 307 and 56 mg (0.05 mmol, 0.05 equivalent) of palladiumtetrakistriphenylphosphine were dissolved in 20 ml of anhydride dichloromethane, followed by stirring at room temperature. 174 mg (1 mmol, 1.0 equivalent) of potassium 2-ethylhexanoate was dissolved in 2 ml of anhydride dichloromethane, which was slowly added to the reaction solution. After stirring at room temperature for one hour, centrifugation was performed to eliminate the solvent. The solid produced thereby was washed with 20 ml of dichloromethane and 20 ml of normal hexane, followed by drying to give 471 mg (yield: 91%) of the target compound.

$^1$H NMR (300 MHz, CDCl$_3$) δ7.66 (d, 4H), 67.46 (d, 2H), 67.23 (m, 4H), 66.57 (d, 1H), 64.61 (s, 2H), 64.04 (s, 2H), 62.22 (s, 3H).

Examples 309~348

The compounds shown in Table 4 were prepared by the methods of examples 302-308 and NMR of each compound is shown in Table 5.

TABLE 4

| Ex. | R$_1$ | R$_2$ | (R$_3$)$_m$ ring | m | R$_4$ | R$_5$ | R$_6$ | A |
|---|---|---|---|---|---|---|---|---|
| 309 | F-biphenyl- | H | 2-CH$_3$ phenyl | 1 | H | H | H | Se |
| 310 | F-biphenyl- | H | 2-CH$_3$ phenyl | 1 | CH$_3$ | CH$_3$ | H | Se |
| 311 | F-biphenyl- | H | 2-CH$_3$ phenyl | 1 | H | CH$_3$CH$_2$ | H | Se |
| 312 | F-biphenyl- | H | 2-CH$_3$ phenyl | 1 | CH$_3$ | CH$_3$CH$_2$ | H | Se |
| 313 | F-biphenyl- | H | 2-CH$_3$ phenyl | 1 | H | H | K | Se |

TABLE 4-continued

| Ex. | R₁ | R₂ | (R₃)ₘ ring | m | R₄ | R₅ | R₆ | A |
|---|---|---|---|---|---|---|---|---|
| 314 | 3,4,5-trifluorobiphenyl-4'-yl | H | 3,4-dimethylphenyl (CH₃ at 3) | 1 | H | H | H | Se |
| 315 | 3,4,5-trifluorobiphenyl-4'-yl | H | 3,4-dimethylphenyl (CH₃ at 3) | 1 | CH₃ | CH₃ | H | Se |
| 316 | 3,4,5-trifluorobiphenyl-4'-yl | H | 3,4-dimethylphenyl (CH₃ at 3) | 1 | H | CH₃CH₂ | H | Se |
| 317 | 3,4,5-trifluorobiphenyl-4'-yl | H | 3,4-dimethylphenyl (CH₃ at 3) | 1 | CH₃ | CH₃CH₂ | H | Se |
| 318 | 3,4,5-trifluorobiphenyl-4'-yl | H | 3,4-dimethylphenyl (CH₃ at 3) | 1 | H | H | K | Se |
| 319 | biphenyl-4-yl | H | 3,4-dimethylphenyl (CH₃ at 3) | 1 | H | H | H | Se |
| 320 | biphenyl-4-yl | H | 3,4-dimethylphenyl (CH₃ at 3) | 1 | CH₃ | CH₃ | H | Se |
| 321 | biphenyl-4-yl | H | 3,4-dimethylphenyl (CH₃ at 3) | 1 | H | CH₃CH₂ | H | Se |

TABLE 4-continued
| Ex. | R₁ | R₂ | (R₃)ₘ | m | R₄ | R₅ | R₆ | A |
|---|---|---|---|---|---|---|---|---|
| 322 | 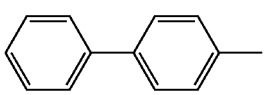 | H | 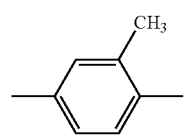 | 1 | CH₃ | CH₃CH₂ | H | Se |
| 323 | 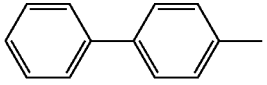 | H | 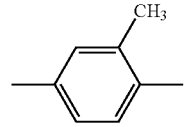 | 1 | H | H | K | Se |
| 324 | 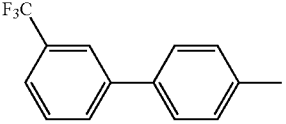 | H | 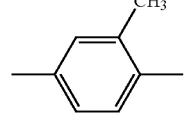 | 1 | H | H | H | Se |
| 325 | 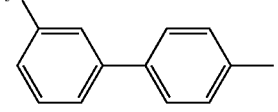 | H | 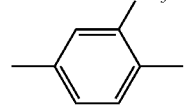 | 1 | CH₃ | CH₃ | H | Se |
| 326 | 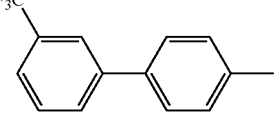 | H | 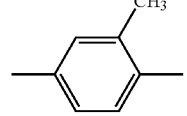 | 1 | H | CH₃CH₂ | H | Se |
| 327 | 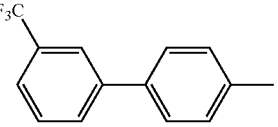 | H | 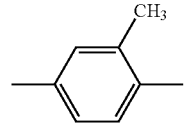 | 1 | CH₃ | CH₃CH₂ | H | Se |
| 328 | 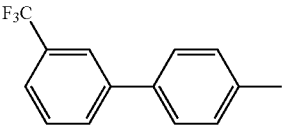 | H | 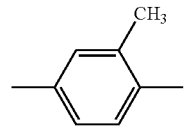 | 1 | H | H | K | Se |
| 329 | 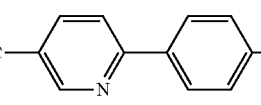 | H | 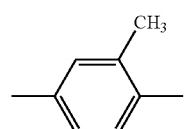 | 1 | H | H | H | Se |
| 330 | 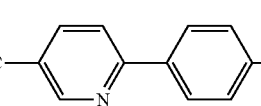 | H | 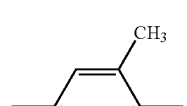 | 1 | CH₃ | CH₃ | H | Se |

TABLE 4-continued
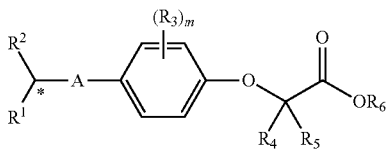
| Ex. | R₁ | R₂ | (R₃)ₘ | m | R₄ | R₅ | R₆ | A |
|---|---|---|---|---|---|---|---|---|
| 331 | 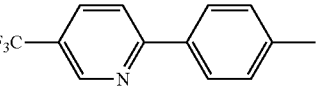 | H | 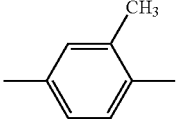 | 1 | H | CH₃CH₂ | H | Se |
| 332 | 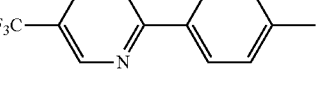 | H | 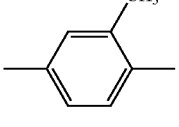 | 1 | CH₃ | CH₃CH₂ | H | Se |
| 333 | 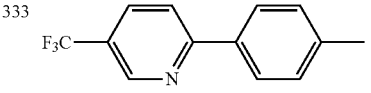 | H | 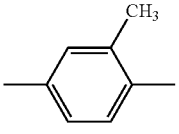 | 1 | H | H | K | Se |
| 334 | 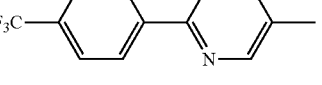 | H | 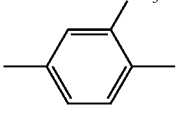 | 1 | H | H | H | Se |
| 335 | 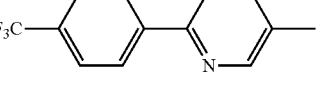 | H | 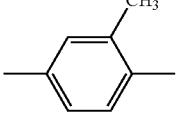 | 1 | CH₃ | CH₃ | H | Se |
| 336 | 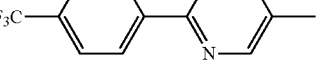 | H | 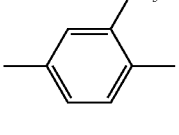 | 1 | H | CH₃CH₂ | H | Se |
| 337 | 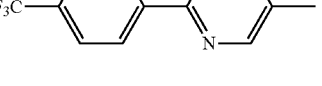 | H | 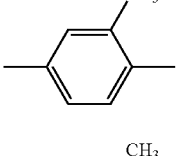 | 1 | CH₃ | CH₃CH₂ | H | Se |
| 338 | 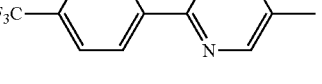 | H | 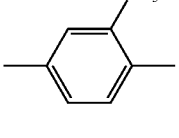 | 1 | H | H | K | Se |
| 339 | 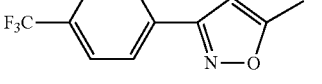 | H | 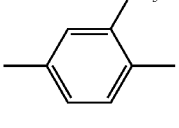 | 1 | H | H | H | Se |

TABLE 4-continued
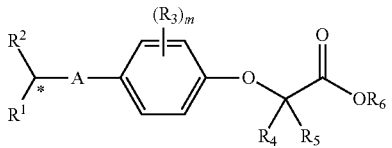
| Ex. | R₁ | R₂ | (R₃)ₘ | m | R₄ | R₅ | R₆ | A |
|---|---|---|---|---|---|---|---|---|
| 340 | 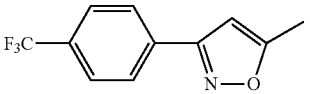 | H | 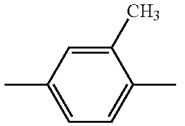 | 1 | CH₃ | CH₃ | H | Se |
| 341 | 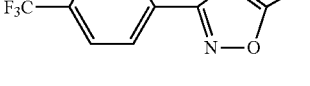 | H | 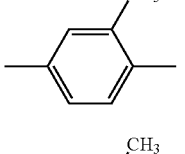 | 1 | H | CH₃CH₂ | H | Se |
| 342 | 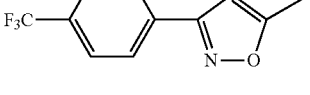 | H | 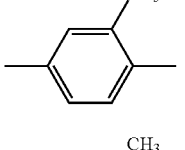 | 1 | CH₃ | CH₃CH₂ | H | Se |
| 343 | 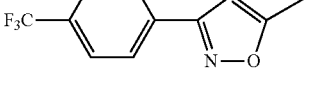 | H | 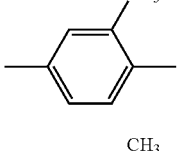 | 1 | H | H | K | Se |
| 344 | 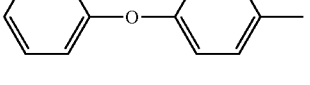 | H | 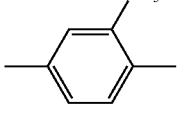 | 1 | H | H | H | Se |
| 345 | 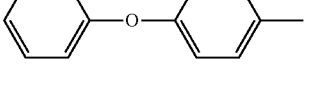 | H | 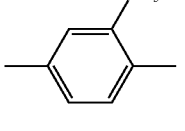 | 1 | CH₃ | CH₃ | H | Se |
| 346 | 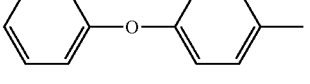 | H | 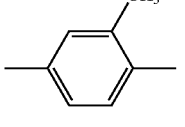 | 1 | H | CH₃CH₂ | H | Se |
| 347 | 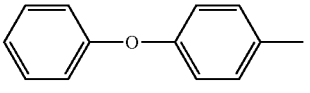 | H | 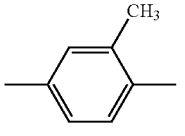 | 1 | CH₃ | CH₃CH₂ | H | Se |
| 348 | 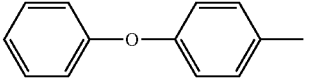 | H | 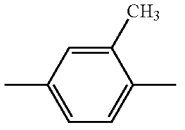 | 1 | H | H | K | Se |

TABLE 5

| Ex. | $^1$H-NMR |
| --- | --- |
| 309 | δ 7.52 (m, 2H), 7.40 (d, 2H), 7.24 (d, 2H), 7.18 (d, 2H), 7.09 (t, 2H), 6.57 (d, 1H), 4.61 (s, 2H), 4.04 (s, 2H), 2.22 (s, 3H). |
| 313 | δ 7.52 (m, 2H), 7.40 (d, 2H), 7.24 (d, 2H), 7.18 (d, 2H), 7.09 (t, 2H), 6.57 (d, 1H), 4.61 (s, 2H), 4.04 (s, 2H), 2.22 (s, 3H). |
| 314 | δ 7.34 (d, 2H), 7.24~7.13 (m, 6H), 6.57 (d, 1H), 4.61 (s, 2H), 4.02 (s, 2H), 2.23 (s, 3H). |
| 318 | δ 7.34 (d, 2H), 7.24~7.13 (m, 6H), 6.57 (d, 1H), 4.61 (s, 2H), 4.02 (s, 2H), 2.23 (s, 3H). |
| 319 | δ 7.56 (d, 2H), 7.43 (m, 4H), 7.32 (t, 1H), 7.22 (m, 4H), 6.56 (d, 1H), 4.61 (s, 2H), 4.04 (s, 2H), 2.23 (s, 3H). |
| 323 | δ 7.56 (d, 2H), 7.43 (m, 4H), 7.32 (t, 1H), 7.22 (m, 4H), 6.56 (d, 1H), 4.61 (s, 2H), 4.04 (s, 2H), 2.23 (s, 3H). |
| 324 | δ 7.72 (m, 2H), 7.59~7.42 (m, 7H), 7.21 (d, 1H), 6.59 (d, 1H), 4.61 (s, 2H), 4.04 (s, 2H), 2.23 (s, 3H). |
| 328 | δ 7.72 (m, 2H), 7.59~7.42 (m, 7H), 7.21 (d, 1H), 6.59 (d, 1H), 4.61 (s, 2H), 4.04 (s, 2H), 2.23 (s, 3H). |
| 329 | δ 8.94 (s, 1H), 8.04 (q, 1H), 7.77 (d, 1H), 7.59 (d, 2H), 7.25 (d, 1H), 7.08 (d, 1H), 6.69 (q, 1H), 6.34 (d, 1H), 4.64 (s, 2H), 3.97 (s, 2H), 2.24 (s, 3H). |
| 333 | δ 8.94 (s, 1H), 8.04 (q, 1H), 7.77 (d, 1H), 7.59 (d, 2H), 7.25 (d, 1H), 7.08 (d, 1H), 6.69 (q, 1H), 6.34 (d, 1H), 4.64 (s, 2H), 3.97 (s, 2H), 2.24 (s, 3H). |
| 339 | δ 7.71 (m, 2H), 7.34 (s, 1H), 7.27 (m, 1H), 7.13 (t, 2H), 6.59 (d, 1H), 6.28 (s, 1H), 4.62 (s, 2H), 3.97 (s, 2H), 2.25 (s, 3H). |
| 343 | δ 7.71 (m, 2H), 7.34 (s, 1H), 7.27 (m, 1H), 7.13 (t, 2H), 6.59 (d, 1H), 6.28 (s, 1H), 4.62 (s, 2H), 3.97 (s, 2H), 2.25 (s, 3H). |
| 344 | δ 7.31 (t, 2H), 7.24 (d, 2H), 7.18 (m, 2H), 7.08 (t, 1H), 6.93 (d, 2H), 6.89 (d, 1H), 6.82 (q, 1H), 6.76 (s, 1H), 6.54 (d, 1H), 4.60 (s, 2H), 3.95 (s, 2H), 2.22 (s, 3H). |
| 348 | δ 7.31 (t, 2H), 7.24 (d, 2H), 7.18 (m, 2H), 7.08 (t, 1H), 6.93 (d, 2H), 6.89 (d, 1H), 6.82 (q, 1H), 6.76 (s, 1H), 6.54 (d, 1H), 4.60 (s, 2H), δ 3.95 (s, 2H), 2.22 (s, 3H). |

Experimental Example 1

Activity and Cytotoxicity Test

The PPARδ activity of the compound represented by formula (I) of the present invention was confirmed by transfection assay. In addition, the selectivity to PPAR subtypes, PPARα and PPARγ was examined. Cytotoxicity was tested by MTT assay and in vivo activity was investigated by animal experiment.

Transfection Assay

CV-1 cells were used in this assay. The cells were inoculated in a 96-well plate containing DMEM supplemented with 10% FBS, DBS (delipidated) and 1% penicillin/streptomycin and cultured in a 37° C., 5% $CO_2$ incubator. The experiment was performed according to the steps of inoculation, transfection, sample treatment and confirmation. Particularly, CV-1 cells were inoculated in a 96 well-plate (5000 cells/well), followed by transfection 24 hours later. Full length PPARs plasmid DNA, reporter DNA confirming PPARs activity owing to its luciferase activity, β-galactosidase DNA providing information on transfection efficiency, and transfection reagent were used for the transfection. Samples were dissolved in dimethylsulfoxide (DMSO), which were treated to the cells via media at different concentrations. After culturing the cells in the incubator for 24 hours, the cells were lysed by using lysis buffer. Luciferase activity and β-galactosidase activity were measured with Luminometer and a microplate reader. The obtained values of luciferase were modified by the values of β-galactosidase. A graph was made with those values and $EC_{50}$ was calculated.

TABLE 6

| | $EC_{50}$ data | | |
| --- | --- | --- | --- |
| Compound No. | hPPARδ | hPPARα | hPPARγ |
| S14 | 2.6 nM | ia | ia |
| S22 | 9.3 nM | ia | ia |
| S23 | 12 nM | ia | ia |
| S46 | 3.7 nM | ia | ia |
| S66 | 33 nM | ia | ia |
| S106 | 3.2 nM | ia | ia |
| S164 | 4.5 nM | ia | ia |
| S306 | 53 nM | ia | ia |

As shown in Table 6, the compounds of the present invention are highly selective to PPARδ.

The activity of the compound of the present invention to PPARδ was 2 nM-200 nM.

MTT Assay

MTT assay was performed to test cytotoxicity of the compound represented by formula (I) of the present invention. MTT is a yellow substance soluble in water, but when it is introduced into a living cell, it turns into a purple insoluble crystal by dehydrogenase in mitochondria. Cytotoxicity can be confirmed by measuring $OD_{550}$ after dissolving MTT in dimethylsulfoxide. The experiment was performed as follows.

CV-1 cells were inoculated in a 96-well plate (5000 cells/well). The cells were cultured in a 37° C. 5% $CO_2$ incubator for 24 hours, and treated with samples at different concentrations. Then, the cells were cultured for 24 hours again, to which MTT reagent was added. After culturing for 15 minutes, the generated purple crystals were dissolved in dimethylsulfoxide. Optical density was measured with a microplate reader to confirm cytotoxicity.

As a result, the compound represented by formula (I) was confirmed not to have cytotoxicity even at the concentration of 100-1000 times the $EC_{50}$ value to PPAR.

Animal Test

Obesity Inhibitory Effect

An animal test using mice was performed to confirm the in vivo effect of the compound of the present invention. C57BL/6 (SLC Co.) mice at 8 weeks were used. To induce obesity, feeds containing 35% fat were given. While feeding such high-fat feeds for 60 days, vehicle, S14, S46 and S106 (10 mg/kg/day) were orally administered. As a result, only 31% of the S14 treated group mice showed weight increase, compared with the vehicle group, and 43% and 37% of the S46 treated group and the S106 treated group showed weight increase respectively.

Diabetes Improving Effect

GTT (glucose tolerance test) was performed to confirm the diabetes improving effect of the compound of the present invention. Glucose (1.5 g/Kg) was intra-abdominally administered to the mice pre-treated orally with samples for 57 days. Blood glucose was measured every hour. Fasting blood glucose was lower in the S14, S46 and S106 (10 mg/Kg/day) treated groups than in control. The group treated with the compound of the present invention exhibited rapid blood glucose decrease in 20-40 minutes and glucose clearance in 100 minutes. In the meantime, the blood glucose level was not recovered to normal in the vehicle treated group even after 120 minutes. The above results indicate that the compounds S14, S46 and S106 had diabetes improving effect.

Muscle Endurance Strengthening and Muscle Function Enhancing Effect

An animal test was performed to confirm muscle endurance strengthening and muscle function enhancing effect of the composition of the present invention. Most muscles are generated in developmental stage. Thus, S14, S46 and S106 (10 mg/Kg/day) were treated to pregnant mice in the period of either pregnancy or lactation or both pregnancy and lactation. Weight gaining and growth rate were not much different between fetuses of the control group and the treatment group. Muscles were observed after removing skin. As a result, muscles of the treatment group were red, unlike the control. ATPase staining and immunostaining were performed. As a result, type I muscle fiber was increased in the treatment group. The role of the changes of the muscle fiber in the enhancement of muscle endurance and muscle function was investigated by using treadmill test. As a result, running time was much extended in the treatment group, compared with the control.

TABLE 7

Results of muscle endurance test

| increasing rate (treatment group/control group) | pregnancy | | lactation | | pregnancy + lactation | |
|---|---|---|---|---|---|---|
| | time | length | time | length | time | length |
| S14 | 2.4 times | 2.5 times | 2.1 times | 2.2 times | 3.6 times | 3.9 times |
| S46 | 1.9 times | 1.9 times | 1.5 times | 1.5 times | 2.8 times | 3.0 times |
| S106 | 2.1 times | 2.2 times | 1.8 times | 1.8 times | 3.2 times | 3.4 times |

When the compound of the present invention was treated to adults, muscle endurance and muscle function were also enhanced. Particularly, S14, S46 and S106 were orally administered to C57BL/6 mice at 10 weeks at the concentration of 10 mg/kg, during which the mice were forced to exercise. The exercise was performed with treadmill for 30 minutes once a day for 30 days, precisely at the speed of 2 meter/min for the first 5 minutes, at 5 meter/min for 5 minutes, at 8 meter/min for 5 minutes and at 20 meter/min for the last 5 minutes. At the finish, muscle endurance and muscle function enhancing effect was tested by using treadmill. As a result, the time (S14 treated group: 1.5 fold, S46 treated group: 1.3 fold, S106 treated group: 1.4 fold increased) and distance (S14 treated group: 1.5 fold, S46 treated group: 1.3 fold, S106 treated group: 1.4 fold increased) of exercise were all increased in the treatment group, compared with the control.

Memory Improvement

An animal test was performed to investigate the therapeutic effect of the compound of the present invention on dementia and Parkinson's disease based on the memory improving effect thereof. To confirm the effect of the compound of the present invention in the period of brain development, the compound was orally administered to pregnant mice at the concentration of 10 mg/kg in the periods of pregnancy and lactation. Morris water maze test was performed to detect any changes of the brain functions of the treatment group and the control group. This test facilitates the study of spatial learning and memory, which largely depends on the hippocampus in the brain. As a result, the average time spent to find the platform was much shorter in the treatment group, compared with the control group; precisely, the treatment group spent 5.2 sec to find the platform (S14 treated group: 5.2 sec, S46 treated group: 7.8 sec, S106 treated group: 6.1 sec) and the control group spent 24.2 sec at average, suggesting that memory was enhanced significantly in the treatment group.

The therapeutic effect of the compound of the present invention on dementia and Parkinson's disease based on the memory improving effect thereof was investigated using brain disease animal model (C57BL/6 mice at 10 weeks). First, LPS was injected into the mouse brain to construct brain disease animal model. The mice were divided into four groups according to the administration and exercise. The exercise was performed with treadmill at the speed of 2 meter/min for the first 5 minutes, at 5 meter/min for 5 minutes, at 8 meter/min for 5 minutes and at 20 meter/min for the last 5 minutes. At the finish, Morris water maze test was performed. And the results are summarized in Table 8. As a result, the therapeutic effect of the compound of the invention on dementia and Parkinson's disease via memory enhancement by the compound and exercise was confirmed in the brain disease animal model.

TABLE 8

| Experiment group | | Results of water maze test |
|---|---|---|
| Vehicle | Exercise (X) | 32 seconds |
| | Exercise (○) | 24 seconds |
| S14 | Exercise (X) | 21 seconds |
| | Exercise (○) | 12 seconds |
| S46 | Exercise (X) | 27 seconds |
| | Exercise (○) | 18 seconds |
| S106 | Exercise (X) | 23 seconds |
| | Exercise (○) | 15 seconds |

INDUSTRIAL APPLICABILITY

The novel compound of the present invention is functioning as a PPAR activator ligand, so that it is a highly promising candidate for a pharmaceutical composition for the prevention and treatment of cardiovascular disease, diabetes, obesity, dementia and Parkinson's disease, for lowering cholesterol level, for strengthening muscles or for improving memory; a functional food adjuvant, a functional drink, a food additive, a functional cosmetic composition and a feed composition.

What is claimed is:

1. An aryl compound represented by Formula I, or a hydrate, a solvate, a stereoisomer or a pharmaceutically acceptable salt thereof;

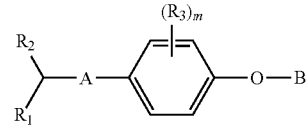

Formula I wherein, A is S or Se; B is H or

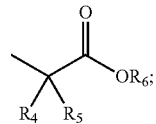

127

R₁ is aryl selected from the following structures;

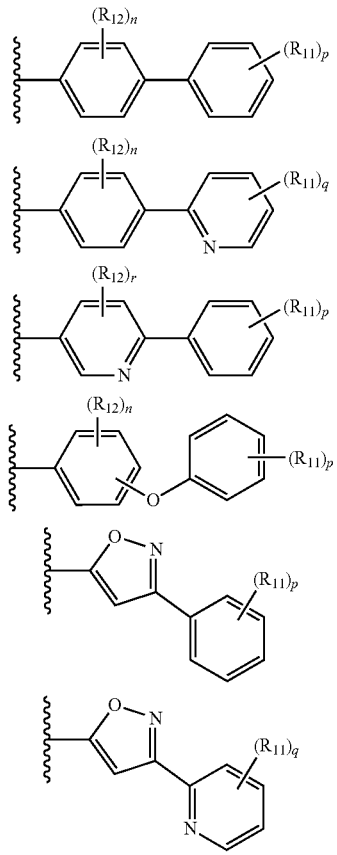

R₂ is H or

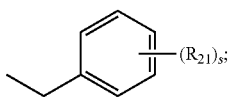

R₃ is H, C1-C8 alkyl or halogen; R₄ and R₅ are independently H or C1-C8 alkyl; R₆ is H, C1-C8 alkyl, C2-C7 alkenyl, alkali metal or alkali earth metal; R₁₁ and R₁₂ are independently H, C1-C8 alkyl or halogen; R₂₁ is H, halogen, C1-C7 alkyl, heterocyclic group or C1-C7 alkoxy; m and n are independently integers of 1-4; p is an integer of 1-5; q is an integer of 1-4; r is an integer of 1-3; s is an integer of 1-5; and alkyl and alkoxy of R₃, R₄, R₅, R₆, R₁₁, R₁₂ and R₂₁ can be substituted with one or more halogens or C1-C5 alkylamine; wherein, the case that R₂ is H and A is S is excluded.

2. The aryl compound, the hydrate, the solvate, the stereoisomer or the pharmaceutically acceptable salt thereof according to claim 1, wherein the R₁ is aryl selected from the following structures;

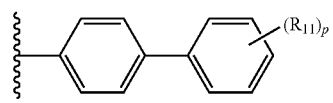

128

-continued

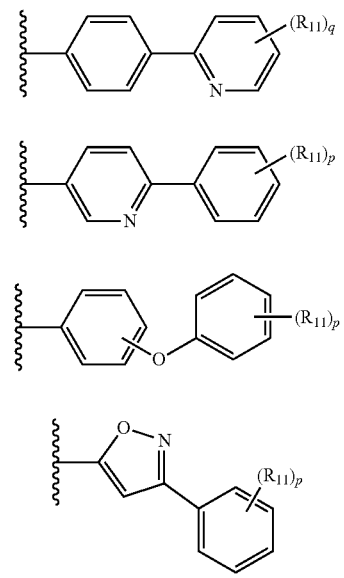

R₂ is

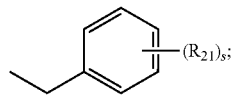

R₃ is C1-C5 alkyl substituted or non-substituted with halogen or halogen; R₄ and R₅ are independently H or C1-C5 alkyl substituted or non-substituted with halogen; R₆ is H, C1-C7 alkyl, alkali metal or alkali earth metal; R₁₁ and R₁₂ are independently H, C1-C5 alkyl substituted with one or more fluorines or fluorine; R₂₁ is H, halogen, C1-C5 alkyl substituted or non-substituted with halogen or C1-C5 alkoxy substituted or non-substituted with halogen; p is an integer of 1-5; q is an integer of 1-4; and s is an integer of 1-5.

3. The aryl compound, the hydrate, the solvate, the stereoisomer or the pharmaceutically acceptable salt thereof according to claim 1, wherein the aryl compound is the compound represented by Formula IV and the hydrate, the solvate, the stereoisomer and the pharmaceutically acceptable salt are of the same;

Formula IV wherein, A, R₁, R₃ and m are as defined in Formula I of claim 1.

4. The aryl compound, the hydrate, the solvate, the stereoisomer or the pharmaceutically acceptable salt thereof according to claim 1, wherein the aryl compound is the compound represented by Formula VIII and the hydrate, the solvate, the stereoisomer and the pharmaceutically acceptable salt are of the same;

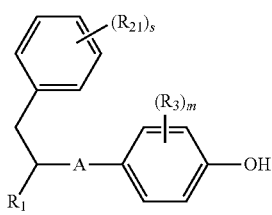

wherein, A, $R_1$, $R_3$, $R_{21}$, m and s are as defined in Formula I of claim 1.

5. A method for preparing the aryl compound represented by Formula I of claim 1 comprising the following steps:
   a) reacting the compound represented by Formula II with Grignard reagent and then reacting with organic lithium compound stepwise;
   b) adding S or Se powder to the mixture of step a); and
   c) reacting the mixture with the compound represented by Formula III to give the compound represented by formula IV;

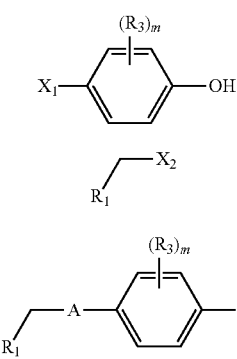

wherein, A, $R_1$, $R_3$ and m are as defined in Formula I of claim 1, $X_1$ is bromine atom or iodine atom, and $X_2$ is chlorine atom, bromine atom, iodine atom or leaving group having reactivity with nucleophilic substitution.

6. The method according to claim 5, wherein the compound represented by Formula IV is reacted with alkylhalogenacetate or alkylhalogenacetatealkylester to give the ester compound represented by Formula XI;

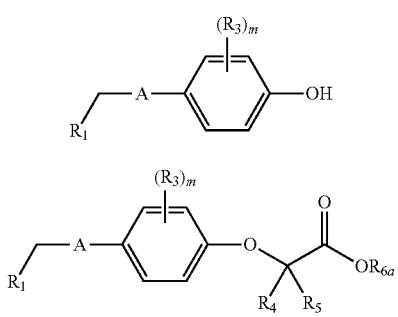

wherein, A, $R_1$, $R_3$, $R_4$, $R_5$ and m are as defined in Formula I of claim 1, and $R_{6a}$ is carboxylic acid protecting group having C1-C4 alkyl or allyl.

7. The method according to claim 6, wherein the ester compound represented by Formula XI is hydrolyzed to give the compound represented by Formula XII;

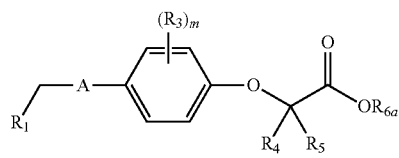

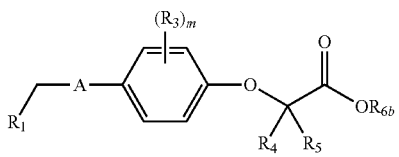

wherein, A, $R_1$, $R_3$, $R_4$, $R_5$ and m are as defined in Formula I of claim 1, $R_{6a}$ is carboxylic acid protecting group having C1-C4 alkyl or allyl, and $R_{6b}$ is H, alkali metal or alkali earth metal.

8. The method according to claim 5, wherein the alpha-hydrogen of thio or selenoether compound represented by Formula IV is treated with strong alkali and then reacted with the compound represented by Formula VI to give the compound represented by Formula VIII;

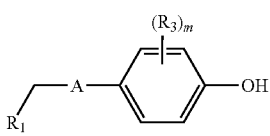

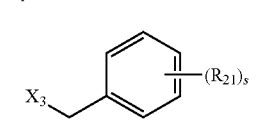

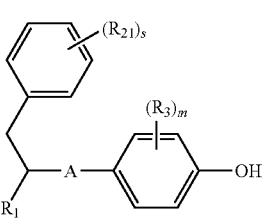

wherein, A, $R_1$, $R_3$, $R_{21}$, m and s are as defined in Formula I of claim 1, and $X_3$ is chlorine atom, bromine atom, iodine atom or leaving group.

9. The method according to claim 8, wherein the phenol group of the compound represented by Formula IV is protected by alkylsilyl group and then treated with strong alkali and the compound represented by Formula VI is added thereto and then the phenol protecting group is eliminated;

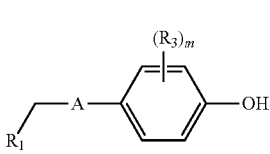

-continued

Formula VI

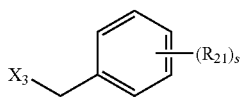

wherein, A, $R_1$, $R_3$, $R_{21}$, m and s are as defined in Formula I of claim 1, and $X_3$ is chlorine atom, bromine atom, iodine atom or leaving group.

10. The method according to claim 8, wherein the additional step is included in which the compound represented by Formula VIII is reacted with alkylhalogen acetate or alkylhalogen acetate alkylester to give the ester compound represented by Formula IX;

Formula VIII

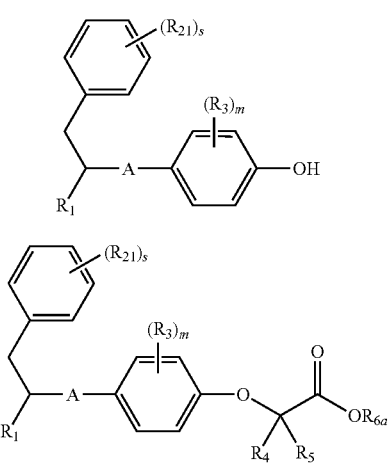

Formula IX wherein, A, $R_1$, $R_3$, $R_4$, $R_5$, $R_{21}$, m and s are as defined in Formula I of claim 1, and $R_{6a}$ is carboxylic acid protecting group having C1-C4 alkyl or allyl.

11. The method according to claim 10, wherein the additional step is included in which the ester compound represented by Formula IX is hydrolyzed to give the compound represented by Formula X;

Formula IX

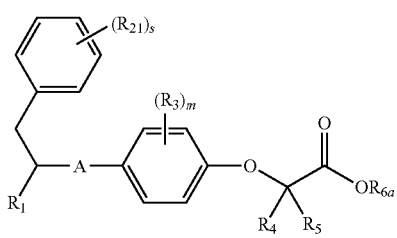

-continued

Formula X

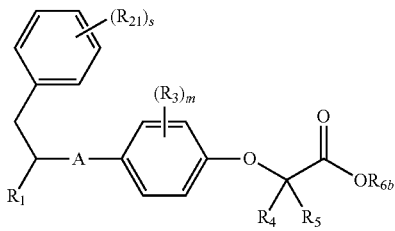

wherein, A, $R_1$, $R_3$, $R_4$, $R_5$, $R_{21}$, m and s are as defined in Formula I of claim 1, $R_{6a}$ is carboxylic acid protecting group having C1-C4 alkyl or allyl, and $R_{6b}$ is H, alkali metal or alkali earth metal.

12. A pharmaceutical composition for the inhibition and treatment of obesity, for the treatment of arteriosclerosis, hyperlipidemia, diabetes, dementia, or Parkinson's disease, for lowering cholesterol level, for strengthening muscles, for enhancing endurance or for improving memory, containing the aryl compound represented by Formula I of claim 1, or the hydrate, the solvate, the stereoisomer or the pharmaceutically acceptable salt thereof of as active ingredients.

13. A composition for functional food adjuvants, functional beverages, food additives and animal feeds containing the aryl compound represented by Formula I of claim 1, or the hydrate, the solvate, the stereoisomer or the pharmaceutically acceptable salt thereof as active ingredients.

14. A peroxisome proliferator activated receptor (PPAR) activator composition containing the aryl compound represented by Formula I of claim 1, or the hydrate, the solvate, the stereoisomer or the pharmaceutically acceptable salt thereof as active ingredients.

15. A pharmaceutical composition for the treatment of arteriosclerosis, for strengthening muscles, for enhancing endurance or for improving memory containing a peroxisome proliferator activated receptor (PPAR) activator of Formula I as an active ingredient.

16. A composition for functional food adjuvants, functional beverages, food additives and animal feeds containing a PPAR activator as an active ingredient, wherein the PPAR activator is an aryl compound represented by Formula I of claim 1, or the hydrate, the solvate, the stereoisomer or the pharmaceutically acceptable salt thereof.

17. A method of screening an activator for the prevention and treatment of arteriosclerosis, for strengthening muscle, for enhancing endurance or for improving memory, which comprises the steps of adding a PPAR activator candidate to PPAR; and measuring activity of PPAR, wherein the PPAR activator candidate is an aryl compound represented by Formula I of claim 1 or the hydrate, the solvate, the stereoisomer, or the pharmaceutically acceptable salt thereof.

* * * * *